(12) United States Patent
Yoshida et al.

(10) Patent No.: US 9,364,817 B2
(45) Date of Patent: Jun. 14, 2016

(54) OXIDE CATALYST AND METHOD FOR PRODUCING THE SAME, AND METHODS FOR PRODUCING UNSATURATED ALDEHYDE, DIOLEFIN, AND UNSATURATED NITRILE

(71) Applicant: Asahi Kasei Chemicals Corporation, Tokyo (JP)

(72) Inventors: Jun Yoshida, Tokyo (JP); Tatsuo Yamaguchi, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/429,720

(22) PCT Filed: Sep. 27, 2013

(86) PCT No.: PCT/JP2013/076364
§ 371 (c)(1),
(2) Date: Mar. 19, 2015

(87) PCT Pub. No.: WO2014/051090
PCT Pub. Date: Apr. 3, 2014

(65) Prior Publication Data
US 2015/0238939 A1    Aug. 27, 2015

(30) Foreign Application Priority Data

Sep. 28, 2012 (JP) ................. 2012-216071
Nov. 19, 2012 (JP) ................. 2012-253243
Feb. 22, 2013 (JP) ................. 2013-033663

(51) Int. Cl.
| | |
|---|---|
| *B01J 23/88* | (2006.01) |
| *C07C 5/48* | (2006.01) |
| *C07C 11/167* | (2006.01) |
| *B01J 23/889* | (2006.01) |
| *C07C 45/35* | (2006.01) |
| *C07C 253/26* | (2006.01) |
| *B01J 37/04* | (2006.01) |
| *B01J 23/881* | (2006.01) |
| *B01J 23/887* | (2006.01) |
| *B01J 35/00* | (2006.01) |
| *B01J 35/02* | (2006.01) |
| *B01J 35/10* | (2006.01) |
| *B01J 37/00* | (2006.01) |
| *C07C 47/22* | (2006.01) |
| *B01J 21/08* | (2006.01) |
| *B01J 37/08* | (2006.01) |
| *C07C 5/333* | (2006.01) |

(52) U.S. Cl.
CPC .............. *B01J 23/8898* (2013.01); *B01J 21/08* (2013.01); *B01J 23/88* (2013.01); *B01J 23/881* (2013.01); *B01J 23/8871* (2013.01); *B01J 23/8872* (2013.01); *B01J 23/8876* (2013.01); *B01J 35/002* (2013.01); *B01J 35/006* (2013.01); *B01J 35/023* (2013.01); *B01J 35/1009* (2013.01); *B01J 37/0045* (2013.01); *B01J 37/04* (2013.01); *B01J 37/08* (2013.01); *C07C 5/3332* (2013.01); *C07C 5/48* (2013.01); *C07C 45/35* (2013.01); *C07C 47/22* (2013.01); *C07C 253/26* (2013.01); *B01J 2523/00* (2013.01); *C07C 2523/18* (2013.01); *C07C 2523/28* (2013.01); *C07C 2523/31* (2013.01); *C07C 2523/745* (2013.01); *C07C 2523/887* (2013.01); *Y02P 20/52* (2015.11)

(58) Field of Classification Search
CPC ........... B01J 23/88; C07C 5/48; C07C 11/167
See application file for complete search history.

(56) References Cited

U.S. PATENT DOCUMENTS

| | | | |
|---|---|---|---|
| 4,258,217 A * | 3/1981 | Aoshima | B01J 23/8876 568/474 |
| 4,388,223 A | 6/1983 | Ferlazzo et al. | |

(Continued)

FOREIGN PATENT DOCUMENTS

| | | |
|---|---|---|
| EP | 2 727 648 A1 | 5/2014 |
| JP | 49-14392 A | 2/1974 |

(Continued)

OTHER PUBLICATIONS

"Petrochemical Process", Kodansha Scientific, pp. 172-176.
(Continued)

*Primary Examiner* — Nyeemah A Grazier
(74) *Attorney, Agent, or Firm* — Birch, Stewart, Kolasch & Birch, LLP

(57) ABSTRACT

An object of the present invention is to provide an oxide catalyst that prevents the reduction degradation of the catalyst even during industrial operation for a long time and less reduces unsaturated aldehyde yields, diolefin yields, or unsaturated nitrile yields, and a method for producing the same, and methods for producing unsaturated aldehyde, diolefin, and unsaturated nitrile using the oxide catalyst. The present invention provides an oxide catalyst for use in the production of unsaturated aldehyde, diolefin, or unsaturated nitrile from olefin and/or alcohol, the oxide catalyst satisfying the following (1) to (3): (1) the oxide catalyst comprises molybdenum, bismuth, iron, cobalt, and an element A having an ion radius larger than 0.96 Å (except for potassium, cesium, and rubidium); (2) an atomic ratio a of the bismuth to 12 atoms of the molybdenum is $1 \leq a \leq 5$, an atomic ratio b of the iron to 12 atoms of the molybdenum is $1.5 \leq b \leq 6$, an atomic ratio c of the element A to 12 atoms of the molybdenum is $1 \leq c \leq 5$, and an atomic ratio d of the cobalt to 12 atoms of the molybdenum is $1 \leq d \leq 8$; and (3) the oxide catalyst comprises a disordered phase consisting of a crystal system comprising the molybdenum, the bismuth, the iron, and the element A.

13 Claims, 7 Drawing Sheets

(56) References Cited

U.S. PATENT DOCUMENTS

Figure 1:
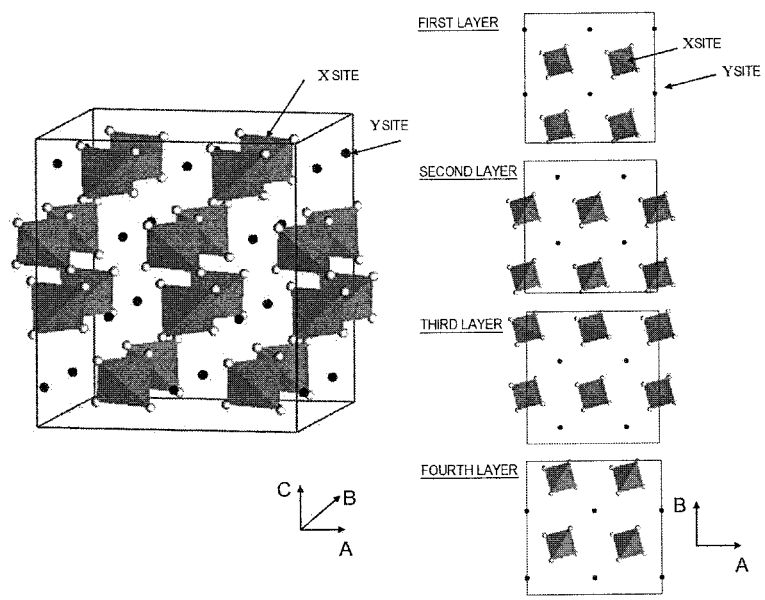

| | | | |
|---|---|---|---|
| 4,424,141 A * | 1/1984 | Grasselli | B01J 23/002 502/205 |
| 5,728,894 A | 3/1998 | Nagano et al. | |
| 7,012,039 B2 * | 3/2006 | Watanabe | B01J 23/002 502/300 |
| 7,906,689 B2 * | 3/2011 | Zhuang | B01J 23/002 502/248 |
| 8,088,947 B2 * | 1/2012 | Kurakami | B01J 21/04 562/519 |
| 8,361,923 B2 * | 1/2013 | Kano | B01J 23/002 502/107 |
| 9,211,527 B1 * | 12/2015 | Brazdil, Jr. | B01J 23/8878 |
| 2004/0116280 A1 | 6/2004 | Kawato et al. | |
| 2011/0028312 A1 * | 2/2011 | Miura | B22F 9/24 502/313 |
| 2013/0072710 A1 | 3/2013 | Brazdil et al. | |
| 2014/0171303 A1 * | 6/2014 | Yoshida | C07C 45/35 502/304 |

FOREIGN PATENT DOCUMENTS

| | | |
|---|---|---|
| JP | 57-171437 A | 10/1982 |
| JP | 61-12488 B2 | 4/1986 |
| JP | 5-253480 A | 10/1993 |
| JP | 2002-239386 A | 8/2002 |
| JP | 2006-61888 A | 3/2006 |
| JP | 2010-120933 A | 6/2010 |
| JP | 2010-253414 A | 11/2010 |
| JP | 2012-45516 A | 3/2012 |
| TW | 351313 B | 11/2011 |
| WO | WO 95/35273 A1 | 12/1995 |
| WO | WO 2005/049200 A1 | 6/2005 |

OTHER PUBLICATIONS

International Search Report, issued in PCT/JP2013/076364, dated Oct. 29, 2013.

Jeitschko et al., "A Comprehensive Study of Disordered and Ordered Scheelite-Related $Bi_3(FeO_4)(MoO_4)_2$", Acta Cryst. (1976), B32, 1163.

Supplementary European Search Report issued Sep. 17, 2015, in European Patent Application No. 13841762.1.

* cited by examiner (a)  (b)

OXIDE CATALYST AND METHOD FOR PRODUCING THE SAME, AND METHODS FOR PRODUCING UNSATURATED ALDEHYDE, DIOLEFIN, AND UNSATURATED NITRILE

TECHNICAL FIELD

The present invention relates to an oxide catalyst and a method for producing the same, and methods for producing unsaturated aldehyde, diolefin, and unsaturated nitrile using the oxide catalyst.

BACKGROUND ART

A large number of oxide catalysts for use in the production of unsaturated aldehyde as a main component have been reported so far. For example, the oldest oxide catalyst was found by Standard Oil Co. of Ohio and is known as a composite oxide catalyst comprising Mo and Bi as essential components. Patent Literature 1 describes a catalyst by focusing on Mo, Bi, Ce, K, Fe, Co, Mg, Cs, and Rb as metals constituting the catalyst.

The method for producing unsaturated aldehyde is used in, for example, a method for producing (meth)acrylate such as methyl acrylate or methyl methacrylate through oxidative esterification reaction using at least one starting material selected from the group consisting of propylene, isobutylene, isobutanol, and t-butyl alcohol and an intermediate unsaturated aldehyde such as acrolein or methacrolein. This method for producing (meth)acrylate is also known as a so-called direct methyl esterification process consisting of two reaction steps or as a so-called direct oxidation process consisting of three reaction steps. The direct oxidation process produces (meth)acrylate by three steps (see e.g., Non-Patent Literature 1). The first oxidation step of the direct oxidation process is a step of producing unsaturated aldehyde such as acrolein or methacrolein through the gas-phase catalytic oxidation reaction of at least one starting material selected from the group consisting of propylene, isobutylene, and t-butyl alcohol with molecular oxygen in the presence of a catalyst. The second oxidation step of this process is a step of producing (meth)acrylic acid through the gas-phase catalytic oxidation reaction of the unsaturated aldehyde obtained in the first oxidation step with molecular oxygen in the presence of a catalyst. The final esterification step is a step of further esterifying the (meth)acrylic acid obtained in the second oxidation step to obtain (meth)acrylate. The esterification using alcohol such as methanol can yield methyl acrylate or methyl methacrylate.

By contrast, the direct methyl esterification process consists of two catalyst reaction steps: a first reaction step of producing unsaturated aldehyde such as acrolein or methacrolein through the gas-phase catalytic oxidation reaction of at least one starting material selected from the group consisting of propylene, isobutylene, isobutanol, and t-butyl alcohol with molecular oxygen-containing gas; and a second reaction step of reacting the unsaturated aldehyde thus obtained with alcohol such as methanol and molecular oxygen to produce (meth)acrylate such as methyl acrylate or methyl methacrylate at once.

Reaction systems using such oxide catalysts include fixed-bed, fluidized-bed, and moving-bed reaction systems. Of them, the fixed-bed reaction system is frequently adopted industrially by virtue of the following advantage: high reaction yields can be achieved by feed gas flowing in a state close to extrusion flow.

The fixed-bed reaction system, however, has low heat conductivity and is therefore unsuitable for exothermic reaction or endothermic reaction that requires heat removal or heating. Particularly, severe exothermic reaction, such as oxidation reaction, where the temperature suddenly rises, disadvantageously gets beyond control of the reaction system, possibly resulting in runaway reaction. In addition, such a sudden rise in temperature damages the catalyst, resulting in the unfavorable early degradation of the catalyst.

By contrast, the fluidized-bed reaction system has high heat conductivity because catalyst particles vigorously flow in the reactor. Thus, the temperature in the reactor is kept almost constant even during reaction in which heat is largely generated or absorbed. The fluidized-bed reaction system can advantageously prevent the reaction from excessively progressing. This reaction system also has the advantage that, because of the reduced local accumulation of energy, feed gas in an explosive range can be reacted so that the starting material concentration is increased to improve productivity. Thus, the fluidized-bed reaction system is suitable for the catalytic oxidation reaction of olefin and/or alcohol, which is high exothermic reaction. In spite of these known advantages of the fluidized-bed reaction system, Patent Literatures 2 and 3, for example, state that use of fixed-bed catalysts is generally preferred for converting unsaturated hydrocarbon to unsaturated aldehyde. These literatures state that the catalysts described therein may be used in any of fixed-bed, moving-bed, and fluidized-bed methods for producing unsaturated aldehyde through the catalytic oxidation reaction of olefin and/or alcohol, but make no specific mention about reaction systems other than the fixed-bed one.

Although naphtha pyrolysis is mainstream as a method for producing diolefin such as 1,3-butadiene, there is a growing demand for production based on gas-phase oxidation reaction along with a recent shift to alternative resources to petroleum. Examples of the method for producing diolefin by use of the gas-phase oxidation reaction include methods which involve subjecting monoolefin having 4 or more carbon atoms, such as n-butene or isopentene, and molecular oxygen to catalytic oxidative dehydrogenation reaction in the presence of a catalyst to produce conjugated diolefin, such as 1,3-butadiene or isoprene, corresponding to the monoolefin. As for the catalyst used in such reaction, for example, Patent Literature 4 describes an oxide catalyst comprising Mo, Bi, Fe, Ce, Ni, Mg, and Rb as a catalyst for the oxidative dehydrogenation reaction of monoolefin.

A known method for producing unsaturated nitrile such as acrylonitrile or methacrylonitrile involves reacting one or more selected from the group consisting of propylene, isobutylene, isobutanol, and t-butyl alcohol, with molecular oxygen and ammonia in the presence of a catalyst. This method is widely known as an "ammoxidation process" and is currently practiced at an industrial scale.

Catalysts for use in the ammoxidation process have been diligently studied with the aim of further efficiently carrying out the method for producing unsaturated nitrile at an industrial scale. For example, Mo—Bi—Fe—Ni or Mo—Bi—Fe—Sb composite metal oxide catalysts are known as such catalysts for ammoxidation. Composition composed of these essential metals supplemented with other components has also been frequently studied with the aim of improving performance. For example, Patent Literature 5 discloses a catalyst comprising molybdenum, bismuth, iron, cerium, and nickel supplemented with other components. Also, Patent Literature 6 discloses a catalyst comprising molybdenum, bismuth, iron, antimony, nickel, and chromium supplemented with other components.

According to Non-Patent Literature 2, the disordered phase, which is a metastable structure, refers to a structure containing Mo sites randomly substituted by Fe, for example, in the case of a Bi—Mo—Fe 3-component composite oxide, and is characterized in that Mo and Fe atoms form the same oxygen tetrahedron structure. On the other hand, the ordered phase, which is a stable structure, has the same composition as that of the disordered phase, but structurally differs therefrom, and is obtained by heat treatment at a higher temperature than that for the disordered phase. In the ordered phase, Fe and Mo atoms individually form tetrahedrons. This means that the Fe atom forms an oxygen tetrahedron while the Mo atom forms another oxygen tetrahedron, aside from the Fe atom. Non-Patent Literature 2 states that a $Bi_3Fe_1Mo_2O_{12}$ disordered phase is formed at 450° C., but undergoes phase transition to the ordered phase at a reaction temperature of 475° C.

1) Disordered Phase $Bi_3Fe_1Mo_2O_{12}$

FIG. 1 shows the crystal structure of the disordered phase $Bi_3Fe_1Mo_2O_{12}$ described in Non-Patent Literature 2. This disordered phase is a tetragonal system of scheelite-type crystal ($CaWO_4$ type) with two equal side lengths and three axial angles of 90 degrees in the lattice constant of a unit cell (A=B≠C and α=β=γ=90 degrees). This phase has two sites: the X sites, which are enclosed in oxygen tetrahedrons, and the Y sites, which are not enclosed by oxygen atoms. The X sites are occupied by Mo and Fe either at random or with a certain probability distribution. The Y sites are occupied by Bi and other elements or lattice defects either at random or with a certain probability distribution. In each layer in the plane AB, the X sites and the Y sites form planar square lattices with lengths equal to those of the lattice constants in the A-axis and B-axis directions, respectively, and occupy positions displaced in the A-axis and B-axis directions, respectively, by ½ of the lattice constant in plane. These layers in the plane AB are stacked in the C-axis direction while repetitively displaced by (A/2, 0) and (0, B/2), respectively. In this stacking, the oxygen tetrahedrons around the X sites are placed while rotating about the C-axis by 90 degrees with their incorporated atoms centered.

Figure 3:
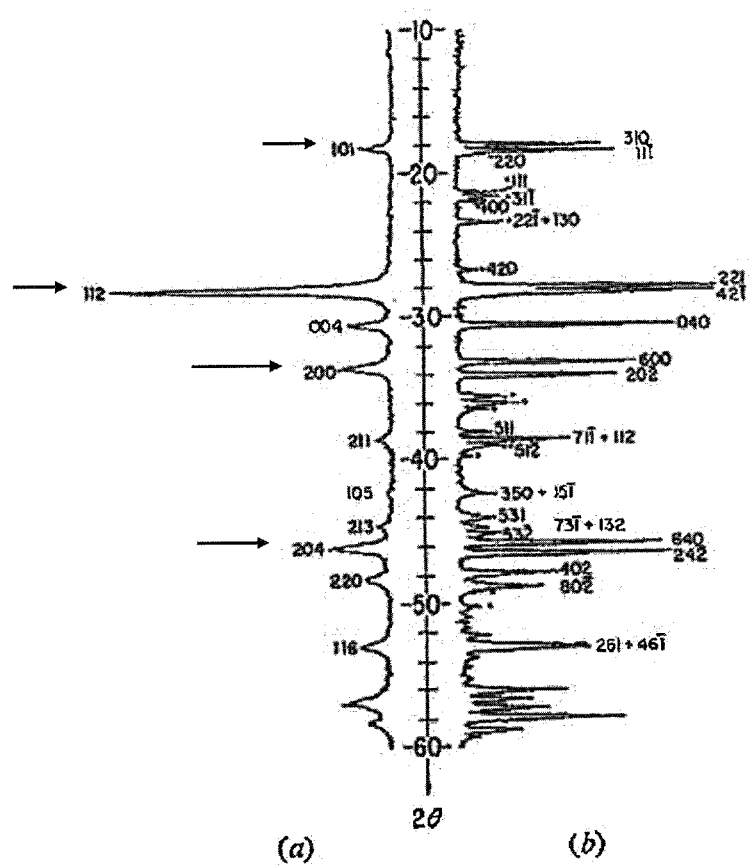

FIG. 3 shows the X-ray diffraction (XRD) of the disordered phase $Bi_3Fe_1Mo_2O_{12}$. This disordered phase exhibits single peaks at least in the 18.30°±0.2° (101), 28.20°±0.2° (112), 33.65°±0.2° (200), and 46.15°±0.2° (204) planes in the range of X-ray diffraction angles 2θ=10° to 60° measured by crystal X-ray diffraction (XRD).

2) Ordered Phase $Bi_3Fe_1Mo_2O_{12}$

Figure 2:
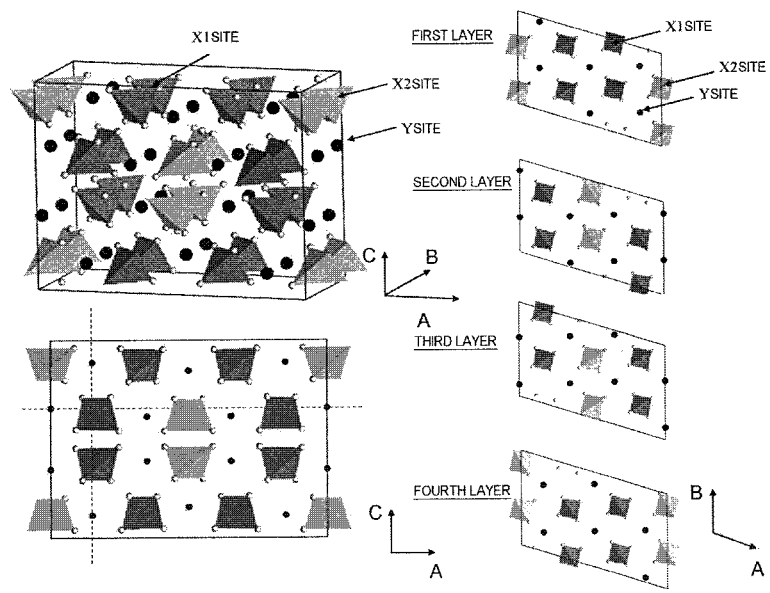

For comparison, the crystal structure of the ordered phase $Bi_3Fe_1Mo_2O_{12}$ is shown in FIG. 2. This ordered phase is a monoclinic crystal system having a distorted scheelite structure with different side lengths in the lattice constant of a unit cell. Two out of three angles formed by basic vectors are 90 degrees and the other angle is different (A≠B≠C, α=γ=90 degrees, and β≠90 degrees). The ordered phase has three sites: two unequivalent sites X1 and X2, which are enclosed in oxygen tetrahedrons, and the Y sites, which are not enclosed by oxygen atoms. The X1 sites are occupied by Mo and other elements or lattice defects. The X2 sites are occupied by Fe and other elements or lattice defects. The Y sites are occupied by Si and other elements or lattice defects.

3) Structural Difference between Disordered Phase $Bi_3Fe_1Mo_2O_{12}$ and Ordered Phase $Bi_3Fe_1Mo_2O_{12}$ In the disordered phase $Bi_3Fe_1Mo_2O_{12}$, the X sites or the Y sites are equivalent to one another, or elements of different types coordinate at random. In the ordered phase, the X sites or the Y sites are occupied regularly and distinctively by elements of different types or defects so that these two types of sites are differentiated. The ordered phase therefore exhibits peak splitting in the X-ray diffraction, whereas the disordered phase is characterized in that single peaks are detected (indicated by the arrows in FIG. 3). In measurement in the range of X-ray diffraction angles 2θ=10° to 60°, the peak in the 18.30°±0.05° (101) plane of the disordered phase $Bi_3Fe_1Mo_2O_{12}$ is split into 18.15°±0.05° (310) and 18.50°±0.05° (111) planes; the peak in the 28.20°±0.05° (112) plane of the disordered phase is split into 28.05°±0.05° (221) and 28.40°±0.05° (42-1) planes; the peak in the 33.65°±0.05° (200) plane of the disordered phase is split into 33.25°±0.05° (600) and 34.10°±0.05° (202) planes; and the peak in the 46.15°±0.05° (204) plane of the disordered phase is split into 45.85°±0.05° (640) and 46.50°±0.05° (242) planes.

CITATION LIST

Patent Literature

Patent Literature 1: International Publication No. WO 95/35273
Patent Literature 2: Japanese Patent Laid-Open No. S49-14392
Patent Literature 3: Japanese Patent Publication No. S61-12488
Patent Literature 4: Japanese Patent Laid-Open No. 2010-120933
Patent Literature 5: Japanese Patent Laid-Open No. 2006-61888
Patent Literature 6: Japanese Patent Laid-Open No. 2010-253414

Non-Patent Literature

Non-Patent Literature 1: Chemical Process of Petroleum, ed. by The Japan Petroleum Institute, p. 172-176, Kodansha Scientific Ltd.
Non-Patent Literature 2: Acta. Cryst (1976). 332, p. 1163-1170

SUMMARY OF INVENTION

Technical Problem

The oxide catalysts disclosed in Patent Literatures 4, 5, and 6 largely improve the initial yields of reaction, but still cannot produce sufficiently satisfactory yields in industrial operation for a long time. These catalysts, when used for a long time in a method for producing unsaturated aldehyde, diolefin, or unsaturated nitrile, are disadvantageously degraded due to reduction by propylene, isobutylene, isobutanol, n-butene, t-butyl alcohol, and ammonia, etc.

Reaction conditions of a high isobutylene concentration and a high reaction temperature are desired from the viewpoint of the productivity of unsaturated aldehyde. In this case, the catalysts are more susceptible to reduction degradation. In addition, the produced unsaturated aldehyde may also be decomposed, resulting in unfavorable decrease in the yield of unsaturated aldehyde.

The present inventors have hypothesized, as follows, the reason why a fixed-bed reaction system is practically adopted, though it is generally accepted that a fluidized-bed reaction system, which is advantageous in the control of a temperature in the reactor, is suitable in light of industrial practice: the unsaturated aldehyde which is the product of interest easily undergoes combustion decomposition in a high-temperature atmosphere containing oxygen in the reactor before reaching the reactor outlet, due to its very high reactivity, and is sequentially decomposed into unsaturated carboxylic acid or carbon dioxide. In addition, the fluidized-bed reaction system which involves the contact between products and catalysts requires: a rich layer where most of the catalysts are present in a flow state; and a dilute layer which is space for decreasing linear velocity for catalyst separation. The residence time of the products in the reactor after leaving the catalyst layer (rich layer) is therefore at least 10 times longer than that in the fixed-bed reactor. This further promotes the decomposition of the unsaturated aldehyde (product of interest) in the reactor, as can be imagined. As a result, reduction in the yield of unsaturated aldehyde is an unavoidable problem for the fluidized-bed reaction system.

Heretofore, the fluidized-bed reaction system, which is supposed to be industrially advantageous from the viewpoint of temperature control, has not been practically used in the production of unsaturated aldehyde through the catalytic oxidation reaction of olefin and/or alcohol, and instead, the fixed-bed reaction system has been used therein. This is probably due to the absence of means to prevent the decomposition of highly reactive unsaturated aldehyde. Presumably, there has been no choice but to adopt the fixed-bed reaction system excellent in the recovery of products, even if industrial efficiency has been traded off for preventing product decomposition and securing necessary yields.

The present invention has been made in light of the problems described above, and an object of the present invention is to provide an oxide catalyst that prevents the reduction degradation of the catalyst even during industrial operation for a long time and less reduces unsaturated aldehyde yields, diolefin yields, or unsaturated nitrile yields, and a method for producing the same, and methods for producing unsaturated aldehyde, diolefin, and unsaturated nitrile using the oxide catalyst.

Solution to Problem

As shown in Non-Patent Literature 1, the disordered phase is thermally unstable. It has previously been considered that the disordered phase carried by a catalyst for use in gas-phase oxidation reaction that is performed at a high temperature has no merit.

Nonetheless, the studies conducted by the present inventors have revealed that some disordered phases are stably present even at a high temperature and can be stably present for a very long time even in a reductive atmosphere. On the basis of this discovery, the present inventors have conducted diligent studies and consequently completed the present invention by finding that a catalyst having a disordered phase that is stable even at a high temperature and has high reduction resistance can be obtained by the successful incorporation of an element having a predetermined ion radius into the crystal structure.

Specifically, the present invention is as follows:

[1]

An oxide catalyst for use in the production of unsaturated aldehyde, diolefin, or unsaturated nitrile from olefin and/or alcohol, the oxide catalyst satisfying the following (1) to (3):

(1) the oxide catalyst comprises molybdenum, bismuth, iron, cobalt, and an element A having an ion radius larger than 0.96 Å (except for potassium, cesium, and rubidium);

(2) an atomic ratio a of the bismuth to 12 atoms of the molybdenum is $1 \leq a \leq 5$, an atomic ratio b of the iron to 12 atoms of the molybdenum is $1.5 \leq b \leq 6$, an atomic ratio c of the element A to 12 atoms of the molybdenum is $1 \leq c \leq 5$, and an atomic ratio d of the cobalt to 12 atoms of the molybdenum is $1 \leq d \leq 8$; and (3) the oxide catalyst comprises a disordered phase consisting of a crystal system comprising the molybdenum, the bismuth, the iron, and the element A.

[2]

The oxide catalyst according to the above item [1], wherein the oxide catalyst has a single peak in each range of diffraction angles (2θ) of 18.30°±0.2°, 28.20°±0.2°, 33.65°±0.2°, and 46.15°±0.2° in X-ray diffraction, and an intensity ratio (Ia/Ib) of intensity (Ia) of peak a at 2θ=33.65°±0.2° to intensity (Ib) of peak b at 2θ=34.10°±0.2° is 2.0 or larger.

[3]

The oxide catalyst according to the above item [1] or [2], wherein the oxide catalyst has a composition represented by the following composition formula (1):

$$Mo_{12}Bi_aFe_bA_cCo_dB_eC_fO_g \quad (1)$$

wherein Mo represents molybdenum; Bi represents bismuth; Fe represents iron; the element A represents an element having an ion radius larger than 0.96 Å (except for potassium, cesium, and rubidium); Co represents cobalt; an element B represents at least one element selected from the group consisting of magnesium, zinc, copper, nickel, manganese, chromium, and tin; an element C represents at least one element selected from the group consisting of potassium, cesium, and rubidium; a to g each represent the atomic ratio of each element to 12 Mo atoms wherein the atomic ratio a of Bi is $1 \leq a \leq 5$, the atomic ratio b of Fe is $1.5 \leq b \leq 6$, the atomic ratio c of the element A is $1 \leq c \leq 5$, and the atomic ratio d of Co is $1 \leq d \leq 8$, an atomic ratio e of the element B is $0 \leq e < 3$, an atomic ratio f of the element C is $0 \leq f \leq 2$, and a ratio of Fe/Co is $0.8 \leq b/d$; and g represents a atomicity of oxygen determined by a valences of constituent elements other than oxygen.

[4]

The oxide catalyst according to any one of the above items [1] to [3], further comprising at least one selected from the group consisting of silica, alumina, titania, and zirconia as a carrier.

[5]

A method for producing an oxide catalyst, comprising:

a mixing step of mixing a starting material constituting the catalyst, comprising molybdenum, bismuth, iron, cobalt, and an element A having an ion radius larger than 0.96 Å (except for potassium, cesium, and rubidium), to obtain a slurry;

a drying step of drying the slurry thus obtained to obtain a dried product; and a calcination step of calcining the dried product thus obtained, wherein the calcination step comprises a heating step of gradually heating the dried product from 100° C. to 200° C. over 1 hour or longer.

[6]

The method for producing the oxide catalyst according to the above item [5], wherein the slurry has a pH of 8 or lower.

[7]

The method for producing the oxide catalyst according to the above item [5] or [6], wherein the calcination step comprises:

a preliminary calcination step of preliminarily calcining the dried product at a temperature of 200 to 300° C. to obtain a preliminarily calcined product; and a final calcination step of finally calcining the preliminarily calcined product thus obtained at a temperature of 300° C. or higher to obtain the catalyst.

[8]
A method for producing unsaturated aldehyde, comprising an unsaturated aldehyde production step of oxidizing olefin and/or alcohol using the oxide catalyst according to any one of the above items [1] to [4] to obtain the unsaturated aldehyde.

[9]
The method for producing unsaturated aldehyde according to the above item [8], wherein the olefin and/or the alcohol is at least one selected from the group consisting of propylene, isobutylene, propanol, isopropanol, isobutanol, and t-butyl alcohol.

[10]
The method for producing unsaturated aldehyde according to the above item [8] or [9], wherein the unsaturated aldehyde production step comprises a discharging step of discharging a product gas comprising the unsaturated aldehyde from a fluidized-bed reactor through the gas-phase catalytic oxidation reaction of the olefin and/or the alcohol with an oxygen source in the fluidized-bed reactor.

[11]
The method for producing unsaturated aldehyde according to any one of the above items [8] to [10], wherein
the gas-phase catalytic oxidation reaction is performed at a reaction temperature of 400 to 500° C., and
the product gas discharged from the fluidized-bed reactor has an oxygen concentration of 0.03 to 0.5% by volume.

[12]
A method for producing diolefin, comprising a diolefin production step of oxidizing monoolefin having 4 or more carbon atoms using the oxide catalyst according to any one of the above items [1] to [4] to obtain the diolefin.

[13]
A method for producing unsaturated nitrile, comprising an unsaturated nitrile production step of reacting at least one selected from the group consisting of propylene, isobutylene, propanol, isopropanol, isobutanol, and t-butyl alcohol, with molecular oxygen and ammonia in a fluidized-bed reactor using the oxide catalyst according to any one of the above items [1] to [4] to obtain the unsaturated nitrile.

Advantageous Effects of Invention

The present invention can provide an oxide catalyst that prevents the reduction degradation of the catalyst even during industrial operation for a long time and less reduces unsaturated aldehyde yields, diolefin yields, or unsaturated nitrile yields, and a method for producing the same, and methods for producing unsaturated aldehyde, diolefin, and unsaturated nitrile using the oxide catalyst.

DESCRIPTION OF EMBODIMENTS

Figure 4:
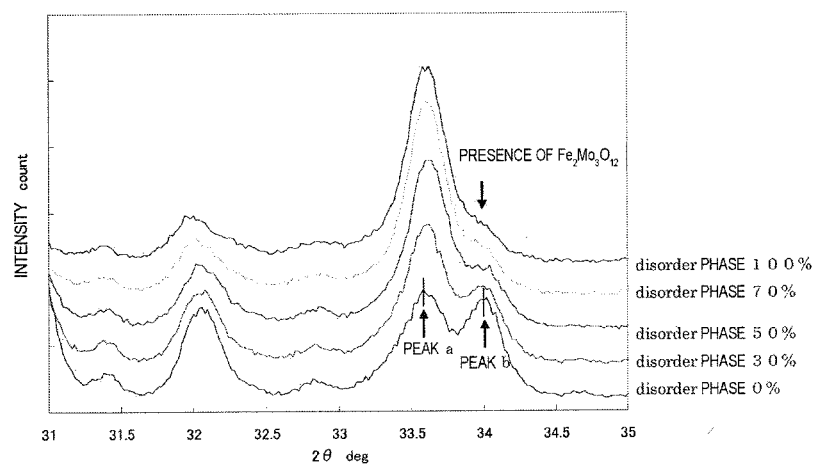
Figure 5:
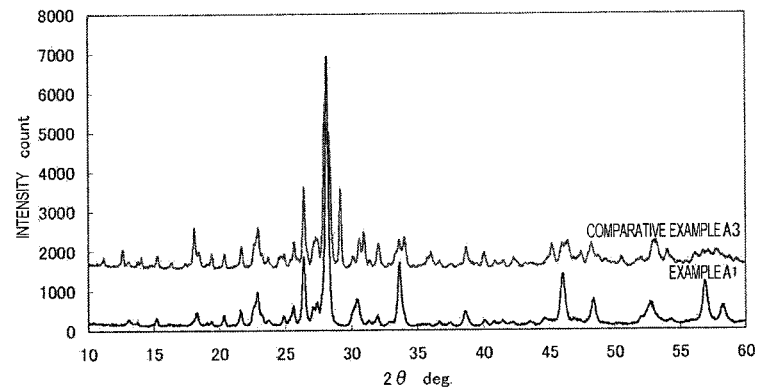
Figure 6:
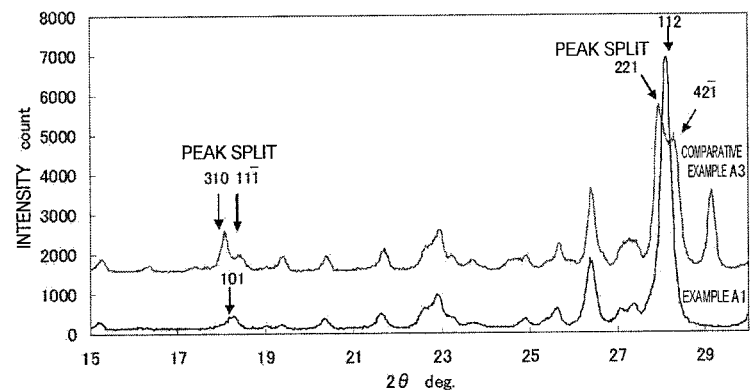
Figure 7:
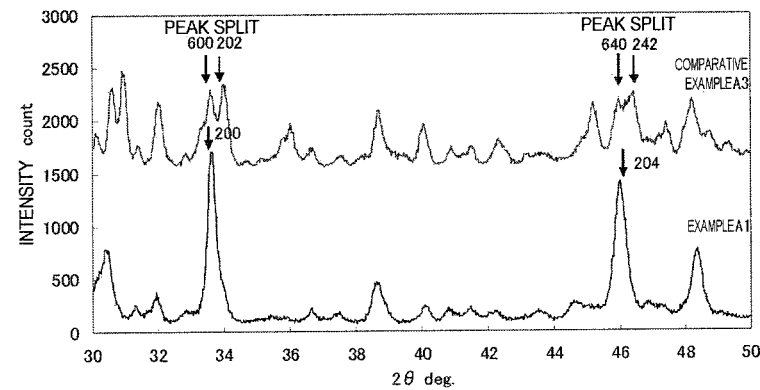
Figure 8:
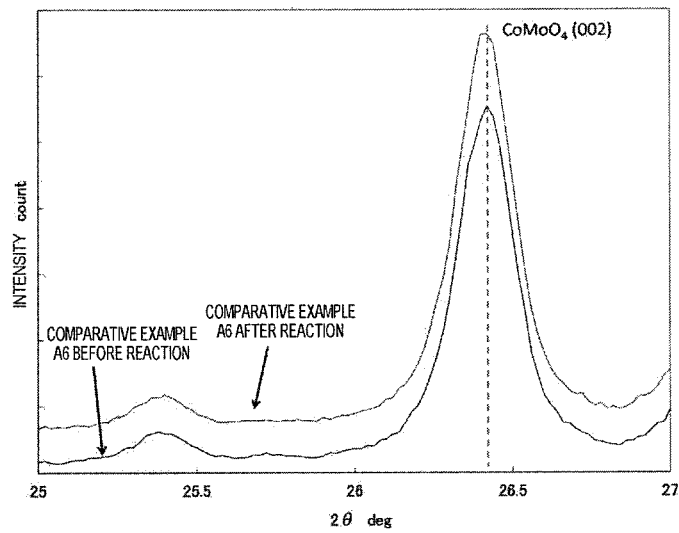
Figure 9:
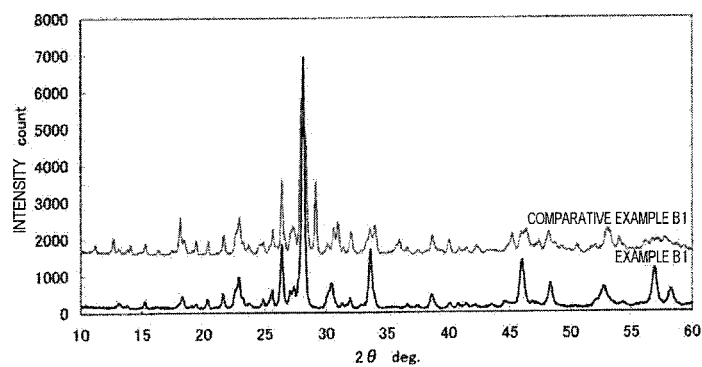
Figure 10:
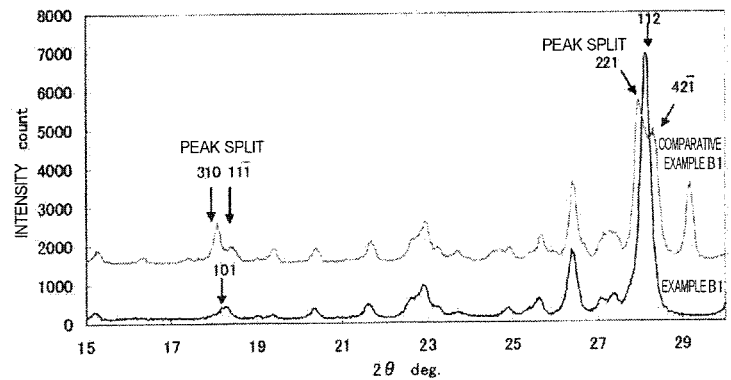
Figure 11:
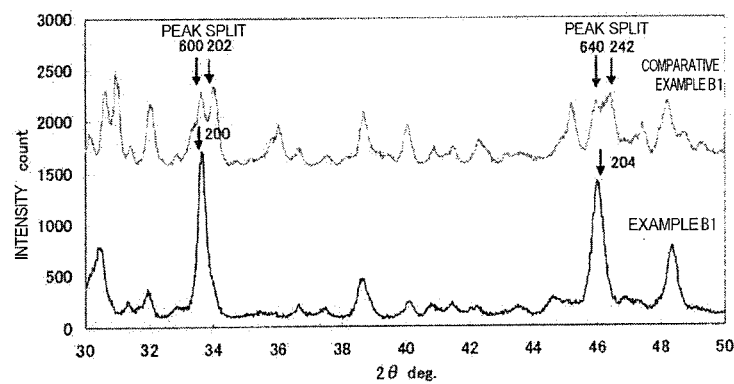
Figure 12:
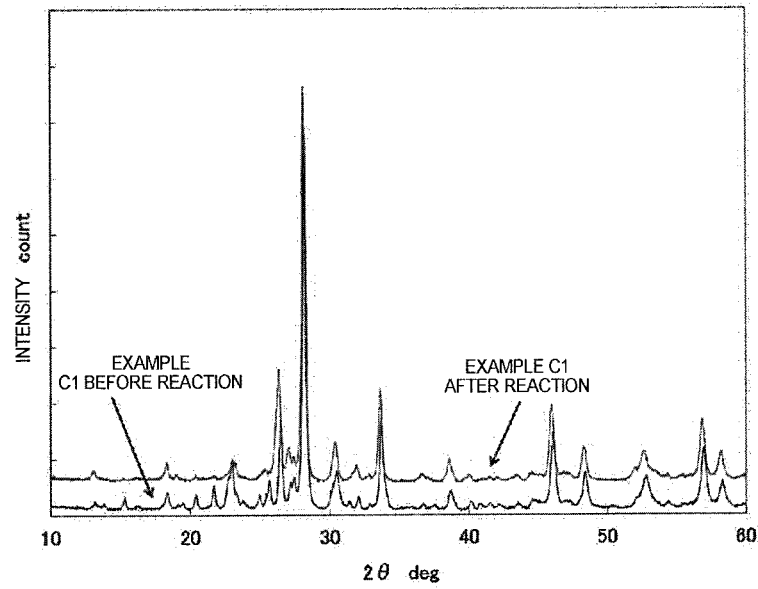
Figure 13:
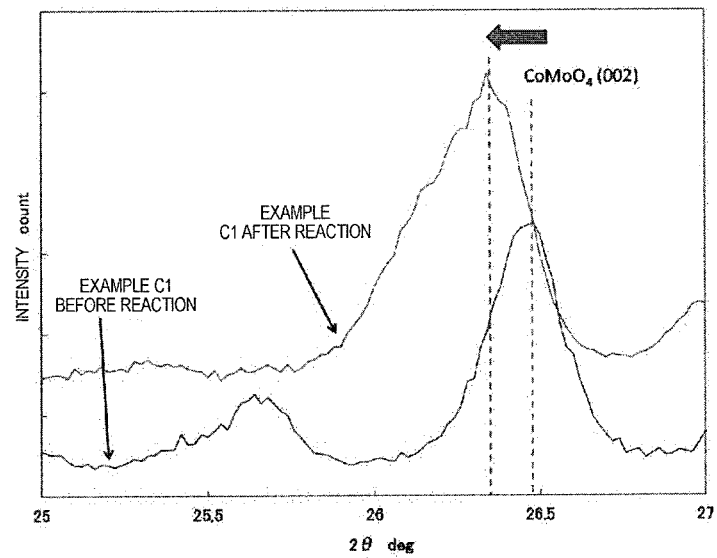
Figure 14:
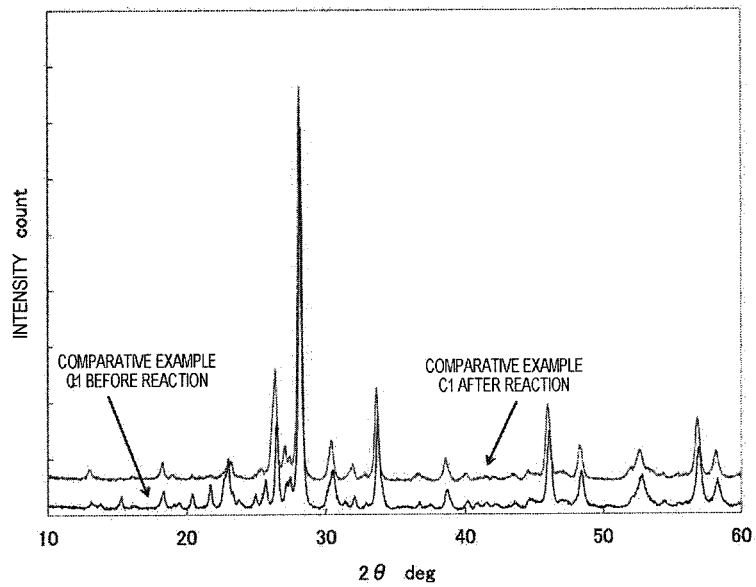
Figure 15:
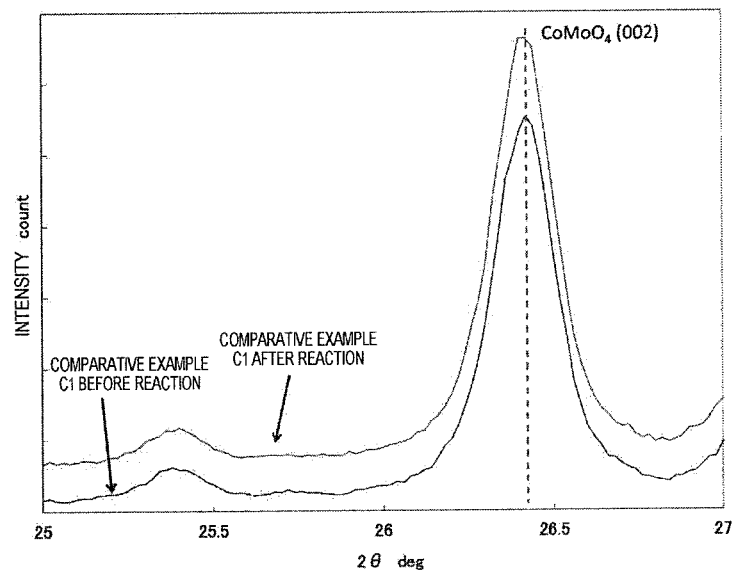
Figure 16:
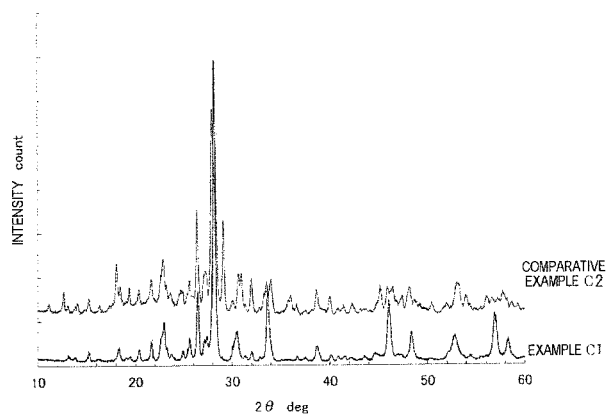

FIG. 1 is a schematic view illustrating the crystal structure of a disordered phase of $Bi_3Fe_1Mo_2O_{12}$;
FIG. 2 is a schematic view illustrating the crystal structure of an ordered phase of $Bi_3Fe_1Mo_2O_{12}$;
FIG. 3A is a chart illustrating the X-ray diffraction of the disordered phase of $Bi_3Fe_1Mo_2O_{12}$ and FIG. 3B is a chart illustrating the X-ray diffraction of the ordered phase of $Bi_3Fe_1Mo_2O_{12}$;
FIG. 4 is a chart illustrating the relation between the content rate of disordered phase and peaks a and b;
FIG. 5 is a chart illustrating the X-ray diffraction of catalysts obtained in Example A1 and Comparative Example A3;
FIG. 6 is an enlarged chart illustrating the range of 2θ=15 to 30° in X-ray diffraction in FIG. 5;
FIG. 7 is an enlarged chart illustrating the range of 2θ=30 to 50° in X-ray diffraction in FIG. 5;
FIG. 8 is a chart illustrating the X-ray diffraction (2θ=25 to 27°) of an oxide catalyst before and after gas-phase catalytic oxidation reaction of olefin in Comparative Example A6;
FIG. 9 is a chart illustrating the X-ray diffraction peaks of catalysts obtained in Examples B1 and Comparative Example B1;
FIG. 10 is an enlarged chart illustrating the range of 2θ=15 to 30° in X-ray diffraction peaks in FIG. 9;
FIG. 11 is an enlarged chart illustrating the range of 2θ=30 to 50° in X-ray diffraction peaks in FIG. 9;
FIG. 12 is a chart illustrating the XRD (2θ=10 to 60°) of an oxide catalyst before and after gas-phase catalytic oxidation reaction of olefin in Example C1;
FIG. 13 is an enlarged chart illustrating the range of 2θ=25 to 27° in FIG. 12;
FIG. 14 is a chart illustrating the XRD (2θ=10 to 60°) of an oxide catalyst before and after gas-phase catalytic oxidation reaction of olefin in Comparative Example C1;
FIG. 15 is an enlarged chart illustrating the range of 2θ=25 to 27° in FIG. 14; and
FIG. 16 is a chart illustrating the X-ray diffraction peaks of catalysts obtained in Examples C1 and Comparative Example C2.

MODE FOR CARRYING OUT THE INVENTION

Hereinafter, the first to third embodiments for carrying out the present invention will be described in detail. The present invention is not intended to be limited to the embodiments described below, and various changes or modifications can be made therein without departing from the spirit of the present invention.

[First Embodiment]
[Oxide Catalyst]
The oxide catalyst according to the first embodiment will be described.
The oxide catalyst according to the first embodiment is
an oxide catalyst for use in the production of unsaturated aldehyde or diolefin from olefin and/or alcohol, the oxide catalyst satisfying the following (1) to (3)
(1) the oxide catalyst comprises molybdenum (hereinafter, also referred to as "Mo"), bismuth (hereinafter, also referred to as "Bi"), iron (hereinafter, also referred to as "Fe"), cobalt (hereinafter, also referred to as "Co"), and an element A having an ion radius larger than 0.96 Å (except for potassium, cesium, and rubidium);
(2) an atomic ratio a of the bismuth to 12 atoms of the molybdenum is 1≤a≤5, an atomic ratio b of the iron to 12 atoms of the molybdenum is 1.5≤b≤6, an atomic ratio c of the element A to 12 atoms of the molybdenum is 1≤c≤5, and an atomic ratio d of the cobalt to 12 atoms of the molybdenum is 1≤d≤8; and
(3) the oxide catalyst comprises a disordered phase consisting of a crystal system comprising the molybdenum, the bismuth, the iron, and the element A.

(Starting Material)
Examples of the olefin serving as a starting material for use in the production of unsaturated aldehyde or diolefin include, but not limited to, propylene, n-butene, isobutylene, n-pentene, n-hexene, and cyclohexene. Among them, propylene and isobutylene are preferred.
Examples of the alcohol serving as a starting material for use in the production of unsaturated aldehyde or diolefin include, but not limited to, propanol, isopropanol, butanol, isobutanol, and t-butyl alcohol. Among them, isobutanol and t-butyl alcohol are preferred.

In the first embodiment, for example, acrolein or acrylic acid can be produced using propylene, propanol, or isopropanol as a starting material, while methacrolein or methacrylic acid can be produced using isobutylene, isobutanol, or t-butyl alcohol as a starting material.

Alternatively, butadiene can be produced using n-butene as a starting material. The starting materials olefin and alcohol may contain water, nitrogen, and alkanes such as propane, butane, and isobutane.

These olefins and/or alcohols may be used alone or in combination.

(I) Composition

The oxide catalyst according to the first embodiment comprises molybdenum, bismuth, iron, cobalt, and the element A having an ion radius larger than 0.96 Å (except for potassium, cesium, and rubidium). The presence of Mo, Bi, and Fe is indispensable from the viewpoint of compositing the metal elements in a Bi—Mo catalyst in which Bi and Mo together form an active species.

The atomic ratio a of Bi to 12 Mo atoms is $1 \leq a \leq 5$. The atomic ratio a is preferably $1 \leq a \leq 4$, more preferably $1 \leq a \leq 3$, from the viewpoint of further enhancing the selectivity of unsaturated aldehyde and/or diolefin.

From the viewpoint of enhancing catalytic activity without reducing the selectivity of unsaturated aldehyde and/or diolefin, Fe is an essential element, as with Mo and Bi, for industrially synthesizing unsaturated aldehyde and/or diolefin. A large content of Fe, however, forms $Fe_2O_3$ and tends to increase by-products such as CO or $CO_2$, resulting in the reduced selectivity of unsaturated aldehyde and/or diolefin. Alternatively, a large content of Fe may not form $Fe_2O_3$, but instead forms a Fe—Mo—O 2-component composite oxide, which is an inactive component that exhibits no catalytic activity. From these points of view, the atomic ratio b of Fe to 12 Mo atoms in the oxide catalyst according to the first embodiment is $1.5 \leq b \leq 6$, preferably $1.5 \leq b \leq 5$, more preferably $1.5 \leq b \leq 4$.

Bi and Mo tend to form a composite oxide such as $Bi_2Mo_3O_{12}$ or $Bi_2MoO_6$, which is reportedly an active species in gas-phase catalytic oxidation, ammoxidation, oxidative dehydrogenation reaction, and the like. A catalyst consisting of such a composite oxide gives the high selectivity of unsaturated aldehyde or diolefin, but is low active. On the other hand, Fe and Mo form a composite oxide such as $Fe_2Mo_3O_{12}$. A catalyst consisting of such a composite oxide exhibits both low activity and low selectivity. Nonetheless, the appropriate compositing of Mo, Bi, and Fe forms a 3-component composite oxide comprising the disordered phase $Bi_3Fe_1Mo_2O_{12}$ with high activity and high selectivity of unsaturated aldehyde and diolefin.

The present inventors have conducted diligent studies to obtain an oxide catalyst excellent in heat resistance that retains the characteristic structure described above even at a high temperature, and consequently found that the heat resistance of the oxide catalyst is improved by the incorporation of element A having an ion radius larger than 0.96 Å except for potassium, cesium, and rubidium (hereinafter, also simply referred to as an "element A") into the structure of the oxide catalyst. Specifically, the present inventors have found that a disordered phase consisting of a crystal system comprising molybdenum, bismuth, iron, and element A is useful in improving heat resistance, when contained in the oxide catalyst.

Element A can be any element having an ion radius larger than 0.96 Å except for potassium, cesium, and rubidium without limitations. Examples of element A include: at least one element selected from the group consisting of lanthanoid elements such as cerium, praseodymium, neodymium, samarium, europium, gadolinium, terbium, and dysprosium, or a mixture thereof; at least one element selected from the group consisting of elements such as lead and yttrium, or a mixture thereof; and at least one element selected from the group consisting of alkaline earth metals such as calcium, strontium, and barium, or a mixture thereof. Among them, element A is preferably at least one element selected from the group consisting of lanthanum, cerium, praseodymium, neodymium, samarium, europium, gadolinium, terbium, dysprosium, calcium, and lead, or a mixture thereof, more preferably at least one element selected from the group consisting of lanthanum, cerium, praseodymium, neodymium, calcium, and lead, or a mixture thereof, from the viewpoint of the balance between stability and reactivity.

The atomic ratio c of element A to 12 Mo atoms is $1 \leq c \leq 5$, preferably $1 \leq c \leq 4$, more preferably $1 \leq c \leq 3$. Provided that the atomic ratio c falls within the range described above, a 4-component composite oxide comprising the disordered phase $Bi_{3-x}A_xFe_1Mo_2O_{12}$ is formed. For example, in the case of using La as element A, a 4-component composite oxide comprising the disordered phase $Bi_{3-x}La_xFe_1Mo_2O_{12}$ is formed. La can be appropriately composited into a 3-component composite oxide comprising the disordered phase $Bi_3Fe_1Mo_2O_{12}$ so that $Bi^{3+}$ (ion radius: 0.96 Å) is substituted by $La^{3+}$ having a larger ion radius to obtain an oxide catalyst that has heat resistance and has both high activity and high selectivity. A 3-component composite oxide free from $La^{3+}$ undergoes phase transition to an ordered phase at a high temperature of at least 500° C., whereas the coexistence therewith of La having a slightly larger ion radius than that of Bi inhibits the phase transition to an ordered phase and maintains the disordered phase structure. The element that exerts this inhibitory effect on the phase transition to an ordered phase is not limited to La, and any of the elements A listed above can exert similar effects.

Co is indispensable for imparting reduction resistance to the oxide catalyst according to the first embodiment. In the presence of Co, divalent iron is incorporated into $CoMoO_4$ to form a $Co^{2+}$—$Fe^{2+}$—Mo—O 3-component crystal structure. This incorporated iron is easily oxidized into trivalent iron in a reaction atmosphere, because of its metastable structure. Redox is therefore cycled during the reaction, presumably preventing reduction degradation.

Fe in $Fe_2Mo_3O_{12}$ or a 4-component composite oxide comprising the disordered phase $Bi_{3-x}A_xFe_1Mo_2O_{12}$ is trivalent immediately after the start of reaction, but is reduced into divalent iron through redox cycles during the reaction. In the absence of Co, a composite oxide of divalent iron and molybdenum ($FeMoO_4$) and $MoO_2$ are formed. This $FeMoO_4$ is rarely rendered trivalent in a reaction atmosphere, because of its stable structure. The formation of these stable compounds stabilizes iron so that redox is not cycled during the reaction, presumably causing reduction degradation.

The atomic ratio d of Co to 12 Mo atoms is $1 \leq d \leq 8$, preferably $2 \leq d \leq 8$, more preferably $2 \leq d \leq 6$, further preferably $3 \leq d \leq 5$. At the atomic ratio d exceeding 8, a 4-component composite oxide comprising the disordered phase $Bi_{3-x}A_xFe_1Mo_2O_{12}$ is difficult to form.

(2) Crystal Structure

The oxide catalyst according to the first embodiment preferably contains a 4-component composite oxide comprising the disordered phase $Bi_{3-x}A_xFe_1Mo_2O_{12}$. X-ray diffraction (XRD) can be used as an index for the formation of the 4-component composite oxide comprising the disordered phase $Bi_{3-x}A_xFe_1Mo_2O_{12}$. The oxide catalyst according to the first embodiment preferably has single peaks at least in 18.30°±0.2° (101), 28.20°±0.2° (112), 33.65°±0.2° (200), and 46.15°±0.2° (204) planes measured in the range of diffraction angles 2θ=10° to 60° in crystal X-ray diffraction, as in the 3-component composite oxide comprising the disordered phase $Bi_3Fe_1Mo_2O_{12}$. Particularly preferably, the oxide catalyst according to the first embodiment has a single peak at a position within each reference value ±0.05°.

The intensity ratio (Ia/Ib) of intensity (Ia) of peak a at 2θ=33.65°±0.2° to intensity (Ib) of peak b at 2θ=34.10°±0.2° is preferably 2.0 or larger, more preferably 2.5 or larger, further preferably 3.0 or larger, from the viewpoint of further preventing catalyst decomposition and obtaining unsaturated aldehyde and/or diolefin at higher yields. The intensity ratio (Ia/Ib) is 1.1 in 100% ordered phase and is 3.3 in 100% disordered phase. The intensity (Ib) of peak b at 2θ=34.10°±0.2° also comprises peak intensity derived from $Fe_2Mo_3O_{12}$ present in a trace amount. At the intensity ratio (Ia/Ib) of 2.0 or larger, the oxide catalyst contains a predetermined proportion of the disordered phase and therefore gives the reduced yield of unsaturated carboxylic acid and the improved yield of unsaturated aldehyde and/or diolefin. FIG. 4 shows the relationship of the content of the disordered phase with the peaks a and b.

The mechanism under which the disordered phase $Bi_{3-x}A_xFe_1Mo_2O_{12}$ is formed is uncertain. A composite oxide of Bi and Mo is formed as an intermediate in a heat treatment step. Further heat treatment probably causes thermal diffusion and substitutional solid solution of Fe and element A into the composite oxide of Bi and Mo to form a composited disordered phase $Bi_{3-x}A_xFe_1Mo_2O_{12}$.

(Single Peak)

The term "single peak" described herein should not be understood in a strict sense, and a main peak detected at each diffraction angle can be understood as a single peak unless split. This means that even a peak having an inflection point can be regarded as a single peak. An evidently smaller peak than a main peak is excluded if present, and then, the main peak is desirably determined to be a single or split peak. The "smaller peak" refers to a peak having intensity less than 50% of that of the main peak in a predetermined diffraction angle range.

The "main peak" refers to the largest peak among peaks present in a predetermined diffraction angle range. For example, as for a diffraction angle in the range of 18.30°±0.2°, the largest peak may be detected at a position of 18.35°. In such a case, this peak is determined as a main peak at 18.30°±0.2°.

The oxide catalyst according to the first embodiment preferably has a composition represented by the composition formula (1) shown below. The oxide catalyst having composition represented by the composition formula (1) shown below tends to prevent the formation of unsaturated carboxylic acid or carbon dioxide and further improve the selectivity of unsaturated aldehyde and/or diolefin.

Composition formula (1)

$$Mo_{12}Bi_aFe_bA_cCo_dB_eC_fO_g \quad (1)$$

wherein Mo represents molybdenum; Bi represents bismuth; Fe represents iron; element A represents an element having an ion radius larger than 0.96 Å (except for potassium, cesium, and rubidium); Co represents cobalt; element B represents at least one element selected from the group consisting of magnesium, zinc, copper, nickel, manganese, chromium, and tin; element C represents at least one element selected from the group consisting of potassium, cesium, and rubidium; a to g each represent the atomic ratio of each element to 12 Mo atoms wherein the atomic ratio a of Bi is 1≤a≤5, the atomic ratio b of Fe is 1.5≤b≤6, the atomic ratio c of element A is 1≤c≤5, the atomic ratio d of Co is 1≤d≤8, the atomic ratio e of element B is 0≤e≤3, the atomic ratio f of element C is 0≤f≤2, and the ratio of Fe/Co is 0.8≤b/d; and g represents the atomicity of oxygen determined by the valences of constituent elements other than oxygen.

In the composition formula (1), element B represents at least one element selected from the group consisting of magnesium, zinc, copper, nickel, manganese, chromium, and tin and presumably substitutes some cobalt atoms in the oxide catalyst. The atomic ratio e of element B is preferably 0≤e<3, more preferably 0≤e<2, from the viewpoint of keeping the balance with the formation of crystals of the disordered phase. Element B is not essential, but contributes to improvement in the activity of the catalyst or the stabilization of the crystal structure of $CoMoO_4$ in the catalyst. For example, copper has the effect of improving the activity of the catalyst. Nickel, magnesium, zinc, and manganese have the effects of stabilizing the crystal structure of $CoMoO_4$ and inhibiting, for example, phase transition attributed to pressure or temperature.

In the oxide catalyst according to the first embodiment, Co is an essential element, as with Mo, Bi, and Fe, from the viewpoint of industrially synthesizing unsaturated aldehyde and/or diolefin. Co plays a role as a carrier for forming the composite oxide $CoMoO_4$ and highly dispersing active species such as Bi—Mo—O and also plays a role in taking up oxygen from the gas phase and supplying this oxygen to Bi—Mo—O or the like. Co and Mo are preferably composited to form a composite oxide $CoMoO_4$, from the viewpoint of obtaining unsaturated aldehyde and/or diolefin at high yields. The atomic ratio d of Co is preferably 1≤d≤8, more preferably 2≤d≤8, further preferably 2≤d≤7, still further preferably 2≤d≤5, from the viewpoint of reducing the formation of unary oxides such as $Co_3O_4$ or CoO.

The ratio of Fe/Co is preferably 0.8≤b/d, more preferably 0.8≤b/d≤1.5, further preferably 0.9≤b/d≤1.2. Provided that the ratio of Fe/Co falls within the range described above, unary oxides such as $Co_3O_4$ or CoO tends to be rarely formed.

Element A represents an element having an ion radius larger than 0.96 Å except for potassium, cesium, and rubidium. The atomic ratio c of element A is preferably 1≤c≤5, more preferably 1≤c≤4, further preferably 1≤c≤3.

Element C represents at least one element selected from the group consisting of potassium, cesium, and rubidium. Element C probably plays a role in neutralizing the acid center of uncomposited $MoO_3$ or the like in the oxide catalyst. The presence or absence of element C contained therein does not directly influence the crystal structure of the disordered phase described later. The atomic ratio f of element C to 12 Mo atoms is preferably 0≤f≤2, more preferably 0.01≤f≤2, further preferably 0.01≤f≤1, from the viewpoint of catalytic activity. At the atomic ratio f of 0 or larger, the neutralizing effect tends to be further improved. At the atomic ratio f of 2 or smaller, the oxide catalyst tends to be rendered basic to neutral. The resulting oxide catalyst easily adsorbs the starting material olefin or alcohol and tends to exhibit higher catalytic activity.

The oxide catalyst may contain arbitrary components as other metal components without inhibiting the formation of the disordered phase $Bi_{3-x}A_xFe_1Mo_2O_{12}$.

Element B and element C form crystal structures separately from the crystal structure of the disordered phase described later and therefore, do not directly influence the crystal structure of the disordered phase.

(3) Component other than Metal Oxide

The oxide catalyst according to the first embodiment may further comprise a carrier for supporting the metal oxide. The catalyst further comprising the carrier is preferred because of highly dispersing the metal oxide and imparting high wear resistance to the supported metal oxide. In this context, the catalyst preferably comprises the carrier when molded by an extrusion molding method. Alternatively, a catalyst tablet-compressed for the production of methacrolein in a fixed-bed reactor may not have to comprise the carrier.

Examples of the carrier include, but not limited to, at least one selected from the group consisting of silica, alumina, titania, and zirconia. The oxide catalyst supported by such a carrier tends to have further improvement in physical properties suitable for fluidized-bed reaction, such as particle shape, size, distribution, flowability, and mechanical strength. Among them, silica is preferred as the carrier. In general, the silica carrier is preferred in terms of its property of imparting the physical properties suitable for fluidized-bed reaction to the oxide catalyst as well as because of being inactive compared with other carriers and having favorable binding effect on the metal oxide without reducing selectivity to unsaturated aldehyde and/or diolefin. In addition, the silica carrier is also preferred because of easily imparting high wear resistance to the metal oxide supported thereby.

A silica sol is preferred as a silica source. The concentration of the silica sol in the state of a starting material unmixed with other components is preferably 10 to 50% by mass from the viewpoint of the dispersibility of silica particles. The silica sol preferably comprises 40 to 100% by mass of at least one silica sol (a) containing primary silica particles having an average particle diameter of 20 nm to smaller than 55 nm, preferably 20 to 50 nm, and 60 to 0% by mass of at least one silica sol (b) containing primary silica particles having an average particle diameter of 5 nm to smaller than 20 nm, from the viewpoint of the selectivity of unsaturated nitrile.

The content of the carrier is preferably 20 to 80% by mass, more preferably 30 to 70% by mass, further preferably 40 to 60% by mass, still further preferably 5 to 10% by mass, with respect to 100% by mass in total of the carrier and the oxide catalyst. Setting the content of the carrier falls within the range described above, the yield of unsaturated aldehyde and/or diolefin tends to be further improved.

(4) Molding of Oxide Catalyst

The oxide catalyst of the first embodiment may be molded for use. In such a case, the molding is performed by a method known in the art such as tablet compression or extrusion molding. Examples of shapes into which the oxide catalyst is molded include tablets, pellets, spheres, computer designed shapes (CDSs), trilobes, quadrilobes, rings, high geometric surfaces (HGSs), cloverleaf shapes, and honeycomb shapes. Among them, CDSs and rings are preferred from the viewpoint of strength.

The specific surface area of the oxide catalyst is preferably 2 to 5 $m^2/g$, more preferably 2 to 4 $m^2/g$. In the case of using the carrier such as silica, the specific surface area tends to be larger than 2 to 5 $m^2/g$. The specific surface area of the carrier-free metal oxide alone is preferably 2 to 5 $m^2/g$.

[2] Method for Producing Oxide Catalyst

As mentioned above, the present inventors have focused on the obtainment of the disordered phase $Bi_{3-x}A_xFe_1Mo_2O_{12}$ comprising element A, Bi, Fe, and Mo, and comprehensively studied the compositional ratios of the elements and a method for preparing the disordered phase.

As is evident from the name Bi—Mo catalyst, both Bi and Mo are essential elements for forming an active species. A catalyst rich in Bi and Mo is advantageous from the viewpoint of activity. A large content of Bi, however, has been shown to make the catalyst inhomogeneous. For example, bismuth nitrate, which is a conventional Bi source industrially used, is a poorly water-soluble substance and therefore requires a large amount of nitric acid for its dissolution. As a result, the catalyst has inhomogeneous composition after calcination. In this regard, the Bi content is limited within in a range in the conventional technique of preparing catalysts. This fails to yield a homogeneous catalyst due to formed unary oxides such as $Bi_2O_3$, resulting in unfavorable decrease in the yield of unsaturated aldehyde and/or diolefin.

From the viewpoint of enhancing catalytic activity without reducing the selectivity of unsaturated aldehyde and/or diolefin, Fe has been previously reported to be an essential element, as with Mo and Bi, for industrially synthesizing unsaturated aldehyde and/or diolefin. As reported by International Publication No. WO 95/35273, however, a large amount of Fe added tends to increase by-products such as CO or $CO_2$, resulting in the reduced selectivity of unsaturated aldehyde and/or diolefin. Fe is therefore optimally added in a small amount.

After much trial and error to solve this problem, the present inventors have found that crystals of the disordered phase $Bi_{3-x}A_xFe_1Mo_2O_{12}$ can be easily formed with the formation of an ordered phase suppressed by a method for producing an oxide catalyst described later.

The method for producing the oxide catalyst according to the first embodiment comprises:

a mixing step of mixing starting materials constituting the catalyst, comprising molybdenum, bismuth, iron, cobalt, and element A having an ion radius larger than 0.96 Å (except for potassium, cesium, and rubidium), to obtain slurry;

a drying step of drying the slurry thus obtained to obtain a dried product; and a calcination step of calcining the dried product thus obtained, wherein the calcination step comprises a heating step of gradually heating the dried product from 100° C. to 200° C. over 1 hour or longer.

(1) Mixing Step

The mixing step is a step of mixing starting materials of metal elements constituting the catalyst, comprising molybdenum, bismuth, iron, cobalt, and element A having an ion radius larger than 0.96 Å (except for potassium, cesium, and rubidium), to obtain slurry. Examples of sources of molybdenum, bismuth, iron, cobalt, element A, rubidium, cesium, potassium, magnesium, copper, nickel, chromium, manganese, lead, alkaline earth metals, and rare earth elements include these element in the forms of ammonium salt, nitrate, hydrochloride, organic acid salts, oxides, hydroxides, and carbonate, which are soluble in water or nitric acid.

In the case of using an oxide of each element source, a dispersion containing the oxide dispersed in water or an organic solvent is preferably used, and an oxide dispersion containing the oxide dispersed in water is more preferably used. The dispersion of the oxide in water may further contain a dispersion stabilizer such as a polymer for dispersing the oxide. The particle size of the oxide is preferably 1 to 500 nm, more preferably 10 to 80 nm.

The slurry may be appropriately supplemented with: water-soluble polymers such as polyethylene glycol, methylcellulose, polyvinyl alcohol, polyacrylic acid, and polyacrylamide; polyvalent carboxylic acids such as amines, aminocarboxylic acids, oxalic acid, malonic acid, and succinic acid; and/or organic acids such as glycolic acid, malic acid, tartaric acid, and citric acid, from the viewpoint of uniformly dispersing the catalyst starting materials into the slurry. The amount of the water-soluble polymer and/or the organic acid added is, but not limited to, preferably 30% by mass or lower with respect to 100% by mass of the catalyst starting materials from the viewpoint of the balance between uniformity and yields.

The slurry may be prepared by any method usually used without limitations and can be prepared, for example, by mixing a solution containing ammonium salt of molybdenum dissolved in hot water, with solutions containing nitrates of metal components other than molybdenum, such as bismuth, iron, cobalt, and element A, dissolved in water or these metal components dissolved in an aqueous nitric acid solution. In the case of the oxide catalyst comprising a carrier, for example, a silica sol can be added before or after the mixing of a solution containing ammonium salt of molybdenum dissolved in hot water, with solutions containing metal components other than molybdenum dissolved in water or an aqueous nitric acid solution. The slurry thus mixed has a metal element concentration of usually 1 to 50% by mass, preferably 10 to 40% by mass, more preferably 20 to 40% by mass, with respect to 100% by mass of the slurry from the viewpoint of the balance between uniformity and yields.

The step of preparing the slurry described above is provided for an illustrative purpose and is not intended to limit the technical scope of the present invention. The order in which the element sources are added may be changed, or the pH or viscosity of the slurry may be changed by the adjustment of the nitric acid concentration or by the addition of ammonia water into the slurry. Preferably, the slurry is homogeneous for forming the crystal structure of the disordered phase $Bi_{3-x}A_xFe_1Mo_2O_{12}$. From this point of view, the pH of the slurry is preferably 8.0 or lower, more preferably 7.0 or lower, further preferably 6.0 or lower. The slurry having a pH of 8.0 or lower can prevent the precipitation of bismuth compounds and tends to promote the formation of the crystal structure of the disordered phase $Bi_{3-x}A_xFe_1Mo_2O_{12}$.

(2) Drying Step

The drying step is a step of drying the slurry obtained in the mixing step to obtain a dried product. The drying may be performed by any method generally used without limitations. Examples of the drying method include arbitrary methods such as evaporation to dryness, spray drying, and drying under reduced pressure. Examples of the spray drying method include, but not limited to, usual methods such as centrifugation systems, two-fluid nozzle systems, and high-pressure nozzle systems, which are industrially carried out. In this drying, air heated with steam, an electrical heater, or the like is preferably used as a dry heat source. The temperature at the dryer inlet of the spray drying apparatus is usually 150 to 400° C., preferably 180 to 400° C., more preferably 200 to 350° C.

(3) Calcination Step

The calcination step is a step of calcining the dried product obtained in the drying step. The calcination can be performed using a kiln such as a rotary furnace, a tunnel furnace, or a muffle furnace. The calcination step comprises a heating step of gradually heating the dried product from 100 to 200° C. over 1 hour or longer. Through this heating step, 4 component elements Bi, Mo, Fe, and element A can be uniformly mixed at the atomic level to easily form the crystal structure of the disordered phase $Bi_{3-x}A_xFe_1Mo_2O_{12}$. The term "gradually heating" described herein refers to heating to a predetermined temperature usually over 1 h to 10 h as a heating time. The rate of heating does not have to be kept constant. The heating time is usually 1 h to 10 h, preferably 1 h to 5 h, more preferably 2 h to 4 h.

The method for calcining the dried product differs depending on the starting materials used. For example, a dried product from starting materials comprising nitric acid ions is preferably calcined at two stages of preliminary calcination and final calcination. Specifically, the calcination is preferably performed by: a preliminary calcination step of preliminarily calcining the dried product at a temperature of 200 to 300° C. to obtain a preliminarily calcined product; and a final calcination step of finally calcining the preliminarily calcined product thus obtained at a temperature of 300° C. or higher to obtain the catalyst. The heating step is performed before the preliminary calcination step, and then, the temperature is raised to the range of 200° C. to 300° C. usually over 1 h or longer.

The preliminary calcination step involves calcining the dried product at a temperature ranging from 200° C. to 300° C. The preliminary calcination time is usually 1 h to 10 h, preferably 2 h to 8 h, more preferably 3 h to 6 h. The preliminary calcination is performed for the purpose of causing gradual combustion of nitric acid remaining in the dried product. The preliminary calcination tends to form the homogeneous crystal structure of the disordered phase $Bi_{3-x}A_xFe_1Mo_2O_{12}$. In this context, preliminary calcination in a temperature range of 200° C. to 300° C. directly performed without the heating step from 100 to 200° C. rarely forms the crystal structure of the disordered phase $Bi_{3-x}A_xFe_1Mo_2O_{12}$ and might instead form an ordered phase or 2-component oxides such as $Fe_2Mo_3O_{12}$, $Bi_2Mo_3O_{12}$, or $A_2Mo_3O_{12}$.

The preliminarily calcined product thus obtained by the preliminary calcination is finally calcined at the 2nd stage in order to facilitate the formation of the crystal structure of the disordered phase. According to the findings gained by the present inventors, the formation of the crystal structure depends on the product of the calcination temperature and the calcination time. Preferably, the calcination temperature and the calcination time are appropriately set. The final calcination temperature is higher than the preliminary calcination temperature and is preferably 300° C. or higher, more preferably 300° C. or higher and 700° C. or lower, further preferably 300 to 650° C., still further preferably 400° C. to 600° C., particularly preferably 450° C. to 600° C. Setting the final calcination temperature falls within the range described above, the crystal structure of the disordered phase $Bi_{3-x}A_xFe_1Mo_2O_{12}$ tends to be more easily formed.

In the case of final calcination at such a temperature, the final calcination time is usually 0.1 to 72 hours, preferably 2 to 48 hours, more preferably 3 to 24 hours, from the viewpoint of appropriately setting the product of the calcination temperature and the calcination time and promoting the formation of crystals.

For forming the crystal structure, the final calcination time is preferably, for example, 24 to 72 hours at a final calcination temperature as low as at least 400° C. from the viewpoint of appropriately setting calcination temperature x calcination time, and is preferably 3 hours or shorter at a final calcination temperature as high as at least 600° C. from the viewpoint of preventing the formation of an ordered phase.

The crystal structure of the disordered phase $Bi_{3-x}A_xFe_1Mo_2O_{12}$ can be easily formed by performing all of these steps.

The successful formation of the crystal structure of the disordered phase $Bi_{3-x}A_xFe_1Mo_2O_{12}$ in the final calcination step can be confirmed by X-ray structural analysis on the oxide catalyst obtained by the final calcination. Provided that the oxide catalyst according to the first embodiment has single peaks at diffraction angles (2θ) at least in the each range of 18.30°±0.2° (101), 28.20°±0.2° (112), 33.65°±0.2° (200), and 46.15°±0.2° (204) planes in the X-ray diffraction analysis and that the intensity ratio (Ia/Ib) of the peak intensity (Ia) at 2θ=33.65°±0.2° to the peak intensity (Ib) at 2θ=34.10°±0.2° is 2.0 or larger, it can be determined that the crystal structure of the disordered phase $Bi_{3-x}A_xFe_1Mo_2O_{12}$ has been formed.

[3] Method for Producing Unsaturated Aldehyde

Unsaturated aldehyde can be produced through the oxidation reaction of at least one olefin selected from the group consisting of propylene and isobutylene and/or at least one alcohol selected from isobutanol and t-butyl alcohol using the oxide catalyst according to the first embodiment. Hereinafter, specific examples of the method will be described, though the method for producing unsaturated aldehyde is not limited to the specific examples below.

(1) Method for Producing Methacrolein

Methacrolein can be obtained, for example, through the gas-phase catalytic oxidation reaction of isobutylene, isobutanol, or t-butyl alcohol using the oxide catalyst according to the first embodiment. The gas-phase catalytic oxidation reaction can be performed by the introduction, into a catalyst layer in a fixed-bed reactor, of feed gas composed of 1 to 10% by volume of isobutylene, isobutanol, t-butyl alcohol, or a mixed gas thereof supplemented with molecular oxygen-containing gas and diluent gas at a molecular oxygen concentration of 1 to 20% by volume in the presence of the oxide catalyst. This reaction can be performed at a temperature of 250 to 480° C., a pressure of ordinary pressure to 5 atm, and a space velocity of 400 to 4000/hr [under normal temperature pressure (NTP) conditions]. The molar ratio of oxygen to isobutylene, isobutanol, t-butyl alcohol, or a mixed gas thereof (oxygen/isobutylene, isobutanol, t-butyl alcohol, or mixed gas thereof) is usually 1.0 to 2.0, preferably 1.1 to 1.8, more preferably 1.2 to 1.8, from the viewpoint of controlling the oxygen concentration at the reactor outlet in order to improve the yield of unsaturated aldehyde.

Examples of the molecular oxygen-containing gas include, but not limited to, oxygen-containing gases such as pure oxygen gas, $N_2O$, and air. Among them, air is preferred from an industrial standpoint.

Examples of the diluent gas include, but not limited to, nitrogen, carbon dioxide, water vapor, and mixed gases thereof. The mixing ratio between the molecular oxygen-containing gas and the diluent gas is preferably 0.01<molecular oxygen/(molecular oxygen-containing gas+diluent gas) <0.3 by volume. The content of the molecular oxygen is preferably 1 to 20% by volume with respect to 100% by volume of the feed gas.

Water vapor in the feed gas is effective in preventing catalyst coking. By contrast, the concentration of water vapor in the diluent gas is preferably decreased as much as possible in order to inhibit the formation of carboxylic acid by-products such as methacrylic acid or acetic acid. The content of the water vapor is usually 0 to 30% by volume with respect to 100% by volume of the feed gas.

(2) Method for Producing Acrolein

Acrolein may be produced through the gas-phase catalytic oxidation of propylene, for example, under any condition without limitations and can be produced by a method generally used for producing acrolein through the gas-phase catalytic oxidation of propylene. For example, a mixed gas containing 1 to 15% by volume of propylene, 3 to 30% by volume of molecular oxygen, 0 to 60% by volume of water vapor, and 20 to 80% by volume of inert gas such as nitrogen and $CO_2$ gas can be introduced at 250 to 450° C. under pressure of 0.1 to 1 MPa at a space velocity (SV) of 300 to 5000 $hr^{-1}$ to a catalyst layer in a reactor. The reactor used can be a general fixed-bed reactor, fluidized-bed reactor, or moving-bed reactor.

(3) Method for Producing Diolefin

The method for producing diolefin according to the first embodiment comprises a diolefin production step of oxidizing monoolefin having 4 or more carbon atoms using the oxide catalyst according to the first embodiment to obtain the diolefin. More specifically, the diolefin production step is a step of obtaining the diolefin through the gas-phase catalytic oxidation reaction of monoolefin having 4 or more carbon atoms with an oxygen source in the presence of the oxide catalyst according to the first embodiment.

The oxygen source used in the gas-phase catalytic oxidation reaction can be, but not limited to, for example, a mixed gas of molecular oxygen-containing gas and diluent gas.

Examples of the monoolefin having 4 or more carbon atoms include, but not limited to, n-butene.

The obtained diolefin differs depending on the monoolefin having 4 or more carbon atoms used. For example, butadiene is obtained using n-butene.

Examples of the molecular oxygen-containing gas include, but not limited to, oxygen-containing gases such as pure oxygen gas and air. Among them, air is preferably used as the molecular oxygen-containing gas. Use of the air tends to be excellent from an industrial standpoint such as cost.

Examples of the diluent gas include, but not limited to, nitrogen, carbon dioxide, water vapor, and mixed gases thereof.

The feed gas to be supplied to the diolefin production step is preferably supplemented with molecular oxygen-containing gas and diluent gas at monoolefin having 4 or more carbon atoms concentration of 1 to 10% by volume and a molecular oxygen concentration of 1 to 20% by volume.

Examples of the reactor include, but not limited to, fixed-bed reactors. The reaction can be performed at a temperature of preferably 250 to 450° C., a pressure of preferably ordinary pressure to 5 atm, and a space velocity of preferably 400 to 4000/hr [under normal temperature pressure (NTP) conditions].

[Second Embodiment]

The oxide catalyst according to the second embodiment (hereinafter, also referred to as an "ammoxidation catalyst") will be described.

The oxide catalyst according to the second embodiment is an oxide catalyst for use in the production of unsaturated nitrile from olefin and/or alcohol, the oxide catalyst satisfying the following (1) to (3):

(1) the oxide catalyst comprises molybdenum, bismuth, iron, cobalt, and an element A having an ion radius larger than 0.96 Å (except for potassium, cesium, and rubidium);

(2) an atomic ratio a of the bismuth to 12 atoms of the molybdenum is $1 \leq a \leq 5$, an atomic ratio b of the iron to 12 atoms of the molybdenum is $1.5 \leq b \leq 6$, an atomic ratio c of the element A to 12 atoms of the molybdenum is $1 \leq c \leq 5$, and an atomic ratio d of the cobalt to 12 atoms of the molybdenum is $1 \leq d \leq 8$; and (3) the oxide catalyst comprises a disordered phase consisting of a crystal system comprising the molybdenum, the bismuth, the iron, and the element A.

(Starting Material)

Examples of the olefin serving as a starting material for use in the production of unsaturated nitrile include, but not limited to, propylene, n-butene, isobutylene, n-pentene, n-hexene, and cyclohexene. Among them, propylene and isobutylene are preferred.

Examples of the alcohol serving as a starting material for use in the production of unsaturated nitrile include, but not limited to, propanol, butanol, isobutanol, and t-butyl alcohol. Among them, isobutanol and t-butyl alcohol are preferred.

In the second embodiment, for example, acrylonitrile can be produced using propylene or propanol as a starting material, while methacrylonitrile can be produced using isobutylene, isobutanol, or t-butyl alcohol as a starting material.

These olefins and/or alcohols may be used alone or in combination.

Examples of the unsaturated nitrile include, but not limited to, acrylonitrile and methacrylonitrile.

(1) Composition

The oxide catalyst according to the second embodiment comprises molybdenum, bismuth, iron, cobalt, and element A having an ion radius larger than 0.96 Å (except for potassium, cesium, and rubidium). The presence of Mo, Bi, and Fe is indispensable from the viewpoint of compositing the metal elements in a Bi—Mo catalyst in which Bi and Mo together form an active species.

The atomic ratio a of Bi to 12 Mo atoms is $1 \leq a \leq 5$, preferably $1 \leq a \leq 4$, more preferably $2 \leq a \leq 4$. Provided that the atomic ratio a of Bi falls within the range described above, the selectivity of unsaturated nitrile tends to be further improved.

From the viewpoint of enhancing catalytic activity without reducing the selectivity of unsaturated nitrile, Fe is an essential element, as with Mo and Bi, for industrially synthesizing unsaturated nitrile. A large content of Fe, however, forms $Fe_2O_3$ and tends to increase by-products such as CO or $CO_2$, resulting in the reduced selectivity of unsaturated nitrile. Alternatively, a large content of Fe may not form $Fe_2O_3$, but instead forms a $Fe_2Mo_3O_{12}$ 2-component composite oxide, which is an inactive component that exhibits no catalytic activity. From these points of view, the atomic ratio b of Fe to 12 Mo atoms in the ammoxidation catalyst according to the second embodiment is preferably $1.5 \leq b \leq 6$, more preferably $2.0 \leq b \leq 5$, further preferably $3 \leq b \leq 5$.

Bi and Mo tend to form composite oxides such as $Bi_2Mo_3O_{12}$ and $Bi_2MoO_6$, which are reportedly active species in ammoxidation reaction. A catalyst consisting of such a composite oxide tends to give the high selectivity of unsaturated nitrile, but be low active. On the other hand, Fe and Mo form a composite oxide such as $Fe_2Mo_3O_{12}$. A catalyst consisting of such a composite oxide exhibits both low activity and low selectivity. The compositing of Mo, Bi, and Fe forms the ordered phase $Bi_3Fe_1Mo_2O_{12}$. Industrial ammoxidation reaction for a long time using a catalyst having this structure has been shown to reduce the activity of the catalyst due to reduction during the reaction, resulting in the reduced yield of unsaturated nitrile, though initial yields are high. The present inventors have hypothesized the reason for this reduction degradation as follows: iron contained in $Bi_3Fe_1Mo_2O_{12}$ is in a trivalent state immediately after the start of reaction, but is reduced into divalent iron through redox cycles during the reaction to form a composite oxide of divalent iron and molybdenum ($FeMoO_4$). Also, Mo or Bi forms $MoO_2$, $Bi_2O_3$, or metal Bi. The formation of these stable compounds stabilizes iron so that redox is not cycled during the reaction, presumably causing reduction degradation.

The present inventors have conducted diligent studies on an oxide catalyst excellent in reduction resistance that retains the structure described above even in a highly reductive atmosphere, and consequently found that: the disordered phase $Bi_{3-x}A_xFe_1Mo_2O_{12}$ is formed by the further incorporation of element A having an ion radius larger than 0.96 Å into the structure of an oxide catalyst having 3 components of Mo, Bi, and Fe; and the resulting oxide catalyst has the improved reduction resistance. The 4-component composite oxide having this structure is highly active and gives the high selectivity of unsaturated nitrile. In addition, this composite oxide has been shown to have reduction resistance without forming, even during operation for a long time, the stable composite oxide of divalent iron and molybdenum ($FeMoO_4$) responsible for the reduction degradation. Specifically, as a result of compositing these 3 components (Mo, Bi, and Fe) with element A, element A and Fe cause redox during the reaction. Fe is therefore present in a slightly reduced form (e.g., $Fe^{3-\delta}$) compared with trivalent Fe, without being completely rendered divalent. Accordingly, redox is easily achieved, presumably resulting in the prevention of reduction degradation.

Element A can be any element having an ion radius larger than 0.96 Å except for potassium, cesium, and rubidium without limitations. Examples of element A include: at least one element selected from the group consisting of lanthanoid elements consisting of cerium, praseodymium, neodymium, samarium, europium, gadolinium, terbium, and dysprosium, or a mixture thereof; at least one element selected from the group consisting of elements tin, lead, and yttrium, or a mixture thereof; and at least one element selected from the group consisting of alkaline earth metals calcium, strontium, and barium, or a mixture thereof. Element A is preferably at least one element selected from the group consisting of lanthanum, cerium, praseodymium, neodymium, samarium, europium, gadolinium, terbium, dysprosium, calcium, and lead, or a mixture thereof, more preferably at least one element selected from the group consisting of lanthanum, cerium, praseodymium, neodymium, calcium, and lead, or a mixture thereof, from the viewpoint of the balance between stability and reactivity.

The atomic ratio c of element A to 12 molybdenum atoms is $1 \leq c \leq 5$, preferably $1 \leq c \leq 4$, more preferably $1.5 \leq c \leq 3$. Provided that the atomic ratio c falls within the range described above, a 4-component composite oxide comprising the composited disordered phase $Bi_{3-x}A_xFe_1Mo_2O_{12}$ is easily formed. For example, in the case of using La as element A, a 4-component composite oxide comprising the disordered phase $Bi_{3-x}La_xFe_1Mo_2O_{12}$ is formed. La can be appropriately composited into a 3-component composite oxide comprising the disordered phase $Bi_3Fe_1Mo_2O_{12}$ so that $Bi^{3+}$ (ion radius: 0.96 Å) is substituted by $La^{3+}$ having a larger ion radius to obtain an ammoxidation catalyst that has high activity and selectivity as well as reduction resistance. In the absence of $La^{3+}$, the ordered phase $Bi_3Fe_1Mo_2O_{12}$ is decomposed into $FeMoO_4$, $MoO_2$, $Bi_2O_3$, or metal Bi due to reduction by reaction gas in industrial operation for a long time. By contrast, the coexistence therewith of La having a slightly larger ion radius than that of Bi causes the redox between Fe and La, which in turn inhibits the decomposition attributed to reduction by reaction gas. In addition, the structure of the disordered phase $Bi_{3-x}La_xFe_1Mo_2O_{12}$ maintained without being decomposed into $FeMoO_4$, $MoO_2$, $Bi_2O_3$, or metal Bi.

In this context, the ion radius is described in, for example, "Chemistry of Ceramics", ed., by Hiroaki Yanagida, p. 14-17, Maruzene Co., Ltd.

(2) Crystal Structure

The ammoxidation catalyst according to the second embodiment preferably contains a 4-component composite oxide comprising the disordered phase $Bi_{3-x}A_xFe_1Mo_2O_{12}$. X-ray diffraction (XRD) can be used as an index for the formation of the 4-component composite oxide comprising the disordered phase $Bi_{3-x}A_xFe_1Mo_2O_{12}$. Provided that the 4-component composite oxide comprising the disordered phase $Bi_{3-x}A_xFe_1Mo_2O_{12}$ has been formed, the ammoxidation catalyst according to the second embodiment can be confirmed to have single peaks at least in 18.30°±0.2° (101), 28.20°±0.2° (112), 33.65°±0.2° (200), and 46.15°±0.2° (204) planes measured in the range of diffraction angles 2θ=10° to 60° in crystal X-ray diffraction, as in the 3-component composite oxide comprising the disordered phase $Bi_3Fe_1Mo_2O_{12}$. Particularly preferably, the ammoxidation catalyst according to the second embodiment has a single peak at a position within each reference value ±0.05°.

The intensity ratio (Ia/Ib) of intensity (Ia) of peak a at 2θ=33.65°±0.2° to intensity (Ib) of peak b at 2θ=34.10°±0.2° is preferably 2.0 or larger, more preferably 2.5 or larger, further preferably 3.0 or larger, from the viewpoint of preventing the reduction degradation of the catalyst. The intensity ratio (Ia/Ib) is 1.1 in 100% ordered phase and is 3.3 in 100% disordered phase. The intensity (Ib) of peak b at 2θ=34.10°±0.2° also comprises peak intensity Ib derived from $Fe_2Mo_3O_{12}$ present in a trace amount. At the intensity ratio (Ia/Ib) of 2.0 or larger, the oxide catalyst contains a predetermined proportion of the disordered phase and is therefore less susceptible to reduction degradation in industrial operation for a long time. Thus, the yield of unsaturated nitrile tends to be further improved. FIG. 4 shows the relationship of the content of the disordered phase with peaks a and b.

The mechanism under which the disordered phase $Bi_{3-x}A_xFe_1Mo_2O_{12}$ is formed is uncertain. A composite oxide of Bi and Mo is formed as an intermediate in a heat treatment step. Further heat treatment probably causes thermal diffusion and substitutional solid solution of Fe and element A into the composite oxide of Bi and Mo to form a composited disordered phase $Bi_{3-x}A_xFe_1Mo_2O_{12}$.

The "single peak" and the "main peak" are as defined in the first embodiment.

The ammoxidation catalyst according to the second embodiment preferably comprises a metal oxide having composition represented by the composition formula (2) shown below. The ammoxidation catalyst comprising a metal oxide having composition represented by the composition formula (2) shown below tends to improve the selectivity of unsaturated nitrile.

$$Mo_{12}Bi_aFe_bA_cCo_dB_eC_fO_g \qquad (2)$$

wherein Mo represents molybdenum; Bi represents bismuth; Fe represents iron; element A represents an element having an ion radius larger than 0.96 Å (except for potassium, cesium, and rubidium); Co represents cobalt; element B represents at least one element selected from the group consisting of magnesium, zinc, copper, nickel, manganese, chromium, and tin; element C represents at least one element selected from the group consisting of potassium, cesium, and rubidium; a to g each represent the atomic ratio of each element to 12 Mo atoms wherein the atomic ratio a of Bi is 1≤a≤5, the atomic ratio b of Fe is 1.5≤b≤6, the atomic ratio c of element A is 1≤c≤5, the atomic ratio d of Co is 1≤d≤8, the atomic ratio e of element B is 0≤e<3, the atomic ratio f of element C is 0≤f≤2, and the ratio of Fe/Co is 0.8≤b/d; and g represents the atomicity of oxygen determined by the valences of constituent elements other than oxygen.

In the ammoxidation catalyst according to the second embodiment, Co is an essential element, as with Mo, Bi, and Fe, from the viewpoint of industrially synthesizing unsaturated nitrile. Co plays a role as a carrier for forming the composite oxide $CoMoO_4$ and highly dispersing active species such as Bi—Mo—O and also plays a role in taking up oxygen from the gas phase and supplying this oxygen to Bi—Mo—O or the like. Co and Mo are preferably composited to form a composite oxide $CoMoO_4$, from the viewpoint of obtaining unsaturated nitrile at high yields. The atomic ratio d of Co is preferably 1≤d≤8, more preferably 2≤d≤8, further preferably 2≤d≤6, still further preferably 2≤d≤4, from the viewpoint of reducing the formation of unary oxides such as $Co_3O_4$ or CoO.

In the composition formula (2), element B represents at least one element selected from the group consisting of magnesium, zinc, copper, nickel, chromium, manganese, and tin and presumably substitutes some cobalt atoms in the oxide catalyst. The atomic ratio e of element B is preferably 0≤e<3, more preferably 0≤e≤2, from the viewpoint of keeping the balance with the formation of crystals of the disordered phase. Element B is not essential, but tends to contribute to the stabilization of the crystal structure of $CoMoO_4$ in the catalyst.

Element A represents an element having an ion radius larger than 0.96 Å except for potassium, cesium, and rubidium. The atomic ratio c of element A is preferably 1≤c≤5, more preferably 1≤c≤4, further preferably 1≤c≤3.

Element C represents at least one element selected from the group consisting of potassium, cesium, and rubidium. Element C probably plays a role in neutralizing the acid center of uncomposited $MoO_3$ or the like in the ammoxidation catalyst. The presence or absence of potassium, cesium, and/or rubidium contained therein does not directly influence the crystal structure of the disordered phase described later. The atomic ratio f of element C to 12 Mo atoms is preferably 0≤f≤2, more preferably 0.01≤f≤2, further preferably 0.01≤f≤1, from the viewpoint of catalytic activity. At the atomic ratio f of 0 or larger, the neutralizing effect tends to be further improved. At the atomic ratio f of 2 or smaller, the oxide catalyst tends to be rendered basic to neutral. The resulting oxide catalyst tends to easily adsorb the starting material propylene, isobutylene, isobutanol, or t-butyl alcohol and also tends to exhibit further improved catalytic activity.

Element B and element C form crystal structures separately from the crystal structure of the disordered phase described later and therefore, do not directly influence the crystal structure of the disordered phase.

The ammoxidation catalyst may contain arbitrary components as other metal components without inhibiting the formation of the disordered phase $Bi_{3-x}A_xFe_1Mo_2O_{12}$.

(3) Component Other than Metal Oxide

The ammoxidation catalyst according to the second embodiment may further comprise a carrier for supporting the metal oxide. The catalyst further comprising the carrier is preferred because of highly dispersing the metal oxide and imparting high wear resistance to the supported metal oxide.

Examples of the carrier include, but not limited to, at least one selected from the group consisting of silica, alumina, titania, and zirconia. The oxide catalyst supported by such a carrier tends to have further improvement in physical properties suitable for fluidized-bed reaction, such as particle shape, size, distribution, flowability, and mechanical strength. Among them, silica is preferred as the carrier. In general, the silica carrier is preferred in terms of its property of imparting the physical properties suitable for fluidized-bed reaction to the oxide catalyst as well as because of being inactive in itself compared with other carriers and having favorable binding effect on the metal oxide without reducing selectivity to unsaturated nitrile. In addition, the silica carrier is also preferred because of easily imparting high wear resistance to the metal oxide supported thereby.

A silica sol is preferred as a silica source. The concentration of the silica sol in the state of a starting material unmixed with other components is preferably 10 to 50% by mass from the viewpoint of the dispersibility of silica particles. The silica sol preferably comprises 40 to 100% by mass of at least one silica sol (a) containing primary silica particles having an average particle diameter of 20 nm to smaller than 55 nm, preferably 20 to 50 nm, and 60 to 0% by mass of at least one silica sol (b) containing primary silica particles having an average particle diameter of 5 nm to smaller than 20 nm, from the viewpoint of the selectivity of unsaturated nitrile.

The content of the carrier is preferably 20 to 80% by mass, more preferably 30 to 70% by mass, further preferably 40 to 60% by mass, with respect to 100% by mass in total of the carrier and the oxide catalyst. Setting the content of the carrier falls within the range described above, the yield of unsaturated nitrile tends to be further improved.

[2] Method for Producing Ammoxidation Catalyst

The method for producing the ammoxidation catalyst according to the second embodiment comprises:

a mixing step of mixing starting materials constituting the catalyst, comprising molybdenum, bismuth, iron, cobalt, and an element A having an ion radius larger than 0.96 Å (except for potassium, cesium, and rubidium), to obtain slurry;

a drying step of drying the slurry thus obtained to obtain a dried product; and a calcination step of calcining the dried product thus obtained, wherein the calcination step comprises a heating step of gradually heating the dried product from 100° C. to 200° C. over 1 hour or longer. The details of the method for producing the ammoxidation catalyst according to the second embodiment are as described in the first embodiment.

[3] Method for Producing Unsaturated Nitrile

The method for producing unsaturated nitrile according to the second embodiment comprises an unsaturated nitrile production step of reacting olefin and/or alcohol with molecular oxygen and ammonia in a fluidized-bed reactor using the oxide catalyst according to the second embodiment to obtain the unsaturated nitrile.

Examples of the olefin and/or the alcohol include, but not limited to, one or more selected from the group consisting of propylene, isobutylene, propanol, isopropanol, isobutanol, and t-butyl alcohol.

One or more selected from the group consisting of propylene, isobutylene, isobutanol, and t-butyl alcohol can be reacted with molecular oxygen and ammonia using the ammoxidation catalyst according to the second embodiment to produce acrylonitrile or methacrylonitrile. The reaction is preferably carried out using a fluidized-bed reactor. The starting materials propylene, isobutylene, isobutanol, t-butyl alcohol, and ammonia are not necessarily required to be highly pure, and industrial-grade starting materials can be used.

Usually, air is preferably used as a molecular oxygen source. A gas having an oxygen concentration raised, for example, by the mixing of oxygen with air may also be used. As for the composition of the feed gas, the molar ratio of propylene, isobutylene, isobutanol, and/or t-butyl alcohol to ammonia and molecular oxygen [(propylene, isobutylene, isobutanol, and/or t-butyl alcohol)/ammonia/molecular oxygen] is preferably 1/0.8 to 1.4/1.4 to 2.4, more preferably 1/0.9 to 1.3/1.6 to 2.2.

The reaction temperature is preferably 350 to 550° C., more preferably 400 to 500° C.

The reaction pressure is preferably ordinary pressure to 0.3 MPa.

The duration of the contact between the feed gas and the catalyst is preferably 0.5 to 20 sec·g/cc, more preferably 1 to 10 sec·g/cc.

[Third Embodiment]
[Method for Producing Unsaturated Aldehyde]

The method for producing unsaturated aldehyde according to the third embodiment comprises an unsaturated aldehyde production step of oxidizing olefin and/or alcohol using the oxide catalyst according to the first embodiment to obtain the unsaturated aldehyde.

The unsaturated aldehyde production step preferably comprises a discharging step of discharging a product gas comprising the unsaturated aldehyde from a fluidized-bed reactor through the gas-phase catalytic oxidation reaction of the olefin and/or the alcohol with an oxygen source in the fluidized-bed reactor.

The olefin and/or the alcohol is preferably at least one selected from the group consisting of propylene, isobutylene, propanol, isopropanol, isobutanol, and t-butyl alcohol.

Preferably, the gas-phase catalytic oxidation reaction is performed at a reaction temperature of 400 to 500° C., and the product gas discharged from the fluidized-bed reactor has an oxygen concentration of 0.03 to 0.5% by volume.

Hereinafter, the third embodiment will be described in more detail.

[Olefin]

Examples of the starting material olefin include, but not limited to, propylene, n-butene, isobutylene, n-pentene, n-hexene, and cyclohexene. Among them, one or more compound(s) selected from the group consisting of propylene and isobutylene is preferred. Use of such olefin tends to further improve the yield of unsaturated aldehyde.

[Alcohol]

Examples of the starting material alcohol include, but not limited to, propanol, butanol, isobutanol, and t-butyl alcohol. Among them, one or more compound(s) selected from the group consisting of propanol, isobutanol, and t-butyl alcohol is preferred. Use of such alcohol tends to further improve the yield of unsaturated aldehyde.

The lower limit of the concentration of the olefin and/or the alcohol introduced to the fluidized-bed reactor is preferably 5.0% by volume or higher, more preferably 6.0% by volume or higher, further preferably 7.0% by volume or higher, of the whole gas introduced to the fluidized-bed reactor. Setting the lower limit of the concentration falls within the range described above, the productivity of unsaturated aldehyde tends to be further improved. The upper limit of the concentration is preferably 10% by volume or lower, more preferably 9.5% by volume or lower, further preferably 9.0% by volume or lower. Setting the upper limit of the concentration falls within the range described above, the yield of unsaturated aldehyde tends to be further improved.

The method for producing unsaturated aldehyde according to the third embodiment can produce, for example, acrolein, using propylene or propanol as a starting material. Alternatively, the method for producing unsaturated aldehyde according to the third embodiment can produce methacrolein using isobutylene, isobutanol, or t-butyl alcohol as a starting material. The olefin and the alcohol may contain water, nitrogen, and alkanes such as propane, butane, and isobutane.

[Oxygen Source]

In the method for producing unsaturated aldehyde according to the third embodiment, unsaturated aldehyde is produced through the gas-phase catalytic oxidation reaction of olefin and/or alcohol with an oxygen source using the oxide catalyst. This gas-phase catalytic oxidation reaction is not limited by the oxygen source, and, for example, a mixed gas of molecular oxygen-containing gas and diluent gas can be used.

Examples of the molecular oxygen-containing gas include, but not limited to, oxygen-containing gases such as pure oxygen gas and air. Among them, air is preferably used as the molecular oxygen-containing gas. Use of the air tends to be excellent from an industrial standpoint such as cost.

Examples of the diluent gas include, but not limited to, nitrogen, carbon dioxide, water vapor, and mixed gases thereof.

The mixing ratio between the molecular oxygen-containing gas and the diluent gas in the mixed gas preferably satisfies conditions (by volume) represented by the following inequality:

$$0.01 < \text{molecular oxygen-containing gas}/(\text{molecular oxygen-containing gas}+\text{diluent gas}) < 0.3.$$

At a high reaction temperature, the gas-phase catalytic oxidation reaction easily proceeds and tends to run out of oxygen. For this reason, the oxygen source is preferably supplied to the oxide catalyst in a larger amount than that of the olefin and/or the alcohol. For the gas-phase catalytic oxidation reaction with a high olefin and/or alcohol concentration, preferably, sufficient oxygen is supplied to the oxide catalyst while a sufficient amount of the oxygen source is also supplied thereto in order to prevent the excessive reduction of the oxide catalyst. The excessive supply of the oxygen source, however, is responsible for the decomposition reaction and combustion reaction of unsaturated aldehyde and rather tends to reduce yields. Thus, the oxygen source is preferably supplied at an appropriate proportion. From these points of view, the oxygen source in the production method according to the third embodiment is supplied to the oxide catalyst such that the molar ratio of the air supplied to the catalyst layer to the olefin and/or the alcohol is preferably 7.0 to 10.5, more preferably 8.0 to 9.5, further preferably 8.0 to 9.0. Setting the molar ratio of the air supplied to the catalyst layer to the olefin and/or the alcohol is 7.0 or larger, the olefin and/or alcohol concentration tends to be low, resulting in the further prevention of the reduction degradation of the oxide catalyst. Setting the molar ratio of the air supplied to the catalyst layer is 10.5 or smaller, the concentration of oxygen supplied to the catalyst layer tends to be low, resulting in the further prevention of the oxidation degradation of the oxide catalyst.

The olefin, the alcohol, and the molecular oxygen-containing gas may contain water vapor. The water vapor contained therein tends to further inhibit oxide catalyst coking.

The diluent gas may contain water vapor. The lower content of the water vapor in the diluent gas is more preferred. The water vapor contained therein tends to further inhibit the formation of by-products such as acetic acid.

The concentration of the water vapor contained in the whole gas supplied to the reactor is preferably 0.01 to 30% by volume.

[Fluidized-bed Reactor]

The method for producing unsaturated aldehyde according to the third embodiment preferably employs a fluidized-bed reactor (hereinafter, also simply referred to as a "reactor"). The fluidized-bed reactor refers to an apparatus that has a gas distributor, an interpolator, and a cyclone as main constituents in the reactor and has a structure in which the oxide catalyst is contacted with feed gas while allowed to flow. More specifically, fluidized-bed reactors or the like described in, for example, Handbook of Fluidized Bed (published by Baifukan Co., Ltd., 1999) may be used. Among them, a fluidized-bed reactor based on a bubbling fluidized-bed system is particularly suitable for the method. The generated reaction heat can be removed using a cooling tube installed in the fluidized-bed reactor.

[Reaction Temperature of Gas-phase Catalytic Oxidation Reaction]

In the method for producing unsaturated aldehyde according to the third embodiment, the reaction temperature of the gas-phase catalytic oxidation reaction is preferably 400 to 500° C., more preferably 420 to 470° C., further preferably 430 to 450° C. At a reaction temperature of 400° C. or higher, the rate of conversion and a reaction rate tend to be further improved, resulting in the further improved yield of unsaturated aldehyde. At a reaction temperature of 500° C. or lower, the combustion decomposition of the formed unsaturated aldehyde tends to be further prevented. The reaction temperature of the gas-phase catalytic oxidation reaction can be measured with a thermometer installed in the fluidized-bed reactor.

Since the gas-phase catalytic oxidation reaction is usually exothermic reaction, the fluidized-bed reactor is preferably provided with a cooling apparatus for heat removal in order to set a suitable reaction temperature. The reaction temperature can be adjusted to the range described above by the heat removal of reaction heat using a cooling tube or by heat supply using a heating apparatus.

[Methods for Introducing Olefin and/or Alcohol and Oxygen Source]

The olefin and/or the alcohol and the oxygen source may be introduced by any method without limitations. For example, a gas containing olefin and/or alcohol and air or a gas having an increased oxygen concentration may be mixed in advance and introduced to a fluidized-bed reactor filled with the oxide catalyst. Alternatively, each gas may be introduced individually thereto. Each gas that is subjected to the reaction may be introduced to the reactor and then heated to a predetermined reaction temperature or may be preheated and then introduced to the reactor. Among these approaches, preheating followed by introduction to the reactor is preferred for continuous and efficient reaction.

[Concentration of Oxygen in Product Gas Discharged from Fluidized-bed Reactor]

The concentration of oxygen in the product gas discharged from the fluidized-bed reactor is preferably 0.03 to 0.5% by volume, more preferably 0.03 to 0.2% by volume, further preferably 0.05 to 0.1% by volume. At an oxygen concentration of 0.5% by volume or lower at the reactor outlet, the excessive reduction of the catalyst tends to be further prevented. At an oxygen concentration of 0.03% by volume or higher, the excessive oxidation of the catalyst is prevented. In either case, the yield of unsaturated aldehyde tends to be further improved. The oxygen concentration at the reactor outlet can be adjusted to the range described above to prevent the combustion decomposition of unsaturated aldehyde without falling out of the balance in the degree of redox.

The product gas containing the unsaturated aldehyde of interest is discharged from the reactor outlet. Hereinafter, the concentration of oxygen in the product gas discharged from the fluidized-bed reactor is also referred to as a "reactor-outlet oxygen concentration". In this context, the "reactor-outlet oxygen concentration" refers to the concentration of oxygen in the unsaturated aldehyde-containing product gas discharged from the reactor outlet. The reactor-outlet oxygen concentration can be measured in a region where the ratio of oxygen in the product gas is constant near the outlet of the fluidized-bed reactor. The region does not have to be a site where the product gas is discharged from the fluidized-bed reactor or the vicinity thereof in a strict sense. Thus, the reactor-outlet oxygen concentration may be measured in the gas at any point in time from during residence downstream of the reactor or immediately before discharge from the reactor to immediately before purification operation. For example, the product gas may be rapidly cooled, then absorbed into water, and purified by extractive distillation. In such a case, the product gas for the measurement of the reactor-outlet oxygen concentration can be sampled in the tubing between the reactor and a rapid cooling column disposed downstream of the reactor. The reactor-outlet oxygen concentration can be measured by gas chromatography equipped with a thermal conductivity detector (TCD).

It is important to control the reactor-outlet oxygen concentration within the range descried above, because the reactor-outlet oxygen concentration influences the decomposition of unsaturated aldehyde or secondary reaction in the reactor. The reactor-outlet oxygen concentration can be adjusted by changing the molar ratio of the oxygen source supplied to the fluidized-bed reactor to the olefin and/or the alcohol, the amount of the oxygen-containing gas supplied to the fluidized-bed reactor, the reaction temperature, the inside pressure of the reactor, the duration of the contact between the starting material mixed gas and the oxide catalyst, the amount of the catalyst, and the amount of the whole gas supplied to the reactor. Among these approaches, the control of the amount of the molecular oxygen-containing gas, for example, air, supplied to the fluidized-bed reactor is preferred for the adjustment.

For example, feed gas may be supplied under conditions involving a reaction temperature of 440° C., a reaction pressure of 0.05 MPa, and a flow rate of 595 cm²/min (in terms of NTP) using 40 g of an oxide represented by $Mo_{12}Bi_{2.0}Ce_{2.0}Fe_{3.4}Co_{3.0}Cs_{0.16}O_x$ as a catalyst. In such a case, the molar ratio composition of the feed gas can be changed from isobutylene/air/helium=1/9.2/balance (isobutylene concentration=8% by volume) to isobutylene/air/helium=1/8.1/balance (isobutylene concentration=8% by volume) to change the concentration of oxygen in the gas at the reactor outlet from 0.4% by volume to 0.05% by volume. In this context, "isobutylene/air/helium=1/8.1/balance (isobutylene concentration=8% by volume)" means that the amount of helium is determined such that the ratio of isobutylene/air satisfies 1/8.1 and the isobutylene concentration satisfies 8% by volume.

Examples of conditions for adjusting the reactor-outlet oxygen concentration include the rate of conversion as well as the amount of the catalyst, the duration of contact, the reaction pressure, and the space velocity, as described above. These conditions can be integrally adjusted to adjust the reactor-outlet oxygen concentration to an arbitrary value. For example, the reaction may be performed at a reaction temperature adjusted to the range of 430° C. to 500° C. and an olefin and/or alcohol concentration adjusted to the range of 6 to 10% by volume. In such a case, the duration of contact defined by the following expression for adjusting the reactor-outlet oxygen concentration is preferably 5.0 (g·sec/cm²) or shorter, more preferably 4.0 (g·sec/cm²) or shorter, further preferably 3.0 (Tsec/cm²) or shorter:

Duration of contact (g·sec/cm²)=$W/F$*60*273.15/(273.15+$T$)*($P$*1000+101.325)/101.325 wherein W represents the amount (g) of the catalyst charged into the fluidized-bed reactor; F represents the flow rate (cm²/min, in terms of NTP) of the starting material mixed gas; T represents reaction temperature (° C.); and P represents reaction pressure (MPa).

For adjusting the reactor-outlet oxygen concentration to the range described above, the reaction pressure is preferably ordinary pressure to 5 atm. The space velocity is preferably 400 to 4000/hr [under normal temperature pressure (NTP) conditions].

[Oxide Catalyst]

The oxide catalyst according to the first embodiment is used as the oxide catalyst in the third embodiment. Among the oxide catalysts exemplified above, an oxide catalyst comprising molybdenum, bismuth, iron, cobalt, and a lanthanoid element wherein the atomic ratio of the iron to the cobalt (Fe/Co) satisfies Fe/Co≥1, and further comprising a carrier is preferably used.

The presence or absence of each element in the oxide catalyst and the atomic ratio of each element can be identified by X-ray fluorescence analysis (XRF).

Mo, Bi, Fe, and Co are essential components for forming the oxide catalyst. Olefin and/or alcohol undergoes oxidation reaction by lattice oxygen in this oxide catalyst to yield unsaturated aldehyde. When lattice oxygen in the oxide catalyst is consumed in oxidation reaction, oxygen vacancy generally occurs in the oxide catalyst. As a result, the reduction of the oxide catalyst proceeds as the oxidation reaction proceeds. The reduced oxide catalyst is inactivated. It is therefore required to immediately reoxidize such a reduced oxide catalyst. An oxide containing Mo, Bi, Fe, and Co is reactive with the olefin and/or the alcohol and with the oxygen source and also appears to be excellent in reoxidizing effect of incorporating molecular oxygen in the gas phase into the oxide by dissociative adsorption and regenerating the consumed lattice oxygen. Thus, it is likely that this reoxidizing effect can be maintained even during oxidation reaction over a long time so that unsaturated aldehyde is stably produced from the olefin and/or the alcohol without inactivating the oxide catalyst.

In a Mo—Bi metal oxide containing Mo, Bi, Fe, and Co, these metal elements can be composited. In the oxide catalyst of the third embodiment, the atomic ratio a of Bi to 12 Mo atoms is 1≤a≤5, preferably 1.5≤a≤4, more preferably 1.8≤a≤4. Provided that the atomic ratio a falls within the range described above, the selectivity of the product of interest is further improved. Bi and Mo preferably form Bi—Mo—O composite oxides such as $Bi_2Mo_3O_{12}$ and $Bi_2MoO_6$, which are reportedly active species in gas-phase catalytic oxidation, ammoxidation reaction, and the like.

Fe is an essential element, as with Mo and Bi, for industrially synthesizing unsaturated aldehyde. The atomic ratio b of Fe to 12 Mo atoms in the oxide catalyst is 1.5≤b≤6, preferably 2≤b≤5.5, more preferably 3≤b≤5. Provided that the atomic ratio b falls within the range described above, the solid solution of iron in $CoMoO_4$ can occur by use of the redox between trivalent iron and divalent iron to form a catalyst having reduction resistance even in a reactor containing a small amount of oxygen.

Co is an essential element, as with the elements described above, for industrially synthesizing unsaturated aldehyde. Co forms a composite oxide (e.g., $CoMoO_4$) with Mo and probably plays a role in taking up oxygen from the gas phase and supplying this oxygen to Bi—Mo—O or the like. From such a point of view, the atomic ratio d of Co is preferably 1≤d≤8, more preferably 2≤d≤7, further preferably 2.5≤d≤6.

Upon solid solution of iron in $CoMoO_4$, the reduction resistance of the oxide catalyst is improved. In this regard, the atomic ratio Fe/Co of the iron to the cobalt in the oxide catalyst for use in the third embodiment is preferably Fe/Co≥0.8, more preferably Fe/Co≥1, further preferably Fe/Co≥1.05, still further preferably Fe/Co≤1.1. The upper limit of Fe/Co is preferably 3≥Fe/Co, more preferably 2≥Fe/Co, further preferably 1.5≥Fe/Co. Usually, iron is oxidized into a trivalent form. The trivalent iron is less susceptible to solid solution in $CoMoO_4$. An oxide catalyst having high reduction resistance is difficult to obtain even if iron is merely increased. Nonetheless, the gas-phase catalytic oxidation reaction of olefin and/or alcohol at a temperature of 400° C. or higher and 500° C. or lower using an oxide catalyst having the composition of Fe/Co≥0.8 has been shown to reduce trivalent iron and thereby improve the reduction resistance of the oxide catalyst by the solid solution of the resulting iron in $CoMoO_4$. The successful solid solution of iron in $CoMoO_4$ can be determined on the basis of peak shift in XRD of $CoMoO_4$. More specifically, the solid solution of iron in $CoMoO_4$ can be confirmed by a method described in Examples.

The oxide catalyst for use in the third embodiment preferably has composition represented by the following formula (1)

$$Mo_{12}Bi_aFe_bCo_dA_cB_eC_fO_g \qquad (1)$$

wherein Mo represents molybdenum; Bi represents bismuth; Fe represents iron; Co represents cobalt;

A represents at least one lanthanoid element selected from the group consisting of lanthanum, cerium, praseodymium, and neodymium;

B represents at least one element selected from the group consisting of magnesium, zinc, copper, nickel, manganese, calcium, strontium, barium, tin, and lead;

C represents at least one element selected from the group consisting of potassium, cesium, and rubidium;

a to g each represent the atomic ratio of each element to 12 molybdenum atoms and satisfy 1≤a≤5, 1.5≤b≤6, 1≤d≤6, Fe/Co≥1, 1≤c≤5, 0≤e≤3, and 0.01≤f≤2; and g represents the atomicity of oxygen determined by the valences of constituent elements other than oxygen.

In the formula (1), lanthanoid element A represents at least one element selected from the group consisting of lanthanum, cerium, praseodymium, and neodymium. As mentioned above, Bi and Mo form a Bi—Mo—O composite oxide, which has high catalytic activity, but a low melting point and low heat resistance. On the other hand, the lanthanoid element and Mo rarely form a composite oxide such as A-Mo—O, which however has a high melting point and very high heat resistance. The appropriate compositing of these oxides forms heat-resistant Bi-A-Mo—O through the compositing of Bi, element A, and Mo. The formed composite oxide has both high activity and high heat resistance suitable as a fluidized-bed catalyst.

In the formula (1), element B represents at least one element selected from the group consisting of magnesium, zinc, copper, nickel, manganese, calcium, strontium, barium, tin, and lead. Element B presumably substitutes some cobalt atoms in the oxide catalyst. Element B is not essential, but contributes to improvement in the activity of the catalyst or the stabilization of the crystal structure of $CoMoO_4$ in the catalyst. For example, copper has the effect of improving the activity of the catalyst. Nickel, magnesium, zinc, and manganese have the effects of stabilizing the crystal structure of $CoMoO_4$ and inhibiting, for example, phase transition attributed to pressure or temperature. The atomic ratio e of such element B is preferably 0≤e<3, more preferably 0≤e<2, further preferably 0≤e<1.5. Setting the atomic ratio e falls within the range described above, the effects can be exhibited without destroying the structure with the solid solution of iron in $CoMoO_4$.

In the formula (1), C represents at least one element selected from the group consisting of cesium, rubidium, and potassium. Element C probably plays a role in neutralizing the acid center of uncomposited $MoO_3$ or the like in the oxide catalyst. The atomic ratio f of element C to 12 Mo atoms is preferably 0≤f≤2, more preferably 0.01≤f≤2, further preferably 0.05≤f≤0.5. Setting the atomic ratio f falls within the range described above, the catalytic activity tends to be further improved. Particularly, at the atomic ratio f of 2 or smaller, the oxide catalyst is rarely rendered basic. In addition, the oxide catalyst easily adsorbs the starting material olefin and/or alcohol in the oxidation reaction of the olefin and/or the alcohol and tends to further improve the catalytic activity.

(Carrier)

The oxide catalyst for use in the third embodiment is supported by a carrier. The content of the carrier is preferably 20 to 80% by mass, more preferably 30 to 70% by mass, further preferably 40 to 60% by mass, with respect to the total mass of the carrier and the oxide catalyst. Setting the content of the carrier falls within the range described above, the yield of unsaturated aldehyde tends to be further improved. The supported catalyst comprising an oxide containing Mo, Bi, Fe, Co, and lanthanoid atoms can be obtained by a method known in the art, for example, a method comprising: a mixing step of mixing starting materials to prepare slurry; a drying step of spray-drying the slurry; and a calcination step of calcining the dried product obtained in the drying step.

The carrier is preferably, but not limited to, at least one selected from the group consisting of, for example, silica, alumina, titania, and zirconia. The supporting of the oxide catalyst by such a carrier tends to improve thereto physical properties suitable for fluidized-bed reaction, such as particle shape, size, distribution, flowability, and mechanical strength. Among them, silica is preferred as the carrier. The silica carrier has the property of imparting the physical properties suitable for fluidized-bed reaction to the oxide catalyst. In addition, the silica carrier is inactive compared with other carriers and has favorable binding effect on the catalyst without reducing the catalytic activity against the product of interest or selectivity thereto.

[Method for Producing Oxide Catalyst]

The oxide catalyst for use in the third embodiment may be produced by any method known in the art without limitations. The oxide catalyst for use in the third embodiment can be obtained, for example, by a production method comprising: a mixing step of mixing starting materials to prepare slurry; a drying step of spray-drying the slurry to obtain a dried product; and a calcination step of calcining the dried product. Hereinafter, a preferred aspect of the method for producing the oxide catalyst, comprising these steps will be described.

The mixing step involves preparing slurry using catalyst starting materials. Examples of the catalyst starting materials include molybdenum, bismuth, iron, cobalt, and lanthanoid elements such as lanthanum, cerium, praseodymium, and neodymium. Other examples of the catalyst starting materials include, but not limited to, manganese, nickel, copper, zinc, lead, alkali metal elements, magnesium, calcium, strontium, barium, and rare earth elements other than those described above. These starting materials can be used in the forms of ammonium salt, nitrate, hydrochloride, sulfate, and organic acid salts, which are soluble in water or nitric acid. Particularly, ammonium salt is preferred as an element source of molybdenum. Sources of elements other than molybdenum are preferably nitrates containing each element.

As mentioned above, silica, alumina, titania, zirconia, or the like may be used as a carrier for the oxide. Silica is preferably used as the carrier. A silica sol is preferred as a silica source.

The concentration of the silica sol in a state unmixed with other components in the slurry or the like is preferably 10 to 50% by mass, more preferably 15 to 45% by mass, further preferably 20 to 40% by mass. Setting the concentration falls within the range described above, the dispersibility of silica particles tends to be further improved.

The silica sol preferably comprises 40 to 100% by mass of at least one silica sol (a) containing primary silica particles having an average particle diameter of 20 to 55 nm, preferably 20 to 50 nm, and 60 to 0% by mass of at least one silica sol (b) containing primary silica particles having an average particle diameter of 5 nm to 20 nm, from the viewpoint of the selectivity of the product of interest.

The amount of the silica carrier for supporting the obtained oxide catalyst is preferably 20 to 80% by mass, more preferably 30 to 70% by mass, further preferably 40 to 60% by mass, with respect to the total mass of the oxide catalyst and the silica carrier.

The slurry can be prepared by the addition of ammonium salt of molybdenum dissolved in water to a silica sol and the subsequent addition of a solution containing nitrate of each element source other than molybdenum dissolved in water or an aqueous nitric acid solution. The order where these materials are added may be appropriately changed.

The drying step involves spray-drying the slurry thus obtained in the mixing step to obtain a dried product (dry particles). The slurry can be sprayed by any of usual methods such as centrifugation systems, two-fluid nozzle systems, and high-pressure nozzle systems, which are industrially carried out. Among them, a centrifugation system is preferred. Next, the particles obtained by spraying are dried. Air heated with steam, an electrical heater, or the like is preferably used as a dry heat source. The temperature at the dryer inlet is preferably 100 to 400° C., more preferably 150 to 300° C.

The calcination step involves calcining the dry particles thus obtained in the drying step to obtain the desired catalyst. For the calcination, preferably, the dry particles are preliminarily calcined, if necessary, at 150 to 400° C., and then finally calcined at a temperature ranging from 400 to 700° C., preferably 500 to 700° C., for 1 to 20 hours. The calcination can be performed using a kiln such as a rotary furnace, a tunnel furnace, or a muffle furnace. The particle sizes of the catalyst are preferably distributed in the range of 10 to 150 μm.

EXAMPLES

Example A

Example A is provided in the following to further illustrate a first aspect of the present invention, but is not intended to limit the scope of the first aspect of the present invention thereto. Since the atomic ratio of oxygen in an oxide catalyst is determined by the atomic valence conditions of other elements, the atomic ratio of oxygen is omitted in the formula representing the composition of a catalyst in Examples and Comparative Examples. The composition ratio of each element in an oxide catalyst was calculated from the composition ratio for preparation.

In Example A and Comparative Example A in the following, aqueous dispersions of various metals were used as catalyst starting materials. Each of the aqueous dispersions of bismuth oxide, iron oxide, and cobalt oxide for use was made by CIK Nanotek Corporation, and each of the aqueous dispersions of lanthanum oxide and cerium oxide for use was made by Taki Chemical Co., Ltd.

<Measurement of Average Particle Size>

The average particle size was obtained by calculation based on the following equation:

$$\text{Average particle size [nm]} = 6000/(\text{Surface area [m}^2/\text{g]} \times \text{Real density (8.99 g/cm}^3\text{)}).$$

<Measurement of pH>

The measurement was performed with a pH meter KR5E made by AS ONE.

<Measurement of X-ray Diffraction Angle>

In XRD measurement, the (111) plane and the (200) plane of a $LaB_6$ compound as standard reference material 660 according to National Institute of Standards & Technology were measured, such that the values were normalized to 37.441° and 43.506°, respectively.

An XRD apparatus Bruker D8 Advance was used. The XRD measurement conditions were as follows: an X-ray output of 40 kV-40 mA, a divergence slit (DS) of 0.3°, a step width of 0.02°/step, a counting time of 2.0 sec, and a measurement range of $2\theta = 5°$ to 60°.

<Rate of Conversion, Selectivity, and Yield>

In Example A and Comparative Example A, the reaction performance was represented by rate of conversion, selectivity, and yield, which are defined by the following expressions.

$$\text{Rate of conversion} = (\text{number of moles of reacted starting material}/\text{number of moles of supplied starting material}) \times 100$$

$$\text{Selectivity} = (\text{number of moles of produced compound}/\text{number of moles of reacted compound}) \times 100$$

$$\text{Yield} = (\text{number of moles of produced compound}/\text{number of moles of supplied starting material}) \times 100$$

<Evaluation of Reducibility>

The reducibility was evaluated for accelerated evaluation of the reduction resistance of a catalyst. The catalyst was reduced by the reduction treatment in a gas atmosphere containing no oxygen and re-oxidized in the returned reaction evaluation conditions. The process was repeated to achieve accelerated evaluation of the reduction resistance of the catalyst.

A mixed gas of 2% by volume of olefin and/or alcohol and 98% by volume of helium was passed at a flow rate of 3.0 cc/sec (converted to NTP) for 5 minutes for reduction treatment, and then the reaction evaluation conditions were restored and the flow was maintained for 5 minutes. This constituted one set, and the reaction was evaluated after 100 sets of executions. After further 100 sets of executions, the reaction and the reduction resistance were evaluated. The reducibility evaluation for the methacrolein reaction was performed at 430° C., the reducibility evaluation for the acrolein reaction was performed at 320° C., and the reducibility evaluation for the diolefin reaction was performed at 360° C.

When the rate of conversion and the selectivity are maintained compared with the initial capability, the absence of reduction degradation is determined. When the rate of conversion and the selectivity are lowered, the presence of reduction degradation is determined.

Each of elements A for use in Example A and Comparative Example A has an ion radius in the following:

La: 1.14 Å,
Ce: 1.07 Å,
Ca: 1.03 Å,

Pb: 1.24 Å, and
V: 0.56 Å,

Example A1

Into a mixed liquid of 90.5 g of ion-exchange water and 127.5 g of 30 mass % hydrogen peroxide water, 54.5 g of molybdenum trioxide was added, which was agitated and mixed at about 70° C. for dissolution. A solution (liquid A) was thus produced. Furthermore, 204.75 g of a water dispersion liquid of 10 mass % bismuth oxide having an average particle size of 51 nm, 54.3 g of a water dispersion liquid of 15 mass % cobalt oxide having an average particle size of 22 nm, 57.1 g of a water dispersion liquid of 15 mass % iron oxide having an average particle size of 39 nm, 71.9 g of a water dispersion liquid of 10 mass % lanthanum oxide having an average particle size of 40 nm, and 4.3 g of liquid of 10 mass % cesium hydroxide were mixed to produce a solution (liquid B).

The liquid A and the liquid B were mixed to produce a mixed liquid, to which aqueous ammonia was added to adjust pH to 3.2. The liquid was then agitated and mixed for about 3 hours to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 520° C. for 6 hours to produce a catalyst. The composition of the catalyst is shown in Table 1 and the measurement results of powder X-ray diffraction are shown in Table 2.

In order to evaluate the reaction of a catalyst, a jacketed SUS reaction tube having a diameter of 14 mm was filled with 4.0 g of the catalyst. A mixed gas of 8% by volume of isobutylene, 12.8% by volume of oxygen, 3.0% by volume of water vapor, and 76.2% by volume of nitrogen was passed through the tube at 430° C. at a flow rate of 120 mL/min (NTP) so as to perform the synthesis reaction of methacrolein. The results of the reaction evaluation are shown in Table 3. The results of the reaction evaluation after 100 sets and 200 sets of executions for accelerated reduction evaluation are also shown in Table 3.

Example A2

In 202.6 g of hot water at a temperature of about 90° C., 67.5 g of ammonium heptamolybdate was dissolved (liquid A). Furthermore, 37.0 g of bismuth nitrate, 22.0 g of cerium nitrate, 51.3 g of iron nitrate, 0.55 g of cesium nitrate, and 37.2 g of cobalt nitrate were dissolved in 41.9 g of 18 mass % nitric acid aqueous solution, to which 206.2 g of hot water at about 90° C. was added (liquid B).

The liquid A and the liquid B were mixed, to which aqueous ammonia was added to adjust pH to 4.1. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 540° C. for 6 hours in air to produce a catalyst. The composition of the catalyst is shown in Table 1 and the measurement results of powder X-ray diffraction are shown in Table 2.

In order to evaluate the reaction of a catalyst, a reaction tube was filled with 4.5 g of the catalyst and the synthesis reaction of methacrolein was performed in the same conditions as in Example A1. The results of the reaction evaluation are shown in Table 3.

Example A3

In 199.2 g of hot water at a temperature of about 90° C., 66.4 g of ammonium heptamolybdate was dissolved (liquid A). Furthermore, 47.0 g of bismuth nitrate, 13.5 g of cerium nitrate, 7.4 g of calcium nitrate, 42.8 g of iron nitrate, 1.56 g of rubidium nitrate, and 32.0 g of cobalt nitrate were dissolved in 41.5 g of 18 mass % nitric acid aqueous solution, to which 209.0 g of hot water at about 90° C. was added (liquid B). The liquid A and the liquid B were mixed, to which aqueous ammonia was added to adjust pH to 4.0. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 530° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 4.8 g of the catalyst and the synthesis reaction of methacrolein was performed in the same conditions as in Example A1. The results of the reaction evaluation are shown in Table 3.

Example A4

Into a mixed liquid of 90.6 g of ion-exchange water and 127.6 g of 30 mass % hydrogen peroxide water, 54.5 g of molybdenum trioxide was added, which was agitated and mixed at about 70° C. for dissolution. A solution (liquid A) was thus produced. Furthermore, 155.48 g of a water dispersion liquid of 10 mass % bismuth oxide having an average particle size of 51 nm, 4.2 g of lead nitrate, 62.4 g of a water dispersion liquid of 15 mass % cobalt oxide having an average particle size of 22 nm, 50.4 g of a water dispersion liquid of 15 mass % iron oxide having an average particle size of 39 nm, 92.6 g of a water dispersion liquid of 10 mass % lanthanum oxide having an average particle size of 40 nm, and 4.3 g of liquid of 10 mass % cesium hydroxide were mixed to produce a solution (liquid B).

The liquid A and the liquid B were mixed to produce a mixed liquid, to which aqueous ammonia was added to adjust pH to 3.6. The liquid was then agitated and mixed for about 3 hours to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 520° C. for 6 hours in air to produce a catalyst. The composition of the catalyst is shown in Table 1 and the measurement results of powder X-ray diffraction are shown in Table 2.

In order to evaluate the reaction of a catalyst, a reaction tube was filled with 4.5 g of the catalyst and the synthesis reaction of methacrolein was performed in the same conditions as in Example A1. The results of the reaction evaluation are shown in Table 3.

Example A5

In 207.2 g of hot water at a temperature of about 90° C., 69.1 g of ammonium heptamolybdate was dissolved (liquid A). Furthermore, 45.7 g of bismuth nitrate, 14.0 g of cerium nitrate, 2.3 g of manganese nitrate, 48.5 g of iron nitrate, 0.57 g of cesium nitrate, and 27.6 g of cobalt nitrate were dissolved in 40.9 g of 18 mass % nitric acid aqueous solution, to which 195.4 g of hot water at about 90° C. was added (liquid B). The liquid A and the liquid B were mixed, to which aqueous ammonia was added to adjust pH to 4.0. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 5 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 540° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 4.2 g of the catalyst and the synthesis reaction of methacrolein was performed in the same conditions as in Example A1. The results of the reaction evaluation are shown in Table 3.

Example A6

In 211.2 g of hot water at a temperature of about 90° C., 70.4 g of ammonium heptamolybdate was dissolved (liquid A). Furthermore, 34.0 g of bismuth nitrate, 21.6 g of cerium nitrate, 35.0 g of iron nitrate, 0.58 g of cesium nitrate, and 44.8 g of cobalt nitrate were dissolved in 35.3 g of 18 mass % nitric acid aqueous solution, to which 140.8 g of hot water at about 90° C. was added (liquid B).

The liquid A and the liquid B were mixed, to which aqueous ammonia was added to adjust pH to 4.1. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 540° C. for 6 hours in air to produce a catalyst. The composition of the catalyst is shown in Table 1 and the measurement results of powder X-ray diffraction are shown in Table 2.

Example A7

In 193.1 g of hot water at a temperature of about 90° C., 64.4 g of ammonium heptamolybdate was dissolved (liquid A). Furthermore, 37.0 g of bismuth nitrate, 23.7 g of cerium nitrate, 36.9 g of iron nitrate, 0.41 g of cesium nitrate, and 54.3 g of cobalt nitrate were dissolved in 34.1 g of 18 mass % nitric acid aqueous solution, to which 128.7 g of hot water at about 90° C. was added (liquid B).

The liquid A and the liquid B were mixed, to which aqueous ammonia was added to adjust pH to 4.0. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 540° C. for 5 hours in air to produce a catalyst. The composition of the catalyst is shown in Table 1 and the measurement results of powder X-ray diffraction are shown in Table 2.

Comparative Example A1

In 208.8 g of hot water at a temperature of about 90° C., 69.6 g of ammonium heptamolybdate was dissolved (liquid A). Furthermore, 28.6 g of bismuth nitrate, 28.3 g of cerium nitrate, 10.9 g of magnesium nitrate, 38.3 g of iron nitrate, 1.43 g of rubidium nitrate, and 38.5 g of nickel nitrate were dissolved in 41.9 g of 18 mass % nitric acid aqueous solution, to which 200.3 g of hot water at about 90° C. was added (liquid B). The liquid A and the liquid B were mixed, to which aqueous ammonia was added to adjust pH to 4.2. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 5 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 530° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 5.0 g of the catalyst and the synthesis reaction of methacrolein was performed in the same conditions as in Example A1. The results of the reaction evaluation are shown in Table 3.

Comparative Example A2

In 216.9 g of hot water at a temperature of about 90° C., 72.3 g of ammonium heptamolybdate was dissolved (liquid A). Furthermore, 28.1 g of bismuth nitrate, 14.7 g of cerium nitrate, 0.35 g of potassium nitrate, 19.2 g of iron nitrate, 2.0 g of cesium nitrate, and 69.8 g of cobalt nitrate were dissolved in 40.6 g of 18 mass % nitric acid aqueous solution, to which 181.7 g of hot water at about 90° C. was added (liquid B). The liquid A and the liquid B were mixed, to which aqueous ammonia was added to adjust pH to 4.3. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 520° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 5.2 g of the catalyst and the synthesis reaction of methacrolein was performed in the same conditions as in Example A1. The results of the reaction evaluation are shown in Table 3.

Comparative Example A3

In 197.2 g of hot water at a temperature of about 90° C., 65.7 g of ammonium heptamolybdate was dissolved (liquid A). Furthermore, 64.5 g of bismuth nitrate, 42.4 g of iron nitrate, 0.54 g of cesium nitrate, and 30.8 g of cobalt nitrate were dissolved in 40.6 g of 18 mass % nitric acid aqueous solution, to which 203.6 g of hot water at about 90° C. was added (liquid B). The liquid A and the liquid B were mixed, to which ammonia water was added to adjust pH to 4.0. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 540° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 6.1 g of the catalyst and the synthesis reaction of methacrolein was performed in the same conditions as in Example A1. The results of the reaction evaluation are shown in Table 3.

Comparative Example A4

In 309.9 g of hot water at a temperature of about 90° C., 70.0 g of ammonium heptamolybdate and 5.4 g of ammonium metavanadate were dissolved (liquid A). Furthermore, 46.3 g of bismuth nitrate, 45.2 g of iron nitrate, 0.57 g of cesium nitrate, and 32.8 g of cobalt nitrate were dissolved in 38.6 g of 18 mass % nitric acid aqueous solution, to which 170.3 g of hot water at about 90° C. was added (liquid B). The liquid A and the liquid B were mixed, to which aqueous ammonia was added to adjust pH to 4.5. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 3 hours in air, then to 250° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 460° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 6.0 g of the catalyst and the synthesis reaction of methacrolein was performed in the same conditions as in Example A1. The results of the reaction evaluation are shown in Table 3.

Comparative Example A5

Into a mixed liquid of 90.2 g of ion-exchange water and 127.0 g of 30 mass % hydrogen peroxide water, 54.3 g of molybdenum trioxide was added, which was agitated and mixed at about 70° C. for dissolution. A solution (liquid A) was thus produced. Furthermore, 168.9 g of a water dispersion liquid of 10 mass % bismuth oxide having an average particle size of 51 nm, 63.7 g of a water dispersion liquid of 15 mass % cobalt oxide having an average particle size of 22 nm, 66.9 g of a water dispersion liquid of 15 mass % iron oxide having an average particle size of 39 nm, 84.9 g of a water dispersion liquid of 10 mass % cerium oxide having an average particle size of 20 nm, and 4.2 g of liquid of 10 mass % cesium hydroxide were mixed to produce a solution (liquid B).

The liquid A and the liquid B were mixed, to which ammonia water was added to adjust pH to 3.0. The liquid was then agitated and mixed for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 250° C. over 20 minutes in air, and kept at 250° C. for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 530° C. for 5 hours to produce a catalyst. The composition of the catalyst is shown in Table 1 and the measurement results of powder X-ray diffraction are shown in Table 2.

In order to evaluate the reaction of a catalyst, a reaction tube was filled with 4.2 g of the catalyst and the synthesis reaction of methacrolein was performed in the same conditions as in Example A1. The results of the reaction evaluation are shown in Table 3.

Comparative Example A6

A catalyst composition $Mo_{12}Bi_{1.6}Ce_{0.4}Fe_{1.0}Co_{8.0}Cs_{0.4}K_{0.2}$, which represents atomic ratio relative to 12 Mo atoms, was prepared as follows. In 1820 g of hot water at a temperature of about 50° C., 364 g of ammonium heptamolybdate was dissolved (liquid A). Furthermore, 133 g of bismuth nitrate, 29.8 g of cerium nitrate, 69.4 g of iron nitrate, 13.4 g of cesium nitrate, 3.46 g of potassium nitrate, and 400 g of cobalt nitrate were dissolved in 290 g of 15 wt % nitric acid aqueous solution (liquid B). The liquid A and the liquid B were agitated and mixed for about 2 hours so as to produce a starting material slurry. The starting material slurry was spray dried to produce a spray dried catalyst composition precursor, which was then preliminarily calcined at 200° C. for 3 hours. The produced preliminarily calcined catalyst composition precursor in a pseudo-spherical particulate form was formed into a columnar shape having a diameter of 5 mm and a height of 4 mm by tablet compression, which was then finally calcined at 460° C. for 3 hours to produce a catalyst. The composition of the catalyst is shown in Table 1 and the measurement results of powder X-ray diffraction are shown in Table 2.

In order to evaluate the reaction of a catalyst, a reaction tube was filled with 4.2 g of the catalyst and the synthesis reaction of methacrolein was performed in the same conditions as in Example A1. The results of the reaction evaluation are shown in Table 3.

In FIG. 8, the XRD (2θ=25 to 27°) of an oxide catalyst before and after gas-phase catalytic oxidation reaction of olefin in Comparative Example A6 is illustrated. The oxide catalyst before gas-phase catalytic oxidation reaction of olefin in Comparative Example A6 had an XRD peak from $CoMoO_4$ (002) at 2θ=26.46°, and the oxide catalyst after reaction had an XRD peak from $CoMoO_4$ (002) at 2θ=26.46°. It was thus found that no bivalent Fe was solid-dissolved in $CoMoO_4$. This was attributed to the atomic ratio of iron to cobalt (Fe/Co), not satisfying the following expression: Fe/Co≥1.

<Acrolein Synthesis Reaction>

Example A8

Into a mixed liquid of 90.7 g of ion-exchange water and 127.8 g of 30 mass % hydrogen peroxide water, 54.6 g of molybdenum trioxide was added, which was agitated and mixed at about 70° C. for dissolution. A solution (liquid A) was thus produced. Furthermore, 205.3 g of a water dispersion liquid of 10 mass % bismuth oxide having an average particle size of 51 nm, 54.5 g of a water dispersion liquid of 15 mass % cobalt oxide having an average particle size of 22 nm, 57.2 g of a water dispersion liquid of 15 mass % iron oxide having an average particle size of 39 nm, 72.1 g of a water dispersion liquid of 10 mass % lanthanum oxide having an average particle size of 40 nm, and 1.4 g of liquid of 10 mass % cesium hydroxide were mixed to produce a solution (liquid B).

The liquid A and the liquid B were mixed to produce a mixed liquid, to which aqueous ammonia was added to adjust pH to 3.8. The liquid was then agitated and mixed for about 3 hours to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 5 hours in air, then to 260° C. over 1 hour, and kept at the temperature for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 510° C. for 5 hours in air to produce a catalyst. The composition of the catalyst is shown in Table 1 and the measurement results of powder X-ray diffraction are shown in Table 2.

Using the produced catalyst, acrolein was synthesized from propylene. A jacketed SUS reaction tube having an inner diameter of 15 mm was filled with 20 mL of the catalyst. A starting material gas of 10% by volume of propylene, 17% by volume of water vapor, and 73% by volume of air was passed through the tube at a reaction temperature of 320° C. so as to perform acrolein synthesis reaction. The results of the reaction evaluation are shown in Table 4.

Comparative Example A7

In 203.1 g of hot water at a temperature of about 90° C., 67.7 g of ammonium heptamolybdate was dissolved (liquid A). Furthermore, 37.1 g of bismuth nitrate, 22.0 g of cerium nitrate, 51.4 g of iron nitrate, 0.19 g of cesium nitrate, and 37.4 g of cobalt nitrate were dissolved in 41.9 g of 18 mass % nitric acid aqueous solution, to which 205.7 g of hot water at about 90° C. was added (liquid B). The liquid A and the liquid B were mixed, to which aqueous ammonia was added to adjust pH to 4.0. The liquid was then agitated and mixed at about 55° C. for about 3 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 250° C. over 20 minutes in air, and kept at 250° C. for 3 hours so as to produce a preliminarily calcined product. The produced preliminarily calcined product was formed into a ring shape having a diameter of 5 mm, a height of 4 mm, and an inner diameter of 2 mm by tablet compression, which was then finally calcined at 460° C. for 5 hours in air to produce a catalyst. The composition of the catalyst is shown in Table 1 and the measurement results of powder X-ray diffraction are shown in Table 2.

In order to evaluate the reaction of a catalyst, a reaction tube was filled with 20 mL of the catalyst and the synthesis reaction of acrolein was performed in the same conditions as in Example A8. The results of the reaction evaluation are shown in Table 4.

<Butadiene Synthesis Reaction>

Example A9

Using the same catalyst as in Example A2, butadiene was synthesized from 1-butene as follows. A jacketed SUS reaction tube having a diameter of 14 mm was filled with 6.0 g of the catalyst. A mixed gas of 8% by volume of 1-butene, 12.8% by volume of oxygen, and 79.2% by volume of nitrogen was passed through the tube at a reaction temperature of 360° C. at a flow rate of 120 mL/min (NTP) so as to perform butadiene synthesis reaction. The results of the reaction evaluation are shown in Table 5.

Comparative Example A8

Using the same catalyst as in Comparative Example A5, a reaction tube was filled with 6.0 g of the catalyst. Butadiene was synthesized from 1-butene in the same reaction conditions as in Example A9 as follows. The results of the reaction evaluation are shown in Table 5.

TABLE 1

| | Atomic composition | | | | | | | | |
|---|---|---|---|---|---|---|---|---|---|
| | Mo | Bi | Fe | Element A | Co | Element B | Element C | Fe/Co | |
| Example A1 | 12.0 | 2.9 | 3.4 | La 1.4 | 3.4 | | Cs 0.09 | 1.00 | |
| Example A2 | 12.0 | 2.4 | 4.0 | Ce 1.6 | 4.0 | | Cs 0.09 | 1.00 | |
| Example A3 | 12.0 | 3.1 | 3.4 | Ce 1.0 Ca 1.0 | 3.5 | | Rb 0.34 | 0.97 | |
| Example A4 | 12.0 | 2.2 | 3.0 | La 1.8 Pb0.4 | 3.9 | | Cs 0.09 | 0.77 | |
| Example A5 | 12.0 | 2.9 | 3.7 | Ce 1.0 | 2.9 | Mn 0.25 | Cs 0.09 | 1.29 | |
| Example A6 | 12.0 | 2.1 | 2.6 | Ce 1.5 | 4.6 | | Cs 0.09 | 0.57 | |
| Example A7 | 12.0 | 2.5 | 3.0 | Ce 1.8 | 6.1 | | Cs 0.07 | 0.49 | |
| Example A8 | 12.0 | 2.9 | 3.4 | La 1.4 | 3.4 | | Cs 0.03 | 1.00 | |
| Example A9 | 12.0 | 2.4 | 4.0 | Ce 1.6 | 4.0 | | Cs 0.09 | 1.00 | |
| Comparative Example A1 | 12.0 | 1.8 | 2.9 | Ce 2.0 | | Ni 4.0 Mg1.3 | Rb 0.3 | — | |
| Comparative Example A2 | 12.0 | 1.7 | 1.4 | Ce 1.0 | 7.0 | | Cs0.3 K0.1 | 0.20 | |
| Comparative Example A3 | 12.0 | 4.3 | 3.4 | | 3.4 | | Cs0.09 | 1.00 | |
| Comparative Example A4 | 12.0 | 2.9 | 3.4 | V 1.4 | 3.4 | | Cs 0.09 | 1.00 | |
| Comparative Example A5 | 12.0 | 2.4 | 4.0 | Ce 1.6 | 4.0 | | Cs 0.09 | 1.00 | |
| Comparative Example A6 | 12.0 | 1.6 | 1.0 | Ce0.4 | 8.0 | | Cs0.4 K0.2 | 0.13 | |
| Comparative Example A7 | 12.0 | 2.4 | 4.0 | Ce 1.6 | 4.0 | | Cs 0.03 | 1.00 | |
| Comparative Example A8 | 12.0 | 2.4 | 4.0 | Ce 1.6 | 4.0 | | Cs 0.09 | 1.00 | |

TABLE 2

| | Crystal structure | Intensity ratio Ia/Ib | X-ray diffraction peak 2θ° | | | |
|---|---|---|---|---|---|---|
| Example A1 | disorder phase | 3.3 | 18.34 | 28.16 | 33.66 | 46.10 |
| Example A2 | disorder phase | 3.3 | 18.33 | 28.12 | 33.60 | 46.19 |
| Example A3 | disorder phase | 2.6 | 18.31 | 28.22 | 33.61 | 46.16 |
| Example A4 | disorder phase | 2.9 | 18.32 | 28.15 | 33.66 | 46.13 |
| Example A5 | disorder phase | 3.1 | 18.33 | 28.14 | 33.64 | 46.14 |
| Example A6 | disorder phase | 2.1 | 18.33 | 28.21 | 33.68 | 46.16 |
| Example A7 | disorder phase | 2.0 | 18.34 | 28.15 | 33.66 | 46.17 |
| Example A8 | disorder phase | 3.3 | 18.34 | 28.21 | 33.69 | 46.19 |
| Example A9 | disorder phase | 3.3 | 18.33 | 28.12 | 33.60 | 46.19 |
| Comparative Example A1 | disorder phase | 2.3 | 18.34 | 28.20 | 33.68 | 46.18 |
| Comparative Example A2 | disorder phase | 2.1 | 18.34 | 28.16 | 33.66 | 46.17 |
| Comparative Example A3 | order phase | 1.1 | 18.10, 18.48 | 28.02, 28.35 | 33.30, 34.06 | 45.90, 46.46 |
| Comparative Example A4 | disorder phase | 3.2 | 18.38 | 28.23 | 33.68 | 46.17 |
| Comparative Example A5 | order phase | 1.3 | 18.12, 18.50 | 28.04, 28.37 | 33.34, 34.02 | 45.88, 46.44 |
| Comparative Example A6 | order phase | 1.4 | 18.13, 18.51 | 28.03, 28.36 | 33.33, 34.05 | 45.91, 46.46 |
| Comparative Example A7 | order phase | 1.3 | 18.11, 18.48 | 28.05, 28.36 | 33.34, 34.04 | 45.92, 46.48 |
| Comparative Example A8 | order phase | 1.3 | 18.12, 18.50 | 28.04, 28.37 | 33.34, 34.02 | 45.88, 46.44 |

TABLE 3

| | Initial performance | | | Accelerated reduction evaluation after 100 sets | | | Accelerated reduction evaluation after 200 sets | | |
|---|---|---|---|---|---|---|---|---|---|
| | Rate of conversion % | Methaerolein selectivity % | Methacrolein yield % | Rate of conversion % | Methacrolein selectivity % | Methacrolein yield % | Rate of conversion % | Methacrolein selectivity % | Methacrolein yield % |
| Example A1 | 95.7 | 88.5 | 84.7 | 96.0 | 88.5 | 85.0 | 96.3 | 88.5 | 85.2 |
| Example A2 | 95.6 | 88.2 | 84.3 | 95.8 | 88.1 | 84.4 | 96.0 | 88.2 | 84.7 |
| Example A3 | 95.6 | 87.1 | 83.3 | 95.4 | 86.9 | 82.9 | 95.2 | 86.7 | 82.5 |
| Example A4 | 95.7 | 87.5 | 83.7 | 95.5 | 87.3 | 83.4 | 95.2 | 87.2 | 83.0 |
| Example A5 | 95.6 | 88.0 | 84.1 | 95.5 | 88.0 | 84.0 | 95.4 | 87.8 | 83.8 |
| Example A6 | 95.6 | 86.7 | 82.9 | 95.4 | 86.6 | 82.6 | 95.2 | 86.6 | 82.4 |
| Example A7 | 95.6 | 86.2 | 82.4 | 95.4 | 86.1 | 82.1 | 95.2 | 86.1 | 82.0 |
| Comparative Example A1 | 95.7 | 82.4 | 78.9 | 95.3 | 82.2 | 78.3 | 95.0 | 82.0 | 77.9 |
| Comparative Example A2 | 95.5 | 82.0 | 78.3 | 95.1 | 81.7 | 77.7 | 94.7 | 81.2 | 76.9 |
| Comparative Example A3 | 95.7 | 80.3 | 76.8 | 87.1 | 74.1 | 64.5 | 80.1 | 68.1 | 54.5 |
| Comparative Example A4 | 95.6 | 82.2 | 78.6 | 85.0 | 73.1 | 62.1 | 75.7 | 67.7 | 51.2 |
| Comparative Example A5 | 95.6 | 77.4 | 74.0 | 87.2 | 73.9 | 64.4 | 79.5 | 67.7 | 53.8 |
| Comparative Example A6 | 95.4 | 83.8 | 79.9 | 95.8 | 83.4 | 79.9 | 96.2 | 83.1 | 79.9 |

TABLE 4

| | Initial performance | | | Accelerated reduction evaluation after 100 sets | | | Accelerated reduction evaluation after 200 sets | | |
|---|---|---|---|---|---|---|---|---|---|
| | Rate of conversion % | Acrolein selectivity % | Acrolein yield % | Rate of conversion % | Acrolein selectivity % | Acrolein yield % | Rate of conversion % | Acrolein selectivity % | Acrolein yield % |
| Example A8 | 99.1 | 94.9 | 94.0 | 99.1 | 95.0 | 94.1 | 99.1 | 94.9 | 94.0 |
| Comparative Example A7 | 99.1 | 91.5 | 90.7 | 91.0 | 84.4 | 76.8 | 84.0 | 78.6 | 66.0 |

TABLE 5

| | Initial performance | | | Accelerated reduction evaluation after 100 sets | | | Accelerated reduction evaluation after 200 sets | | |
|---|---|---|---|---|---|---|---|---|---|
| | Rate of conversion % | Butadiene selectivity % | Butadiene yield % | Rate of conversion % | Butadiene selectivity % | Butadiene yield % | Rate of conversion % | Butadiene selectivity % | Butadiene yield % |
| Example A9 | 98.0 | 93.6 | 91.7 | 98.0 | 93.6 | 91.7 | 98.0 | 93.6 | 91.7 |
| Comparative Example A8 | 98.0 | 90.1 | 88.3 | 90.2 | 83.4 | 75.2 | 84.3 | 79.9 | 67.4 |

<X-ray Diffraction Peaks of Catalysts Obtained in Example A1 and Comparative Example A3>

In FIG. 5, the X-ray diffraction peaks of catalysts obtained in Example A1 and Comparative Example A3 are illustrated. In FIG. 6, an enlarged chart of X-ray diffraction peaks for the range of 2θ=15 to 30° in FIG. 5 is illustrated. In FIG. 7, an enlarged chart for the range of 2θ=30 to 50° is illustrated. In FIG. 6 and FIG. 7, it was illustrated that the catalyst obtained in Example A1 had X-ray diffraction peaks at least at 2θ=18.34° for (101) plane, 28.16° for (112) plane, 33.66° for (200) plane, and 46.10°, with a peak intensity ratio (Ia/Ib)=3.3, wherein Ia represents the peak intensity at 2θ=33.66° and Ib represents the peak intensity at 2θ=34.06°. It can be assumed that the crystal structure of disordered phase of $Bi_{3-x}A_xFe_1Mo_2O_{12}$ was formed in the catalyst obtained in Example A1.

On the other hand, in the X-ray diffraction of the catalyst obtained in Comparative Example A3, no peak was observed at 18.30°±0.05° for (101) plane, 28.20°±0.05° for (112) plane, 33.65°±0.05° for (200) plane, and 46.15°±0.05° for (204) plane. It can be therefore assumed that the crystal structure of disordered phase of $Bi_{3-x}A_xFe_1Mo_2O_{12}$ was not formed in the catalyst obtained in Comparative Example A3.

The comparison of X-ray diffraction between the catalysts obtained in Example A1 and Comparative Example A3 are as follows. Corresponding to the peak at 18.34° for (101) plane of the catalyst obtained in Example A1, split peaks were observed at 18.10° for (310) plane and at 18.48° for (111) plane in the catalyst obtained in Comparative Example A3. Corresponding to the peak at 28.20°±0.05° for (112) plane of the catalyst obtained in Example A1, split peaks were observed at 28.02° for (221) plane and at 28.35° for (42-1) plane in the catalyst obtained in Comparative Example A3. Corresponding to the peak at 33.65°±0.05° for (200) plane of the catalyst obtained in Example A1, split peaks were observed at 33.30° for (600) plane and at 34.06° for (202) plane in the catalyst obtained in Comparative Example A3. Corresponding to the peak at 46.15°±0.05° for (204) plane of the catalyst obtained in Example A1, split peaks were observed at 45.90° for (640) plane and at 46.46° for (242) plane in the catalyst obtained in Comparative Example A3. The catalyst obtained in Example A1 had a peak intensity ratio (Ia/Ib)=1.1, wherein Ia represents the peak intensity at 2θ=33.66° and Ib represents the peak intensity at 2θ=34.06°. It can be assumed that the crystal structure of a disordered phase of $Bi_{3-x}A_xFe_1Mo_2O_{12}$ was formed in the catalyst obtained in Example A1. On the other hand, it can be assumed that an ordered phase was formed in the catalyst obtained in Comparative Example A3 instead of a disordered phase of $Bi_{3-x}A_xFe_1Mo_2O_{12}$.

Example B

Example B is provided in the following to further illustrate a second aspect of the present invention, but is not intended to limit the scope of the second aspect of the present invention thereto. Since the atomic ratio of oxygen in an ammoxidation catalyst is determined by the atomic valence conditions of other elements, the atomic ratio of oxygen is omitted in the formula representing the composition of a catalyst in Examples and Comparative Examples. The composition ratio of each element in an ammoxidation catalyst was calculated from the composition ratio for preparation.

In Example B and Comparative Example B in the following, aqueous dispersions of various metals were used as catalyst starting materials. Each of the aqueous dispersions of bismuth oxide, iron oxide, and cobalt oxide for use was made by CIK Nanotek Corporation, and each of the aqueous dispersions of lanthanum oxide and cerium oxide for use was made by Taki Chemical Co., Ltd.

<Measurement of Average Particle Size>

The average particle size was obtained by calculation based on the following equation:

Average particle size [nm]=6000/(Surface area [m$^2$/g]×Real density (8.99 g/cm$^3$).

<Measurement of pH>

The measurement was performed with a pH meter KR5E made by AS ONE.

<Measurement of X-ray Diffraction Angle>

In XRD measurement, the (111) plane and the (200) plane of a LaB$_6$ compound as standard reference material 660 according to National Institute of Standards & Technology were measured, such that the values were normalized to 37.441° and 43.506°, respectively.

An XRD apparatus Bruker D8 Advance was used. The XRD measurement conditions were as follows: an X-ray output of 40 kV-40 mA, a divergence slit (DS) of 0.3°, a step width of 0.02°/step, a counting time of 2.0 sec, and a measurement range of 2θ=5° to 60°.

<Reaction Evaluation Conditions for Ammoxidation>

40 to 60 g of a catalyst was placed in a fluidized bed reaction tube vycor glass having an inner diameter of 25 mm in which 12 sheets of 10-mesh wire screen arranged at 1-cm intervals. A mixed gas (with a volume ratio of propylene or isobutylene:ammonia:oxygen:helium of 1:1.2:1.85:7.06) was passed through the tube at a reaction temperature of 430° C. under normal reaction pressure at a flow rate of 3.64 cc/s (converted to NTP).

<Rate of Conversion, Selectivity, and Yield>

The reaction performance was represented by rate of conversion, selectivity, and yield, which are defined by the following expressions.

Rate of conversion=(number of moles of reacted starting material/number of moles of supplied starting material)×100

Selectivity=(number of moles of produced compound/number of moles of reacted starting material)×100

Yield=(number of moles of produced compound/number of moles of supplied starting material)×100

<Contact Time>

The contact time is defined by the following expression.

Contact time (sec·g/cc)=$(W/F)\times 273/(273+T)\times P/0.10$

In the expression, W represents the amount of catalyst (g), F represents the flow rate of starting material mixed gas (N·cc/sec) at normal state (0° C., 1 atm), T represents reaction temperature (° C.), and P represents reaction pressure (MPa).

<Evaluation of Reducibility>

The reducibility was evaluated for accelerated evaluation of the reduction resistance of a catalyst. The catalyst was reduced in a gas atmosphere containing no oxygen and re-oxidized in the returned reaction evaluation conditions. The process was repeated to achieve accelerated evaluation of the reduction resistance of the catalyst.

A mixed gas of 2% by volume of propylene, isobutylene, isobutanol, and/or t-butyl alcohol and 98% by volume of helium was passed at a temperature of 430° C. at a flow rate of 3.64 cc/s (converted to NTP) for 5 minutes for reduction treatment. Subsequently the reaction evaluation conditions were restored and the flow was maintained for 5 minutes. This constituted one set, and the reaction was evaluated after 100 sets of executions. After further 100 sets of executions, the reaction and the reduction resistance were evaluated.

Each of elements A for use in Example B and Comparative Example B has an ion radius in the following:

La: 1.14 Å,
Ce: 1.07 Å,
Pr: 1.06 Å,
Ca: 1.03 Å,
Pb: 1.24 Å, and
V: 0.56 Å.

Example B1

First, 125.0 g of 40 mass % silica sol which contained 26 mass % SiO$_2$ of primary silica particles having an average diameter of 44 nm, and 147.1 g of 34 mass % aqueous silica sol which contained 30 mass % SiO$_2$ of primary silica particles having an average diameter of 12 nm, and 61.3 g of water were mixed to produce 30 mass % silica starting material.

In 211.0 g of hot water at a temperature of about 90° C., 70.3 g of ammonium heptamolybdate was dissolved (liquid A). Furthermore, 38.6 g of bismuth nitrate, 22.9 g of lanthanum nitrate, 42.7 g of iron nitrate, 0.51 g of cesium nitrate, and 31.4 g of cobalt nitrate were dissolved in 36.4 g of 18 mass % nitric acid aqueous solution, to which 148.1 g of hot water at about 90° C. was added (liquid B).

The silica starting material and both of the liquid A and the liquid B were mixed, to which aqueous ammonia was added to adjust pH to 4.1. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 260° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 55 g of the catalyst was placed in a fluidized bed reaction tube vycor glass having an inner diameter of 25 mm, and the ammoxidation of propylene was performed with a contact time of 4.3 (sec·g/cc). The results of the reaction evaluation are shown in Table 8. The results of the reaction evaluation after 100 sets and 200 sets of executions for accelerated reduction evaluation are also shown in Table 8.

Example B2

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 207.8 g of hot water at a temperature of about 90° C., 69.3 g of ammonium heptamolybdate was dissolved (liquid A). Furthermore, 41.1 g of bismuth nitrate, 19.7 g of cerium nitrate, 44.7 g of iron nitrate, 0.50 g of cesium nitrate, and 32.5 g of cobalt nitrate were dissolved in 40.9 g of 18 mass % nitric acid aqueous solution, to which 194.7 g of hot water at about 90° C. was added (liquid B).

The silica starting material and both of the liquid A and the liquid B were mixed, to which aqueous ammonia was added to adjust pH to 3.3. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 55 g of the catalyst was placed in a fluidized bed reaction tube vycor glass having an inner diameter of 25 mm, and the ammoxidation of propylene was performed with a contact time of 4.2 (sec·g/cc). The results of the reaction evaluation are shown in Table 8. The results of the reaction evaluation after 100 sets and 200 sets of executions for accelerated reduction evaluation are also shown in Table 8.

Example B3

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 209.1 g of hot water at a temperature of about 90° C., 69.7 g of ammonium heptamolybdate was dissolved (liquid A). Furthermore, 44.6 g of bismuth nitrate, 17.0 g of praseodymium nitrate, 31.8 g of iron nitrate, 0.57 g of cesium nitrate, and 38.4 g of cobalt nitrate were dissolved in 40.2 g of 18 mass % nitric acid aqueous solution, to which 188.8 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 270° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 4.4 (sec·g/cc). The results of the reaction evaluation are shown in Table 8. The results of the reaction evaluation after 100 sets and 200 sets of executions for accelerated reduction evaluation are also shown in Table 8.

Example B4

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 223.4 g of hot water at a temperature of about 90° C., 74.5 g of ammonium heptamolybdate was dissolved (liquid A). Furthermore, 20.4 g of bismuth nitrate, 30.3 g of lanthanum nitrate, 45.2 g of iron nitrate, 0.54 g of cesium nitrate, 6.6 g of calcium nitrate, and 32.9 g of cobalt nitrate were dissolved in 34.3 g of 18 mass % nitric acid aqueous solution, to which 114.4 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 240° C. over 1 hour, and kept at the temperature for 4 hours so as to produce a preliminarily calcined product. The produced preliminarily calcined product was finally calcined at 580° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 4.5 (sec·g/cc). The results of the reaction evaluation are shown in Table 8. The results of the reaction evaluation after 100 sets and 200 sets of executions for accelerated reduction evaluation are also shown in Table 8.

Example B5

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 202.0 g of hot water at a temperature of about 90° C., 67.3 g of ammonium heptamolybdate was dissolved (liquid A). Furthermore, 21.5 g of bismuth nitrate, 24.6 g of cerium nitrate, 42.2 g of iron nitrate, 0.74 g of cesium nitrate, 8.4 g of lead nitrate, and 47.3 g of cobalt nitrate were dissolved in 39.4 g of 18 mass % nitric acid aqueous solution, to which 182.0 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 4.6 (sec·g/cc). The results of the reaction evaluation are shown in Table 8. The results of the reaction evaluation after 100 sets and 200 sets of executions for accelerated reduction evaluation are also shown in Table 8.

Example B6

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 211.8 g of hot water at a temperature of about 90° C., 70.6 g of ammonium heptamolybdate was dissolved (liquid A). Furthermore, 37.1 g of bismuth nitrate, 21.5 g of cerium nitrate, 41.5 g of iron nitrate, 0.63 g of rubidium nitrate, 10.2 g of magnesium nitrate, 19.5 g of cobalt nitrate, and 9.8 g of nickel nitrate were dissolved in 41.3 g of 18 mass % nitric acid aqueous solution, to which 193.1 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 4.7 (sec·g/cc). The results of the reaction evaluation are shown in Table 8. The results of the reaction evaluation after 100 sets and 200 sets of executions for accelerated reduction evaluation are also shown in Table 8.

Example B7

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 210.8 g of hot water at a temperature of about 90° C., 70.3 g of ammonium heptamolybdate was dissolved (liquid A). Furthermore, 27.3 g of bismuth nitrate, 14.3 g of cerium nitrate, 20.0 g of iron nitrate, 1.94 g of rubidium nitrate, 0.67 g of potassium nitrate, 4.9 g of zinc nitrate, and 72.7 g of cobalt nitrate were dissolved in 40.5 g of 18 mass % nitric acid aqueous solution, to which 186.0 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 4.6 (sec·g/cc). The results of the reaction evaluation are shown in Table 8. The results of the reaction evaluation after 100 sets and 200 sets of executions for accelerated reduction evaluation are also shown in Table 8.

Comparative Example B1

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 203.4 g of hot water at a temperature of about 90° C., 67.8 g of ammonium heptamolybdate was dissolved (liquid A). Furthermore, 61.9 g of bismuth nitrate, 46.3 g of iron nitrate, 0.49 g of cesium nitrate, and 26.2 g of cobalt nitrate were dissolved in 40.4 g of 18 mass % nitric acid aqueous solution, to which 195.7 g of hot water at about 90° C. was added (liquid B).

The silica starting material and both of the liquid A and the liquid B were mixed, to which aqueous ammonia was added to adjust pH to 4.1. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 260° C. over 1 hour, and kept at the temperature for 4 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 55 g of the catalyst was placed in a fluidized bed reaction tube vycor glass having an inner diameter of 25 mm, and the ammoxidation of propylene was performed with a contact time of 5.6 (sec·g/cc). The results of the reaction evaluation are shown in Table 8. The results of the reaction evaluation after 100 sets and 200 sets of executions for accelerated reduction evaluation are also shown in Table 8.

Comparative Example B2

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 252.6 g of hot water at a temperature of about 90° C., 84.2 g of ammonium heptamolybdate was dissolved (liquid A). Furthermore, 5.8 g of bismuth nitrate, 3.4 g of cerium nitrate, 24.0 g of iron nitrate, 0.70 g of rubidium nitrate, 26.4 g of magnesium nitrate, and 75.6 g of nickel nitrate were dissolved in 41.8 g of 18 mass % nitric acid aqueous solution, to which 150.8 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 5.4 (sec·g/cc). The results of the reaction evaluation are shown in Table 8. The results of the reaction evaluation after 100 sets and 200 sets of executions for accelerated reduction evaluation are also shown in Table 8.

Comparative Example B3

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 249.9 g of hot water at a temperature of about 90° C., 83.3 g of ammonium heptamolybdate was dissolved (liquid A). Furthermore, 8.6 g of bismuth nitrate, 15.2 g of cerium nitrate, 26.9 g of iron nitrate, 0.23 g of rubidium nitrate, 20.1 g of magnesium nitrate, 34.5 g of cobalt nitrate, 0.36 g of potassium nitrate, and 23.0 g of nickel nitrate were dissolved in 40.9 g of 18 mass % nitric acid aqueous solution, to which 148.1 g of hot water at about 90° C. was added (liquid B).

The silica starting material and both of the liquid A and the liquid B were mixed, to which aqueous ammonia was added to adjust pH to 3.6. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 260° C. over 1 hour, and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 57 g of the catalyst was placed in a fluidized bed reaction tube vycor glass having an inner diameter of 25 mm, and the ammoxidation of propylene was performed with a contact time of 5.3 (sec·g/cc). The results of the reaction evaluation are shown in Table 8. The results of the reaction evaluation after 100 sets and 200 sets of executions for accelerated reduction evaluation are also shown in Table 8.

Comparative Example B4

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 216.3 g of hot water at a temperature of about 90° C., 72.1 g of ammonium heptamolybdate and 5.2 g of ammonium metavanadate were dissolved (liquid A). Furthermore, 44.4 g of bismuth nitrate, 43.8 g of iron nitrate, 0.46 g of cesium nitrate, and 31.8 g of cobalt nitrate were dissolved in 38.3 g of 18 mass % nitric acid aqueous solution, to which 161.9 g of hot water at about 90° C. was added (liquid B).

The silica starting material and both of the liquid A and the liquid B were mixed, to which aqueous ammonia was added to adjust pH to 4.1. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 2 hours in air, then to 250° C. over 1 hour, and kept at the temperature for 3 hours so as to produce a preliminarily calcined product. The produced preliminarily calcined product was finally calcined at 580° C. for 3 hours in air to produce a catalyst. The composition of the catalyst is shown in Table 6 and the measurement results of powder X-ray diffraction are shown in Table 7.

For the reaction evaluation of a catalyst, 55 g of the catalyst was placed in a fluidized bed reaction tube vycor glass having an inner diameter of 25 mm, and the ammoxidation of propylene was performed with a contact time of 5.9 (sec·g/cc). The results of the reaction evaluation are shown in Table 8. The results of the reaction evaluation after 100 sets and 200 sets of executions for accelerated reduction evaluation are also shown in Table 8.

Comparative Example B5

The same oxide catalyst precursor as in Example 31 was heated up to 250° C. over 1 hour in air and kept at the temperature for 3 hours so as to produce a preliminarily calcined product. The produced preliminarily calcined product was finally calcined at 570° C. for 3 hours in air to produce a catalyst. The composition of the catalyst is shown in Table 6 and the measurement results of powder X-ray diffraction are shown in Table 7.

For the reaction evaluation of a catalyst, 55 g of the catalyst was placed in a fluidized bed reaction tube vycor glass having an inner diameter of 25 mm, and the ammoxidation of propylene was performed with a contact time of 5.8 (sec·g/cc). The results of the reaction evaluation are shown in Table 8. The results of the reaction evaluation after 100 sets and 200 sets of executions for accelerated reduction evaluation are also shown in Table 8.

Example B8

Using the same catalyst as in Example B1, for the reaction evaluation, 57 g of the catalyst was placed in a fluidized bed reaction tube vycor glass having an inner diameter of 25 mm, and the ammoxidation of isobutylene was performed with a contact time of 5.4 (sec·g/cc). The results of the reaction evaluation are shown in Table 9. The results of the reaction evaluation after 100 sets and 200 sets of executions for accelerated reduction evaluation are also shown in Table 9.

Comparative Example B6

Using the same catalyst as in Comparative Example B5, for the reaction evaluation, 55 g of the catalyst was placed in a fluidized bed reaction tube vycor glass having an inner diameter of 25 mm, and the ammoxidation of isobutylene was performed with a contact time of 6.0 (sec·g/cc). The results of the reaction evaluation are shown in Table 9. The results of the reaction evaluation after 100 sets and 200 sets of executions for accelerated reduction evaluation are also shown in Table 9.

TABLE 6

| | Atomic composition | | | | | | | | Amount of SiO2 carrier |
|---|---|---|---|---|---|---|---|---|---|
| | Mo | Bi | Fe | Element A | Co | Element B | Element C | Fe/Co | wt % |
| Example B1 | 12.0 | 2.4 | 3.2 | La 1.6 | 3.2 | | Cs 0.08 | 1 | 50 |
| Example B2 | 12.0 | 2.6 | 3.4 | Ce 1.4 | 3.4 | | Cs 0.08 | 1 | 50 |
| Example B3 | 12.0 | 2.8 | 2.4 | Pr 1.2 | 4.0 | | Cs 0.09 | 0.6 | 50 |
| Example B4 | 12.0 | 1.2 | 3.2 | La2.0 Ca0.8 | 3.2 | | Cs 0.08 | 1 | 50 |
| Example B5 | 12.0 | 1.4 | 3.3 | Ce1.8 Pb0.8 | 5.1 | | Cs 0.12 | 0.64063 | 50 |
| Example B6 | 12.0 | 2.3 | 3.1 | Ce 1.5 | 2.0 | Ni 1.0 Mg 1.2 | Rb0.13 | 1.55 | 50 |
| Example B7 | 12.0 | 1.7 | 1.5 | Ce 1.0 | 7.5 | Zn 0.5 | Rb0.4 K0.2 | 0.2 | 50 |
| Example B8 | 12.0 | 2.0 | 3.2 | La 2.0 | 3.2 | | Cs 0.08 | 1 | 50 |
| Comparative Example B1 | 12.0 | 4.0 | 3.6 | 0.0 | 2.8 | | Cs 0.08 | 1.28571 | 50 |
| Comparative Example B2 | 12.0 | 0.3 | 1.5 | Ce 0.2 | 0.0 | Ni 6.5 Mg 2.6 | Rb0.12 | — | 50 |
| Comparative Example B3 | 12.0 | 0.45 | 1.7 | Ce 0.9 | 3.0 | Ni 2.0 Mg 2.0 | Rb0.04 K0.09 | 0.56667 | 50 |
| Comparative Example B4 | 12.0 | 2.7 | 3.2 | V 1.3 | 3.2 | | Cs 0.07 | 1 | 50 |
| Comparative | 12.0 | 2.0 | 3.2 | La 2.0 | 3.2 | | Cs 0.08 | 1 | 50 |

TABLE 6-continued

|  | Atomic composition | | | | | | | | Amount of SiO2 carrier |
|---|---|---|---|---|---|---|---|---|---|
|  | Mo | Bi | Fe | Element A | Co | Element B | Element C | Fe/Co | wt % |
| Example B5 | | | | | | | | | |
| Comparative Example B6 | 12.0 | 2.0 | 3.2 | La 2.0 | 3.2 | | Cs 0.08 | 1 | 50 |

TABLE 7

|  | Crystal structure | Intensity ratio Ia/Ib | X-ray diffraction peak 2θ° | | | |
|---|---|---|---|---|---|---|
| Example B1 | disorder phase | 3.3 | 18.34 | 28.16 | 33.66 | 46.10 |
| Example B2 | disorder phase | 3.2 | 18.33 | 28.12 | 33.60 | 46.19 |
| Example B3 | disorder phase | 2.2 | 18.31 | 28.22 | 33.61 | 46.16 |
| Example B4 | disorder phase | 2.9 | 18.32 | 28.15 | 33.66 | 46.13 |
| Example B5 | disorder phase | 2.4 | 18.33 | 28.14 | 33.64 | 46.14 |
| Example B6 | disorder phase | 2.6 | 18.34 | 28.15 | 33.66 | 46.14 |
| Example B7 | disorder phase | 2.0 | 18.34 | 28.20 | 33.68 | 46.18 |
| Example B8 | disorder phase | 3.3 | 18.34 | 28.16 | 33.66 | 46.10 |
| Comparative Example B1 | order phase | 1.1 | 18.10 | 28.02 | 33.30 | 45.90 |
|  |  |  | 18.48 | 28.35 | 34.06 | 46.46 |
| Comparative Example B2 | disorder phase | 1.6 | 18.33 | 28.14 | 33.64 | 46.14 |
| Comparative Example B3 | disorder phase | 1.7 | 18.34 | 28.16 | 33.66 | 46.17 |
| Comparative Example B4 | disorder phase | 3.2 | 18.38 | 28.23 | 33.68 | 46.17 |
| Comparative Example B5 | order phase | 1.3 | 18.12 | 28.04 | 33.34 | 45.88 |
|  |  |  | 18.50 | 28.37 | 34.02 | 46.44 |
| Comparative Example B6 | order phase | 1.3 | 18.12 | 28.04 | 33.34 | 45.88 |
|  |  |  | 18.50 | 28.37 | 34.02 | 46.44 |

TABLE 8

|  | Initial performance | | | Accelerated reduction evaluation after 100 sets | | | Accelerated reduction evaluation after 200 sets | | |
|---|---|---|---|---|---|---|---|---|---|
|  | Rate of conversion % | Acrylonitrile selectivity % | Acrylonitrile yield % | Rate of conversion % | Acrylonitrile selectivity % | Acrylonitrile yield % | Rate of conversion % | Acrylonitrile selectivity % | Acrylonitrile yield % |
| Example B1 | 99.2 | 87.3 | 86.6 | 99.1 | 87.4 | 86.6 | 99.1 | 87.3 | 86.5 |
| Example B2 | 99.2 | 87.1 | 86.4 | 99.1 | 87.0 | 86.2 | 99.0 | 87.0 | 86.1 |
| Example B3 | 99.3 | 86.3 | 85.7 | 99.1 | 85.5 | 84.7 | 99.0 | 852 | 84.3 |
| Example B4 | 99.3 | 86.8 | 86.2 | 99.1 | 86.6 | 85.8 | 99.0 | 86.6 | 85.7 |
| Example B5 | 99.1 | 86.0 | 85.2 | 99.0 | 85.8 | 84.9 | 98.5 | 85.2 | 83.9 |
| Example B6 | 99.3 | 86.6 | 86.0 | 99.1 | 86.3 | 85.5 | 99.0 | 86.1 | 85.2 |
| Example B7 | 99.2 | 85.8 | 85.1 | 98.6 | 85.4 | 84.2 | 98.3 | 85.0 | 83.6 |
| Comparative Example B1 | 99.1 | 77.0 | 76.3 | 90.3 | 71.2 | 64.3 | 85.0 | 66.3 | 56.4 |
| Comparative Example B2 | 99.2 | 87.2 | 86.5 | 88.7 | 82.0 | 72.7 | 79.0 | 76.0 | 60.0 |
| Comparative Example B3 | 99.0 | 85.0 | 84.2 | 92.0 | 81.0 | 74.5 | 89.3 | 78.0 | 69.7 |
| Comparative Example B4 | 99.0 | 83.0 | 82.2 | 90.3 | 73.6 | 66.5 | 84.6 | 70.8 | 59.9 |
| Comparative Example B5 | 99.0 | 77.2 | 76.4 | 89.8 | 71.8 | 64.5 | 84.6 | 67.9 | 57.4 |

TABLE 9

|  | Initial performance | | | Accelerated reduction evaluation after 100 sets | | | Accelerated reduction evaluation after 200 sets | | |
| --- | --- | --- | --- | --- | --- | --- | --- | --- | --- |
|  | Rate of conversion % | Methacryl-onitrile selectivity % | Methacryl-onitrile yield % | Rate of conversion % | Methacryl-onitrile selectivity % | Methacryl-onitrile yield % | Rate of conversion % | Methacryl-onitrile selectivity % | Methacryl-onitrile yield % |
| Example B8 | 99.2 | 83.0 | 82.3 | 99.1 | 82.9 | 82.2 | 99.1 | 82.8 | 82.1 |
| Comparative Example B6 | 99.2 | 74.0 | 73.4 | 89.8 | 71.0 | 63.8 | 84.5 | 87.0 | 73.5 |

<X-ray Diffraction Peaks of Catalysts Obtained in Example B1 and Comparative Example B1>

In FIG. 9, the X-ray diffraction peaks of catalysts obtained in Example B1 and Comparative Example B1 are illustrated. In FIG. 10, an enlarged chart of X-ray diffraction peaks for the range of 2θ=15 to 30° in FIG. 9 is illustrated. In FIG. 11, an enlarged chart for the range of 2θ=30 to 50° is illustrated. In FIG. 9 and FIG. 10, it was illustrated that the catalyst obtained in Example B1 had X-ray diffraction peaks at least at 2θ=18.28° for (101) plane, 28.16° for (112) plane, 33.60° for (200) plane, and 46.00°, with a peak intensity ratio (Ia/Ib)=3.3, wherein Ia represents the peak intensity at 2θ=33.60° and Ib represents the peak intensity at 2θ=34.06°. It can be assumed that the crystal structure of disordered phase of $Bi_{3-x}A_xFe_1Mo_2O_{12}$ was formed in the catalyst obtained in Example B1.

On the other hand, in the X-ray diffraction of the catalyst obtained in Comparative Example B1, no peak was observed at 18.30°±0.05° for (101) plane, 28.20°±0.05° for (112) plane, 33.65°±0.05° for (200) plane, and 46.15°±0.05° for (204) plane. It can be therefore assumed that the crystal structure of disordered phase of $Bi_{3-x}A_xFe_1Mo_2O_{12}$ was not formed in the catalyst obtained in Comparative Example B1.

The comparison of X-ray diffraction between the catalysts obtained in Example B1 and Comparative Example B1 are as follows. Corresponding to the peak at 18.34° for (101) plane of the catalyst obtained in Example B1, split peaks were observed at 18.10° for (310) plane and at 18.45° for (111) plane in the catalyst obtained in Comparative Example B1. Corresponding to the peak at 28.20°±0.2° for (112) plane of the catalyst obtained in Example B1, split peaks were observed at 28.00° for (221) plane and at 28.35° for (42-1) plane in the catalyst obtained in Comparative Example B1. Corresponding to the peak at 33.65°±0.2° for (200) plane of the catalyst obtained in Example B1, split peaks were observed at 33.30° for (600) plane and at 34.10° for (202) plane in the catalyst obtained in Comparative Example B1. Corresponding to the peak at 46.15°±0.2° for (204) plane of the catalyst obtained in Example B1, split peaks were observed at 45.90° for (640) plane and at 46.45° for (242) plane in the catalyst obtained in Comparative Example B1. The catalyst obtained in Example B1 had a peak intensity ratio (Ia/Ib)=1.0, wherein Ia represents the peak intensity at 2θ=33.60° and Ib represents the peak intensity at 2θ=34.06°. It can be assumed that the crystal structure of a disordered phase of $Bi_{3-x}A_xFe_1Mo_2O_{12}$ was formed in the catalyst obtained in Example B1. On the other hand, it can be assumed that an ordered phase was formed in the catalyst obtained in Comparative Example B1 instead of a disordered phase of $Bi_{3-x}A_xFe_1Mo_2O_{12}$.

Example C is provided in the following to further illustrate a third aspect of the present invention, but is not intended to limit the scope of the third aspect of the present invention thereto. Since the atomic ratio of oxygen in an oxide catalyst is determined by the atomic valence conditions of other elements, the atomic ratio of oxygen is omitted in the formula representing the composition of the catalysts in Example C and Comparative Example C. The composition ratio of each element in an oxide catalyst was calculated from the composition ratio for preparation.

In Example C and Comparative Example C, the reaction performance was represented by rate of conversion, selectivity, and yield, which are defined by the following expressions. The term "number of moles of starting material" refers to number of moles of olefin and/or alcohol.

Rate of conversion (%)=(number of moles of reacted olefin and/or alcohol/number of moles of supplied olefin and/or alcohol)×100

Selectivity (%)=(number of moles of produced unsaturated aldehyde/number of moles of reacted olefin and/or alcohol)×100

Yield (%)=(number of moles of produced unsaturated aldehyde/number of moles of supplied olefin and/or alcohol)×100

Example C1

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 211.9 g of hot water at a temperature of about 90° C., 70.6 g of ammonium heptamolybdate was dissolved (liquid A). Furthermore, 32.3 g of bismuth nitrate, 28.7 g of cerium nitrate, 45.6 g of iron nitrate, 1.03 g of cesium nitrate, and 29.2 g of cobalt nitrate were dissolved in 40.9 g of 18 mass % nitric acid aqueous solution, to which 190.3 g of hot water at about 90° C. was added (liquid B).

The silica starting material and both of the liquid A and the liquid B were mixed. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 1 hour or more in air, then to 250° C. over 2 hours in total, and kept at 250° C. for 3 hours so as to produce a preliminarily calcined product. The produced preliminarily calcined product was finally calcined at 600° C. for 3 hours in air to produce an oxide catalyst. The composition of the oxide catalyst is shown in Table 10.

Using the thus produced oxide catalyst, unsaturated aldehyde was produced. Specifically, 40 g of the oxide catalyst was placed in a fluidized bed reaction tube vycor glass having an inner diameter of 25 mm. A mixed starting material gas (isobutylene concentration: 8% by volume) with a molar composition ratio of isobutylene/air/helium=1/8.1/balance was supplied through the reaction tube at a reaction temperature of 440° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C2

40 g of the same oxide catalyst as in Example C1 was used. A mixed starting material gas (isobutylene concentration: 8% by volume) with a molar composition ratio of isobutylene/air/helium=1/8.8/balance was supplied at a reaction temperature of 430° C. under a reaction pressure of 0.05 MPa at a flow rate of 725 cm$^2$/min (converted to NTP) so as to perform the synthesis reaction of methacrolein. The oxygen concentration at the reactor exit, the contact time between the catalyst and the mixed gas, and the reaction evaluation results on that occasion are shown in Table 11.

Example C3

30 g of the same oxide catalyst as in Example C1 was used. A mixed starting material gas (isobutylene concentration: 8% by volume) with a molar composition ratio of isobutylene/air/helium=1/9.4/balance was supplied at a reaction temperature of 440° C. under a reaction pressure of 0.05 MPa at a flow rate of 794 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C4

40 g of the same oxide catalyst as in Example C1 was used. A mixed starting material gas (isobutylene concentration: 8% by volume) with a molar composition ratio of isobutylene/air/helium=1/7.9/balance was supplied at a reaction temperature of 440° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C5

40 g of the same oxide catalyst as in Example C1 was used. A mixed starting material gas (isobutylene concentration: 8% by volume) with a molar composition ratio of isobutylene/air/helium=1/9.5/balance was supplied at a reaction temperature of 440° C. under a reaction pressure of 0.05 MPa at a flow rate of 625 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C6

35 g of the same oxide catalyst as in Example C1 was used. A mixed starting material gas (isobutylene concentration: 8% by volume) with a molar composition ratio of isobutylene/air/helium 1/8.8/balance was supplied at a reaction temperature of 460° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C7

40 g of the same oxide catalyst as in Example C1 was used. A mixed starting material gas (isobutylene concentration: 8% by volume) with a molar composition ratio of isobutylene/air/helium=1/8.1/balance was supplied at a reaction temperature of 400° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C8

First, 125.0 g of 40 mass % silica sol which contained 26 mass % $SiO_2$ of primary silica particles having an average diameter of 44 nm, and 147.1 g of 34 mass % aqueous silica sol which contained 30 mass % $SiO_2$ of primary silica particles having an average diameter of 12 nm, and 61.3 g of water were mixed to produce 30 mass % silica starting material.

In 211.8 g of hot water at a temperature of about 90° C., 70.6 g of ammonium heptamolybdate was dissolved (liquid A). Furthermore, 25.8 g of bismuth nitrate, 18.6 g of cerium nitrate, 18.7 g of lanthanum nitrate, 42.9 g of iron nitrate, 1.03 g of cesium nitrate, and 31.1 g of cobalt nitrate were dissolved in 37.5 g of 18 mass % nitric acid aqueous solution, to which 157.5 g of hot water at about 90° C. was added (liquid B).

The silica starting material and both of the liquid A and the liquid B were mixed. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 1 hour or more in air, then to 250° C. over 2 hours in total, and kept at 250° C. for 3 hours so as to produce a preliminarily calcined product. The produced preliminarily calcined product was finally calcined at 590° C. for 3 hours in air to produce an oxide catalyst. The composition of the oxide catalyst is shown in Table 10.

Using the thus produced oxide catalyst, unsaturated aldehyde was produced. Specifically, 40 g of the oxide catalyst was placed in a fluidized bed reaction tube vycor glass having an inner diameter of 25 mm. A mixed starting material gas (isobutylene concentration: 8% by volume) with a molar composition ratio of isobutylene/air/helium=1/8.1/balance was supplied to the reaction tube at a reaction temperature of 440° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Example C9

First, 125.0 g of 40 mass % silica sol which contained 26 mass % SiO$_2$ of primary silica particles having an average diameter of 44 nm, and 147.1 g of 34 mass % aqueous silica sol which contained 30 mass % SiO$_2$ of primary silica particles having an average diameter of 12 nm, and 61.3 g of water were mixed to produce 30 mass % silica starting material.

In 214.5 g of hot water at a temperature of about 90° C., 71.5 g of ammonium heptamolybdate was dissolved (liquid A). Furthermore, 18.0 g of bismuth nitrate, 39.2 g of cerium nitrate, 4.9 g of nickel nitrate, 3.4 g of magnesium nitrate, 43.4 g of iron nitrate, 1.48 g of rubidium nitrate, and 31.6 g of cobalt nitrate were dissolved in 41.6 g of 18 mass % nitric acid aqueous solution, to which 192.3 g of hot water at about 90° C. was added (liquid B).

The silica starting material and both of the liquid A and the liquid B were mixed. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up from 100° C. to 200° C. over 1 hour or more in air, then to 250° C. over 2 hours in total, and kept at 250° C. for 3 hours so as to produce a preliminarily calcined product. The produced preliminarily calcined product was finally calcined at 580° C. for 3 hours in air to produce an oxide catalyst. The composition of the oxide catalyst is shown in Table 10.

Using the thus produced oxide catalyst, unsaturated aldehyde was produced. Specifically, 40 g of the oxide catalyst was placed in a fluidized bed reaction tube vycor glass having an inner diameter of 25 mm. A mixed starting material gas (isobutylene concentration: 8% by volume) with a molar composition ratio of isobutylene/air/helium=1/8.1/balance was supplied through the reaction tube at a reaction temperature of 440° C. under a reaction pressure of 0.05 MPa at a flow rate of 595 cm$^2$/min (converted to NTP) so as to perform the synthesis reaction of methacrolein. The oxygen concentration at the exit, the contact time between the catalyst and the mixed gas, and the reaction evaluation results on that occasion are shown in Table 11.

Example C10

40 g of the same oxide catalyst as in Example C1 was used. A mixed starting material gas (isobutylene concentration: 8% by volume) with a molar composition ratio of isobutylene/air/helium=1/10.2/balance was supplied at a reaction temperature of 440° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

Comparative Example C1

First, 125.0 g of 40 mass % silica sol which contained 26 mass % SiO$_2$ of primary silica particles having an average diameter of 44 nm, and 147.1 g of 34 mass % aqueous silica sol which contained 30 mass % SiO$_2$ of primary silica particles having an average diameter of 12 nm, and 61.3 g of water were mixed to produce 30 mass % silica starting material.

In 221.4 g of hot water at a temperature of about 90° C., 73.8 g of ammonium heptamolybdate was dissolved (liquid A). Furthermore, 27.0 g of bismuth nitrate, 6.0 g of cerium nitrate, 14.0 g of iron nitrate, 2.68 g of cesium nitrate, 0.70 g of potassium nitrate, and 81.4 g of cobalt nitrate were dissolved in 40.4 g of 18 mass % nitric acid aqueous solution, to which 175.3 g of hot water at about 90° C. was added (liquid B).

The silica starting material and both of the liquid A and the liquid B were mixed. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up to 250° C. over 2 hours in air, and kept at 250° C. for 3 hours so as to produce a preliminarily calcined product. The produced preliminarily calcined product was finally calcined at 570° C. for 2 hours in air to produce an oxide catalyst. The composition of the oxide catalyst is shown in Table 10.

Using the thus produced oxide catalyst, unsaturated aldehyde was produced. Specifically, 40 g of the oxide catalyst was placed in a fluidized bed reaction tube vycor glass having an inner diameter of 25 mm. A mixed starting material gas (isobutylene concentration: 8% by volume) with a molar composition ratio of isobutylene/air/helium=1/8.1/balance was supplied through the reaction tube at a reaction temperature of 440° C. under a reaction pressure of 0.05 MPa at a flow rate of 595 cm$^2$/min (converted to NTP) so as to perform the synthesis reaction of methacrolein. The oxygen concentration at the exit, the contact time between the catalyst and the mixed gas, and the reaction evaluation results on that occasion are shown in Table 11.

Comparative Example C2

First, 125.0 g of 40 mass % silica sol which contained 26 mass % SiO$_2$ of primary silica particles having an average diameter of 44 nm, and 147.1 g of 34 mass % aqueous silica sol which contained 30 mass % SiO$_2$ of primary silica particles having an average diameter of 12 nm, and 61.3 g of water were mixed to produce 30 mass % silica starting material.

In 202.8 g of hot water at a temperature of about 90° C., 67.6 g of ammonium heptamolybdate was dissolved (liquid A). Furthermore, 61.7 g of bismuth nitrate, 43.6 g of iron nitrate, 0.98 g of cesium nitrate, and 28.0 g of cobalt nitrate were dissolved in 40.3 g of 18 mass % nitric acid aqueous solution, to which 195.7 g of hot water at about 90° C. was added (liquid B).

The silica starting material and both of the liquid A and the liquid B were mixed. The liquid was then agitated and mixed at about 55° C. for about 4 hours so as to produce a starting material slurry. The starting material slurry was transported to a spray dryer so as to be spray dried at an entrance temperature of 250° C. and at an exit temperature of 140° C. An oxide catalyst precursor was thus produced. The produced oxide catalyst precursor was heated up to 250° C. over 2 hours in air, and kept at 250° C. for 3 hours so as to produce a preliminarily calcined product. The produced preliminarily calcined product was finally calcined at 600° C. for 3 hours in air to produce an oxide catalyst. The composition of the oxide catalyst is shown in Table 10.

Using the thus produced oxide catalyst, unsaturated aldehyde was produced. Specifically, 40 g of the oxide catalyst was placed in a fluidized bed reaction tube vycor glass having an inner diameter of 25 mm. A mixed starting material gas (isobutylene concentration: 8% by volume) with a molar composition ratio of isobutylene/air/helium=1/8.1/balance was supplied through the reaction tube at a reaction temperature of 440° C. under a reaction pressure of 0.05 MPa at a flow rate of 595 cm$^2$/min (converted to NTP) so as to perform the synthesis reaction of methacrolein. The oxygen concentration at the reactor exit, the contact time between the oxide catalyst and the mixed gas, and the reaction evaluation results on that occasion are shown in Table 11.

TABLE 10

| Number | Atomic composition | | | | | | | Fe/Co | Amount of SiO2 carrier wt % | Crystal structure |
|---|---|---|---|---|---|---|---|---|---|---|
| | Mo | Bi | Fe | Co | Element A | Element B | Element C | | | |
| Example C1 | 12.0 | 2.0 | 3.4 | 3.0 | Ce 2.0 | | Cs 0.16 | 1.13 | 50 | disorder phase |
| Example C2 | 12.0 | 2.0 | 3.4 | 3.0 | Ce 2.0 | | Cs 0.16 | 1.13 | 50 | disorder phase |
| Example C3 | 12.0 | 2.0 | 3.4 | 3.0 | Ce 2.0 | | Cs 0.16 | 1.13 | 50 | disorder phase |
| Example C4 | 12.0 | 2.0 | 3.4 | 3.0 | Ce 2.0 | | Cs 0.16 | 1.13 | 50 | disorder phase |
| Example C5 | 12.0 | 2.0 | 3.4 | 3.0 | Ce 2.0 | | Cs 0.16 | 1.13 | 50 | disorder phase |
| Example C6 | 12.0 | 2.0 | 3.4 | 3.0 | Ce 2.0 | | Cs 0.16 | 1.13 | 50 | disorder phase |
| Example C7 | 12.0 | 2.0 | 3.4 | 3.0 | Ce 2.0 | | Cs 0.16 | 1.13 | 50 | disorder phase |
| Example C8 | 12.0 | 1.6 | 3.2 | 3.2 | Ce 1.3 La1.3 | | Cs 0.16 | 1.00 | 50 | disorder phase |
| Example C9 | 12.0 | 1.1 | 3.2 | 3.2 | Ce 2.7 | Ni0.5 Mg0.4 | Rb 0.30 | 1.00 | 50 | disorder phase |
| Example C10 | 12.0 | 2.0 | 3.4 | 3.0 | Cc 2.0 | | Cs 0.16 | 1.13 | 50 | disorder phase |
| Comparative Example C1 | 12.0 | 1.6 | 1.0 | 8.0 | Ce 0.4 | | Cs 0.4 K0.2 | 0.13 | 50 | order phase |
| Comparative Example C2 | 12.0 | 4.0 | 3.4 | 3.0 | | | Cs0.16 | 1.13 | 50 | order phase |

TABLE 11

| | Temperature ° C. | Exit oxygen concentration % by volume | Contact time θ sec | Rate of conversion % | Methacrolein selectivity % | Methacrolein yield % |
|---|---|---|---|---|---|---|
| Example C1 | 440 | 0.05 | 2.3 | 99.1 | 74.2 | 73.5 |
| Example C2 | 430 | 0.1 | 1.9 | 99.1 | 73.8 | 73.1 |
| Example C3 | 440 | 0.15 | 1.3 | 99.0 | 72.7 | 72.0 |
| Example C4 | 440 | 0.03 | 2.3 | 99.2 | 71.8 | 71.2 |
| Example C5 | 440 | 0.4 | 21 | 99.2 | 70.1 | 69.5 |
| Example C6 | 460 | 0.1 | 2.0 | 99.0 | 70.7 | 70.0 |
| Example C7 | 400 | 0.05 | 2.4 | 99.3 | 70.2 | 69.7 |
| Example C8 | 440 | 0.05 | 2.3 | 99.1 | 74.5 | 73.8 |
| Example C9 | 440 | 0.05 | 2.3 | 99.2 | 74.4 | 73.8 |
| Example C10 | 440 | 0.6 | 2.3 | 99.2 | 68.2 | 67.7 |
| Comparative Example C1 | 440 | 0.05 | 2.3 | 90.1 | 70.0 | 63.1 |
| Comparative Example C2 | 440 | 0.05 | 2.5 | 99.1 | 66.5 | 65.9 |

<Powder X-ray Diffraction (XRD) Measurement>

X-ray diffraction (XRD) measurement of the oxide catalyst was performed for the X-ray diffraction angle range of 2θ=5° to 60°. A peak resulting from the X-ray diffraction angle (2θ) for (002) plane of a composite oxide of Co and Mo was shown at 26.46°±0.02°. Bivalent Fe solid-dissolved in the composite oxide of Co and Mo forms a composite, allowing the peak to be shifted due to the difference in the ion radius between $Co^{2+}$ and $Fe^{2+}$. Since the solid-dissolved bivalent Fe constitutes a composite structure, the peak resulting from the composite oxide which comprises Co, Mo, and bivalent Fe is not shown at 26.46° but at 26.46°−α° (0<α), wherein α° represents the shift value. The presence of a peak in the range of 26.30 to 26.40 is attributed to the crystal formation of a ternary component system $Co^{2+}$—$Fe^{2+}$—Mo—O.

The XRD measurement was performed based on the above. In XRD measurement, the (111) plane and the (200) plane of a $LaB_6$ compound as standard reference material 660 according to National Institute of Standards & Technology were measured, such that the values were normalized to 37.441° and 43.506°, respectively.

An XRD apparatus Bruker D8 Advance was used. The XRD measurement conditions were as follows: an X-ray output of 40 kV-40 mA, a divergence slit (DS) of 0.3°, a step width of 0.01°/step, a counting time of 2.0 sec, and a measurement range of 2θ=5° to 45°.

In FIG. 12, the XRD (2θ=10 to 60°) of the oxide catalyst before and after gas-phase catalytic oxidation reaction of olefin in Example C1 is illustrated. In FIG. 13, an enlarged chart for the range of 2θ=25 to 27° in FIG. 12 is illustrated. The oxide catalyst before gas-phase catalytic oxidation reaction of olefin in Example C1 had an XRD peak from $CoMoO_4$ (002) at 2θ=26.46°, and the oxide catalyst after reaction had an XRD peak from $CoMoO_4$ (002) at 2θ=26.34°. It was thus found that bivalent Fe was solid-dissolved in $CoMoO_4$.

In FIG. 14, the XRD (2θ=10 to 60°) of the oxide catalyst before and after gas-phase catalytic oxidation reaction of olefin in Comparative Example C1 is illustrated. In FIG. 15, an enlarged chart for the range of 2θ=25 to 27° in FIG. 14 is illustrated. The oxide catalyst before gas-phase catalytic oxidation reaction of olefin in Comparative Example C1 had an XRD peak from $CoMoO_4$ (002) at 2θ=26.46°, and the oxide catalyst after reaction had an XRD peak from $CoMoO_4$ (002) at 2θ=26.46°. It was thus found that bivalent Fe was not solid-dissolved in $CoMoO_4$. This was attributed to the atomic ratio of iron to cobalt (b/c), not satisfying the following expression: b/c≥1.

<X-ray Diffraction Peaks of Catalysts Obtained in Example C1 and Comparative Example C2>

In FIG. 16, the X-ray diffraction peaks of catalysts obtained in Example C1 and Comparative Example C2 are illustrated. In FIG. 16, it was illustrated that the catalyst obtained in Example C1 had X-ray diffraction peaks at least at 2θ=18.32° for (101) plane, 28.18° for (112) plane, 33.66° for (200) plane, and 46.12°, with a peak intensity ratio (Ia/Ib)= 3.2, wherein Ia represents the peak intensity at 2θ=33.66° and Ib represents the peak intensity at 2θ=34.06°. It can be assumed that the crystal structure of disordered phase of $Bi_{3-x}A_xFe_1Mo_2O_{12}$ was formed in the catalyst obtained in Example C1.

In the X-ray diffraction of the catalyst obtained in Comparative Example C2, no peak was observed at 18.30°±0.05° for (101) plane, 28.20°±0.05° for (112) plane, 33.65°±0.05° for (200) plane, and 46.15°±0.05° for (204) plane. It can be therefore assumed that the crystal structure of disordered phase of $Bi_{3-x}A_xFe_1Mo_2O_{12}$ was not formed in the catalyst obtained in Comparative Example C2.

The comparison of X-ray diffraction between the catalysts obtained in Example C1 and Comparative Example C2 are as follows. Corresponding to the peak at 18.30°±0.05° for (101) plane of the catalyst obtained in Example C1, split peaks were observed at 18.06° for (310) plane and at 18.44° for (111) plane in the catalyst obtained in Comparative Example C2. Corresponding to the peak at 28.20°±0.05° for (112) plane of the catalyst obtained in Example C1, split peaks were observed at 28.00° for (221) plane and at 28.32° for (42-1) plane in the catalyst obtained in Comparative Example C2. Corresponding to the peak at 33.65°±0.05° for (200) plane of the catalyst obtained in Example C1, split peaks were observed at 33.52° for (600) plane and at 33.98° for (202) plane in the catalyst obtained in Comparative Example C2. Corresponding to the peak at 46.15°±0.05° for (204) plane of the catalyst obtained in Example C1, split peaks were observed at 45.82° for (640) plane and at 46.40° for (242) plane in the catalyst obtained in Comparative Example C2. With a peak intensity ratio (Ia/Ib)=0.94, wherein Ia represents the peak intensity at 2θ=33.52° and Ib represents the peak intensity at 2θ=33.98°, it can be assumed that an ordered phase was formed in the catalyst obtained in Comparative Example C2 instead of a disordered phase of $Bi_{3-x}A_xFe_1Mo_2O_{12}$.

The present application is based on Japanese Patent Application No. 2012-216071 filed on Sep. 28, 2012, in Japanese Patent Office, Japanese Patent Application No. 2012-253243 filed on Nov. 19, 2012, in Japanese Patent Office, and Japanese Patent Application No. 2013-033663 filed on Feb. 22, 2013, in Japanese Patent Office, the entirety of which is incorporated herein by reference.

INDUSTRIAL APPLICABILITY

The present invention is industrially applicable to an oxide catalyst for use in producing unsaturated aldehyde or diolefin from olefin and/or alcohol.

The invention claimed is:

1. An oxide catalyst for use in the production of unsaturated aldehyde, diolefin, or unsaturated nitrile from olefin and/or alcohol, the oxide catalyst satisfying the following (1) to (3):
   (1) the oxide catalyst comprises molybdenum, bismuth, iron, cobalt, and an element A having an ion radius larger than 0.96 Å (except for potassium, cesium, and rubidium);
   (2) an atomic ratio a of the bismuth to 12 atoms of the molybdenum is 1≤a≤5, an atomic ratio b of the iron to 12 atoms of the molybdenum is 1.5≤b≤6, an atomic ratio c of the element A to 12 atoms of the molybdenum is 1≤c≤5, and an atomic ratio d of the cobalt to 12 atoms of the molybdenum is 1≤d≤8; and
   (3) the oxide catalyst comprises a disordered phase consisting of a crystal system comprising the molybdenum, the bismuth, the iron, and the element A.

2. The oxide catalyst according to claim 1, wherein the oxide catalyst has a single peak in each range of diffraction angles (2θ) of 18.30°±0.2°, 28.20°±0.2°, 33.65°±0.2°, and 46.15°±0.2° in X-ray diffraction, and
an intensity ratio (Ia/Ib) of intensity (Ia) of peak a at 2θ=33.65°±0.2° to intensity (Ib) of peak b at 2θ=34.10°±0.2° is 2.0 or larger.

3. The oxide catalyst according to claim 1, wherein the oxide catalyst has a composition represented by the following composition formula (1):

$$Mo_{12}Bi_aFe_bA_cCo_dB_eC_fO_g \qquad (1)$$

wherein Mo represents molybdenum; Bi represents bismuth; Fe represents iron; the element A represents an element having an ion radius larger than 0.96 Å(except for potassium, cesium, and rubidium); Co represents cobalt; an element B represents at least one element selected from the group consisting of magnesium, zinc, copper, nickel, manganese, chromium, and tin; an element C represents at least one element selected from the group consisting of potassium, cesium, and rubidium; a to g each represent the atomic ratio of each element to 12 Mo atoms wherein the atomic ratio a of Bi is $1 \leq a \leq 5$, the atomic ratio b of Fe is $1.5 \leq b \leq 6$, the atomic ratio c of the element A is $1 \leq c \leq 5$, and the atomic ratio d of Co is $1 \leq d \leq 8$, an atomic ratio e of the element B is $0 \leq e < 3$, an atomic ratio f of the element C is $0 \leq f \leq 2$, and an ratio of Fe/Co is $0.8 \leq b/d$; and g represents an atomicity of oxygen determined by an valences of constituent elements other than oxygen.

4. The oxide catalyst according to claim 1, further comprising at least one selected from the group consisting of silica, alumina, titania, and zirconia as a carrier.

5. A method for producing an oxide catalyst, comprising:
   a mixing step of mixing a starting material constituting the catalyst, comprising molybdenum, bismuth, iron, cobalt, and an element A having an ion radius larger than 0.96 Å(except for potassium, cesium, and rubidium), to obtain a slurry;
   a drying step of drying the slurry thus obtained to obtain a dried product; and
   a calcination step of calcining the dried product thus obtained, wherein
   the calcination step comprises a heating step of gradually heating the dried product from 100° C. to 200° C. over 1 hour or longer.

6. The method for producing the oxide catalyst according to claim 5, wherein the slurry has a pH of 8 or lower.

7. The method for producing the oxide catalyst according to claim 5, wherein the calcination step comprises:
   a preliminary calcination step of preliminarily calcining the dried product at a temperature of 200 to 300° C. to obtain a preliminarily calcined product; and
   a final calcination step of finally calcining the preliminarily calcined product thus obtained at a temperature of 300° C. or higher to obtain the catalyst.

8. A method for producing unsaturated aldehyde, comprising an unsaturated aldehyde production step of oxidizing olefin and/or alcohol using the oxide catalyst according to claim 1 to obtain the unsaturated aldehyde.

9. The method for producing unsaturated aldehyde according to claim 8, wherein the olefin and/or the alcohol is at least one selected from the group consisting of propylene, isobutylene, propanol, isopropanol, isobutanol, and t-butyl alcohol.

10. The method for producing unsaturated aldehyde according to claim 8, wherein the unsaturated aldehyde production step comprises a discharging step of discharging a product gas comprising the unsaturated aldehyde from a fluidized-bed reactor through the gas-phase catalytic oxidation reaction of the olefin and/or the alcohol with an oxygen source in the fluidized-bed reactor.

11. The method for producing unsaturated aldehyde according to claim 8, wherein
   the gas-phase catalytic oxidation reaction is performed at a reaction temperature of 400 to 500° C., and
   the product gas discharged from the fluidized-bed reactor has an oxygen concentration of 0.03 to 0.5% by volume.

12. A method for producing diolefin, comprising a diolefin production step of oxidizing monoolefin having 4 or more carbon atoms using the oxide catalyst according to claim 1 to obtain the diolefin.

13. A method for producing unsaturated nitrile, comprising an unsaturated nitrile production step of reacting at least one selected from the group consisting of propylene, isobutylene, propanol, isopropanol, isobutanol, and t-butyl alcohol, with molecular oxygen and ammonia in a fluidized-bed reactor using the oxide catalyst according to claim 1 to obtain the unsaturated nitrile.

* * * * *